(12) United States Patent
Browse et al.

(10) Patent No.: US 8,101,818 B2
(45) Date of Patent: Jan. 24, 2012

(54) ENHANCEMENT OF HYDROXY FATTY ACID ACCUMULATION IN OILSEED PLANTS

(75) Inventors: John A. Browse, Palouse, WA (US); Jay M. Shockey, Mandeville, LA (US); Julie Jeannine Burgal, Davis, CA (US)

(73) Assignee: Washington State University, Pullman, WA (US)

( * ) Notice: Subject to any disclaimer, the term of this patent is extended or adjusted under 35 U.S.C. 154(b) by 697 days.

(21) Appl. No.: 11/915,146

(22) PCT Filed: May 22, 2006

(86) PCT No.: PCT/US2006/019829
§ 371 (c)(1),
(2), (4) Date: May 30, 2008

(87) PCT Pub. No.: WO2006/127655
PCT Pub. Date: Nov. 30, 2006

(65) Prior Publication Data
US 2008/0282427 A1 Nov. 13, 2008

Related U.S. Application Data

(60) Provisional application No. 60/683,170, filed on May 20, 2005.

(51) Int. Cl.
*A01H 1/00* (2006.01)
*A01H 5/00* (2006.01)
*A01H 5/10* (2006.01)
*A01H 15/00* (2006.01)
*C07H 21/04* (2006.01)
*C12N 5/14* (2006.01)
*C12N 15/82* (2006.01)

(52) U.S. Cl. ........ 800/278; 800/281; 800/306; 800/312; 800/314; 800/320.1; 800/322; 536/23.6; 435/410; 435/320.1; 435/468; 435/254.1

(58) Field of Classification Search ............... None
See application file for complete search history.

(56) References Cited

U.S. PATENT DOCUMENTS
7,135,617 B2 * 11/2006 Lardizabal et al. ........... 800/281
7,195,901 B1 * 3/2007 McKeon et al. ............... 435/193

FOREIGN PATENT DOCUMENTS
WO 2004/011671 2/2004

OTHER PUBLICATIONS

Bafor et al., "Ricinoleic acid biosynthesis and triacylglycerol assembly in microsomal preparations from developing castor-bean (*Ricinus communis*) endosperm," Biochemical Journal, 1991, pp. 507-514, vol. 280.
Broun et al., "Accumulation of Ricinoleic, Lesquerolic, and Densipolic Acids in Seeds of Transgenic *Arabidopsis* Plants That Express a Fatty Acyl Hydroxylase cDNA from Castor Bean," Plant Physiology, 1997, pp. 933-942, vol. 113.
Broun et al., "A bifunctional oleate 12-hydroxylase: desaturase from *Lesquerella fendleri*," The Plant Journal, 1998, pp. 201-210, vol. 13, No. 2.
Brown et al., "Substrate selectivity of plant and microbial lysophosphatidic acid acyltransferases," Phytochemistry, 2002, pp. 493-501, vol. 61.
Clough et al., "Floral dip: a simplified method for Agrobacterium-mediated transformation of *Arabidopsis thaliana*," Plant Journal, Dec. 1998, pp. 734-743, vol. 16, No. 6.
Dahlqvist et al., "Phospholipid:diacylglycerol acyltransferase: An enzyme that catalyzes the acyl-CoA-independent formation of triacylglycerol in yeast and plants," The Proceedings of the National Academy of Sciences, Jun. 6, 2000, pp. 6487-6492, vol. 97, No. 12.
Galliard et al., "Fat Metabolism in Higher Plants," The Journal of Biological Chemistry, Dec. 25, 1966, pp. 5806-5812, vol. 241, No. 24.
Hajra, "On Extraction of Acyl and Alkyl Dihydroxyacetone Phosphate from Incubation Mixtures," Lipids, 1974, pp. 502-505, vol. 9, No. 8.
Hayes et al., "The Triglyceride Composition, Structure, and Presence of Estolides in the Oils of *Lesquerella* and Related Species," Journal of American Oil Chemists Society, 1995, pp. 559-569, vol. 72, No. 5.
Kennedy, "Biosynthesis of complex lipids," Federation Proceedings, Dec. 1961, pp. 934-940, vol. 20. Kim et al., "Ubiquitous and Endoplasmic Reticulum-Located Lysophosphatidyl Acyltransferase, LPAT2, Is Essential for Female but Not Male Gametophyte Development in *Arabidopsis*," The Plant Cell, Apr. 2005, pp. 1073-1089, vol. 17.
Kunst et al., "Fatty," Plant Physiology and Biochemistry, 1992, pp. 425-434, vol. 30.
Lardizabal et al., "DGAT2 Is a New Diacylglycerol Acyltransferase Gene Family," The Journal of Biological Chemistry, Oct. 19, 2001, pp. 38862-38869, vol. 276, No. 42.
Lin et al., "Biosynthesis of Triacylglycerols Containing Ricinoleate in Castor Microsomes Using 1-Acyl-2-oleoyl-*sn*-glycero-3-phosphocholine as the Substrate of Oleoyl-12-hydroxylase," Lipids, 1998, pp. 59-69, vol. 33, No. 1.

(Continued)

*Primary Examiner* — Eileen B O Hara
(74) *Attorney, Agent, or Firm* — Barry L. Davison; David Wright Tremaine LLP

(57) ABSTRACT

Particular aspects provide six novel *Ricinus communis* cDNA clones, including cloned sequences of: DGAT (RcDGAT1 and RcDGAT2); RcLPAT; LACS (RcLACS4), and PDAT (RcPDAT1A and RcPDAT1B). Additional aspects provide methods for substantially enhanced accumulation of hydroxy fatty acid (HFA) in transgenic plant tissue (e.g., seeds), comprising expression of particular novel sequences. For example, expression of RcDGAT2 or RcPDAT1 in castor hydroxylase-expressing *Arabidopsis* lines resulted in substantially enhanced accumulation of hydroxy fatty acid (HFA) (e.g., to over 30%; a 50-70% increase in HFA accumulation) relative to the hydroxylase-only expressing parental lines. Further aspects provide methods to increase at least one of total lipid content, percent seed germination, and seed weight in transgenic plants, comprising expression of RcDGAT2 in castor hydroxylase-expressing plant lines. Yet further aspects provide methods for expressing and accumulating hydroxyl fatty acid in yeast (e.g., TAG biosynthesis from diricinolein), comprising expression of RcDGAT2 RcDGAT2 coding sequences in yeast.

40 Claims, 12 Drawing Sheets

OTHER PUBLICATIONS

Moreau et al., "Recent Studies of the Enzymic Synthesis of Ricinoleic Acid by Developing Castor Beans," Plant Physiology, 1981, pp. 672-676, vol. 67.

Sandager et al., "Storage Lipid Synthesis Is Non-essential in Yeast," The Journal of Biological Chemistry, Feb. 22, 2002, pp. 6478-6482, vol. 277, No. 8.

Smith et al., Evidence for cytochrome $b_5$ as an electron donor in ricinoleic acid biosynthesis in microsomal preparations from developing castor bean (*Ricinus communis* L.), Biochemical Journal, 1992, pp. 141-144, vol. 287.

Smith et al., "Heterologous expression of a fatty acid hydroxylase gene in developing seeds of *Arabidopsis thaliana*," Planta, 2003, pp. 507-516, vol. 217.

Van De Loo et al., "An oleate 12-hydroxylase from *Ricinus communis* L. is a fatty acyl desaturase homolog," The Proceedings of the National Academy of Sciences, Jul. 1995, pp. 6743-6747, vol. 92.

Zheng et al., "*Arabidopsis AtGPAT1*, a Member of the Membrane-Bound Glycerol-3-Phosphate Acyltransferase Gene Family, Is Essential for Tapetum Differentiation and Male Fertility," The Plant Cell, Aug. 2003, pp. 1872-1887, vol. 15.

U.S. Patent and Trademark Office, U.S. Appl. No. 10/861,616 (now Patent No. 7,195,901), non-final Office Action dated Apr. 6, 2006 (10 pages).

U.S. Patent and Trademark Office, U.S. Appl. No. 10/861,616 (now Patent No. 7,195,901), Amendment and Response to Non-Final Office Action dated Aug. 7, 2006 (12 pages).

He et al., "Cloning and Characterization of a cDNA Encoding Diacylglycerol Acyltransferase from Castor Bean," Lipids, 2004, pp. 311-318, vol. 39.

Database, EMBL CF981184, "yaa01g12.y1 RcSeed Ricinus communis cDNA 5' similar to TR:Q9SCZ7 Q9SCZ7 Hypothetical 37.4 KD Protein, mRNA sequence," Nov. 26, 2003.

* cited by examiner

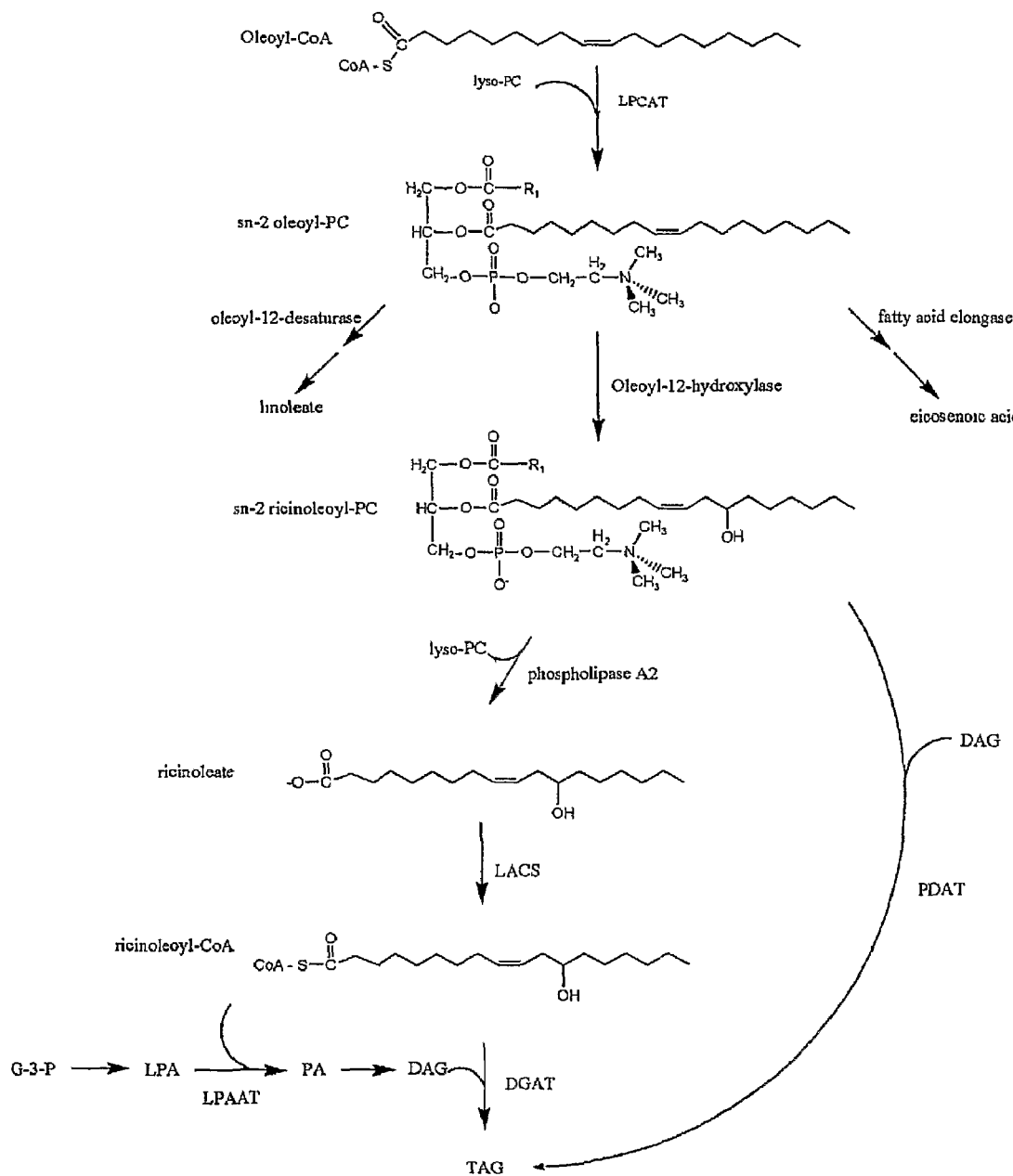

LPCAT- lyso-phosphatidylcholine acyltransferase
PC- phosphatidylcholine
DGAT- diacylglycerol acyltransferase
DAG- diacylglycerol
TAG- triacylglycerol
PDAT- phopholipid diacylglycerol acyltransferase
LACS- long chain acyl-CoA synthetase
CoA- coenzyme A
G-3-P- glycerol-3-phosphate
LPA- lysophosphatidic acid
PA- phosphatidic acid
LPAAT- lysophosphatidic acid acyltransferase

ENHANCEMENT OF HYDROXY FATTY ACID ACCUMULATION IN OILSEED PLANTS

CROSS-REFERENCE TO RELATED APPLICATIONS

This application is the U.S. National Phase of PCT/US2006/19829, filed May 22, 2006, which claims the benefit of priority to U.S. Provisional Application Ser. No. 60/683,170, filed 20 May 2005, which is incorporated by reference herein in its entirety.

FIELD OF THE INVENTION

Aspects of the present invention related generally to fatty acid accumulation in plants, and in particular aspects to hydroxy fatty acid accumulation in oilseed plants, and to novel compositions (e.g., *Ricinus communis* proteins and nucleic acid sequences) and broadly applicable genetic engineering methods for using same to enhance hydroxy fatty acid accumulation in plants, oil-producing plants, oilseed plants, plant seeds, and in diverse organisms such as yeast.

BACKGROUND

Overview. Plant biotechnologists have, because of the toxic byproducts found in castor bean (*Ricinus communis*), labored for years to produce a temperate oilseed crop that produces triacylglycerols rich in ricinoleic acid, which is the active component of castor oil. However, these labors, including the singular expression of the castor hydroxylase enzyme in *Arabidopsis*, or expression of FAH12 in transgenic tobacco or *Arabidopsis*, has not been sufficient to provide for high level accumulation of ricinoleate. There is, therefore, a pronounced need in the art for novel compositions and methods to enhance hydroxy fatty acid in plants (e.g., oilseed plants), and particularly in temperate oilseed crops (e.g., soybean or canola).

Limited Source of Ricinoleic acid. Ricinoleic acid (12-hydroxy-octadeca-cis-9-enoic acid: 18:1-OH) is a naturally-occurring compound with great value as a petrochemical replacement in a variety of industrial processes. Its derivatives are found in products such as dyes, lubricants, nylon, soaps, inks, adhesives, and bio-diesel[1]. Ricinoleic acid is produced in a very limited number of plant species, with the primary source being the seeds of castor bean (*Ricinus communis*). Ricinoleate makes up approximately 90% of the total castor seed fatty acids, primarily in the form of triacylglycerol (TAG). Castor oil is produced commercially from undomesticated plants grown in tropical climates[2]. Castor bean cannot be agriculturally optimized to accommodate demand, and it is therefore desirable to use a temperate oilseed crop, such as soybean or canola, as a platform for transgenic production of ricinoleate-rich oils.

Involvement of Oleoyl-12-Hydroxylase in the Natural Biosynthesis of Ricinoleic acid. Ricinoleic acid is formed by a hydroxylase enzyme that adds a hydroxy group to the twelfth carbon of oleic acid moieties esterified to the sn-2 position of phosphatidylcholine (PC)[3,4]. This reaction requires a cytochrome $b_5$ electron donor and molecular oxygen[5,6] and takes place in the endoplasmic reticulum (ER) membrane[5], which presumably allows for efficient channeling of ricinoleic acid into triacylglycerol (TAG) within the ER.

Prior Art Attempts to Increase Ricinoleic Acid Accumulation. There have been a number of prior art attempts to enhance accumulation of ricinoleic acid, including: (A) identification and expression of castor hydroxylase enzyme in FAH12 in transgenic tobacco or *Arabidopsis*; and (B) use of mutants deficient in FAD2 activity.

(A) Identification and Over-expression of Castor Hydroxylase Enzyme FAH12. Additionally, and based on shared biochemical characteristics (e.g., use of the same 18:1 substrate) between the castor hydroxylase and the broader family of fatty acyl desaturases[3,6], van de Loo et al.[7] screened a castor bean developing endosperm cDNA library for sequences homologous to the desaturases. A cDNA clone (named FAH12) was identified whose predicted protein shared approximately 67% amino acid identity with *Arabidopsis* FAD2, the enzyme that catalyzes the desaturation of oleate (18:1) to linoleate (18:2). Unfortunately, expression of FAH12 in transgenic tobacco caused the accumulation of ricinoleic acid, but only to very low levels[7].

Several laboratories have since attempted to identify and overcome the limitations to high-level production and accumulation of ricinoleic acid in plants. For example, *Arabidopsis* has shown great promise as a model system plant for studying castor seed oil biosynthesis, and seed-specific over-expression of FAH12 in *Arabidopsis* has resulted in higher ricinoleate levels than seen in tobacco. Unfortunately, however, the highest amount of hydroxy fatty acid accumulation in these *Arabidopsis* lines represented approximately 17% of total seed lipid[8,9], far below the ~90% found in castor bean and certainly less than would be necessary for practical use as a castor oil replacement.

When *Arabidopsis* was transformed with the hydroxylase cDNA, four novel hydroxy fatty acids were found to accumulate in the seeds (Broun and Somerville, 1997). In addition to ricinoleic acid accumulation, densipolic acid (12-hydroxy-octadec-cis-9,15 enoic acid: 18:2-OH), lesquerolic acid (14-hydroxy-eicos-cis-11-enoic acid: 20:1-OH), and auricolic acid (14-hydroxy-eicos-cis-11,17-enoic acid: 20:1-OH) accumulated to a small degree. These latter three fatty acids are not found to accumulate in castor bean seeds, but do accumulate in another hydroxy fatty acid producing species, the *Lesquerella* species. Members of the *Lesquerella* species each distribute their hydroxy fatty acids differently, but almost all species contain their hydroxy fatty acids as densipolic, lesquerolic, or auricolic acids instead of ricinoleic acid (Hayes et al., 1995). These three hydroxy fatty acids are also chemically valuable and the subspecies *Lesquerella fendleri* is grown in some areas as a seed oil crop (Abbott et al., 1997). It is thought that transgenic *Arabidopsis* lines metabolize ricinoleic acid similarly to the *Lesquerella* species since they both produce all four of these hydroxy fatty acids (Broun et al., 1998). A putative pathway suggests that the *Arabidopsis* fatty acyl desaturase, FAD3, is responsible for the desaturation of 18:1-OH to 18:2-OH, while fatty acyl elongase 1, FAE1, elongates both 18:1-OH and 18:2-OH to 20:1-OH and 20:2-OH, respectively (Broun and Somerville, 1997). Although the presence of these additional three hydroxy fatty acids contribute to the total seed hydroxy fatty acid in transgenic *Arabidopsis* lines, the total amount of accumulation has not breached the 20% hydroxy fatty acid mark.

(B) Use of Mutants Deficient in FAD2 Activity. When hydroxy fatty acids accumulate in *Arabidopsis* seeds, the amount of non-hydroxy 18:1 and 18:2 deviate considerably from wild-type amounts as summarized in Table 1:

TABLE 1

Typical fatty acid profile seen for wild-type Columbia seed (Col) versus seed transformed with the castor bean hydroxylase cDNA (CBH).

| Plant Name | 16:0 | 18:0 | 18:1 | 18:2 | 18:3 | 20:1 | 18:1-OH | 18:2-OH |
|---|---|---|---|---|---|---|---|---|
| CBH | 9.6% | 4.1% | 25.3% | 19.9% | 9.7% | 16.2% | 8.8% | 6.4% |
| Col | 8.5% | 3.1% | 17.1% | 31.3% | 21.6% | 18.1% | 0.0% | 0.0% |

The accumulation of 18:1 increases while 18:2 decreases. This divergence from wild-type levels has been speculated to be the result of inhibitory effects on the FAD2 desaturase by the hydroxylase, either directly or indirectly (Broun and Somerville, 1997). The inhibitory effects could hinder 18:1 from being used by either FAD2 or the hydroxylase, thus causing levels of 18:1 to increase past wild-type levels. Prior art attempts were therefore made to transform the hydroxylase cDNA into an *Arabidopsis* mutant deficient in FAD2 activity, thereby eliminating these inhibitory effects. However, when this experiment was performed, the levels of 18:1-OH did not increase significantly (Smith et al., 2003), indicating that the amount of 18:1 substrate is not a limiting factor for hydroxylase activity in the transformed *Arabidopsis* lines.

There is therefore, a pronounced need in the art for modifying plant oils, including provision of alternative crop sources for certain oils products and/or means to provide novel fatty acid compositions and/or accumulations for plant seed.

SUMMARY OF ASPECTS OF THE INVENTION

Particular aspects provide novel *Ricinus communis* cDNA clones, including six cloned sequences of: DGAT (RcDGAT1 and RcDGAT2); RcLPAT; LACS (RcLACS4), and PDAT (RcPDAT1A and RcPDAT1B). Additional aspects provide methods for substantially enhanced accumulation of hydroxy fatty acid (HFA) in transgenic plant tissue (e.g., seeds), comprising expression of particular novel sequences. For example, expression of RcDGAT2 or RcPDAT1 in castor hydroxylase-expressing *Arabidopsis* lines resulted in substantially enhanced accumulation of hydroxy fatty acid (HFA) (e.g., to over 30%; a 50-70% increase in HFA accumulation) relative to the hydroxylase-only expressing parental lines. Further aspects provide methods to increase at least one of total lipid content, percent seed germination, and seed weight in transgenic plants, comprising expression of RcDGAT2 in castor hydroxylase-expressing plant lines. Yet further aspects provide methods for expressing and accumulating hydroxyl fatty acid in yeast (e.g., TAG biosynthesis from diricinolein), comprising expression of RcDGAT2 coding sequences in yeast.

According to particular embodiments, DGAT2, RcPDAT1 and other functionally co-evolved enzymes of species with high levels of novel fatty acids (e.g., castor, *Crepis* sp., and *Euphorbia lagascae*, which produce hydroxy-, acetylenic-, and epoxy-fatty acids, respectively) have substantial utility to drive overexpression of the respective novel fatty acids, in a broad class or classes of plants and oilseeds that do not produce, or efficiently produce, the novel fatty acids (e.g., soybean, canola, etc.), and also in other diverse organisms such as yeast.

Particular aspects provide a novel isolated nucleic acid seqeuences (e.g., DNA sequences including SEQ ID NOS: 47-52) encoding a novel protein or polypeptide comprising or consisting of an amino acid sequence selected from the group consisting of SEQ ID NOS:54-59, respective biologically active portions thereof, and respective sequences having at least 85%, at least 90%, at least 95%, at least 97%, at least 98%, or at least 99% homology thereto. In certain aspects, the isolated coding sequence is selected from the group consisting of SEQ ID NOS:47-52 of *Ricinus communis*, and sequences having at least 85%, at least 90%, at least 95%, at least 98%, or at least 99% homology thereto.

Additional aspects provide a novel isolated protein or polypeptide, comprising or consisting of an amino acid sequence selected from the group consisting of SEQ ID NOS: 54-59 of *Ricinus communis*, respective biologically active portions thereof, and respective sequences having at least 85%, at least 90%, at least 95%, at least 97%, at least 98%, or at least 99% homology thereto. Certain embodiments provide for fusion proteins comprising these novel sequences.

Further aspects provide a transfected cell, comprising at least one expression vector having a DNA sequence that encodes upon expression a protein or polypeptide comprising or consisting of an amino acid sequence selected from the group consisting of SEQ ID NOS:54-59, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. Preferably, the DNA sequence comprises a sequence selected from the group consisting of SEQ ID NOS: 47-52, and sequences having at least 85%, at least 90%, at least 95%, at least 97%, at least 98%, or at least 99% homology thereto.

Additional embodiments provide a novel antibody or epitope-binding fragment thereof specific for an amino acid sequence selected from the group consisting of SEQ ID NOS: 54-59, respective epitope-bearing portions thereof, and respective sequences having at least 85%, at least 90%, at least 95%, at least 97%, at least 98%, or at least 99% homology thereto. Preferably, the antibody or epitope-binding fragment thereof is a monoclonal antibody or antigen-binding fragment thereof.

Yet additional embodiments provide a method to enhance hydroxy fatty acid accumulation in plants, plant tissue, or plant seeds, comprising introducing, into at least one plant cell or tissue, at least one expression vector having a DNA sequence that encodes upon expression for at least one *Ricinus communis* enzymatic activity selected from the group consisting of RcDGAT2, RcPDAT1, RcLPAT1, and RcLACS4, provided that recombinant RcDGAT2 is expressed, wherein enhanced hydroxy fatty acid accumulation in the plant cell or tissue is, at least in part, afforded. Preferably, the method further comprises recombinant expression of a *Ricinus communis* oleoyl-12-hydroxylase.

Further embodiments provide method to enhance hydroxy fatty acid accumulation in plants, plant tissue, or plant seeds, comprising introducing, into at least one plant cell or tissue, at least one expression vector having a DNA sequence that encodes upon expression for at least one protein or polypeptide comprising or consisting of an amino acid sequence selected from the group consisting of SEQ ID NOS:54-59, respective biologically active portions thereof, respective sequences having at least 85%, at least 90%, at least 95%, at least 97%, at least 98%, or at least 99% homology thereto, and respective fusion proteins thereof operatively associated with a heterologous polypeptide, wherein enhanced hydroxy fatty acid accumulation in the plant cell or tissue is, at least in part, afforded. Preferably, the at least one expression vector comprises a DNA sequence that encodes upon expression at least one protein or polypeptide comprising or consisting of an amino acid sequence selected from the group consisting of SEQ ID NOS:54 and 56, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. More preferably, the at least one expression vector comprises a DNA sequence that encodes upon expression a protein or polypeptide comprising or consisting of an amino acid sequence selected from the group consisting of SEQ ID NO:54, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. Preferably the method further comprises recombinant expression of an oleoyl-12-hydroxylase, and most preferably, a *Ricinus comminus* oleoyl-12-hydroxylase. In particular aspects, the *Ricinus communis* oleoyl-12-hydroxylase comprises or consists of an amino acid sequence selected from the group consisting of SEQ ID NO:62, respective biologically active portions thereof, respective sequences having at least 85%, at least 90%, at least 95%, at least 97%, at least 98%, or at least 99% homology thereto, and respective fusion proteins thereof operatively associated with a heterologous polypeptide.

Preferably, the DNA sequence of the at least one expression vector comprises a sequence selected from the group consisting of SEQ ID NOS:47 and 49, and sequences having at least 85%, at least 90%, at least 95%, at least 98%, or at least 99% homology thereto. Preferably, the DNA sequence comprises a sequence selected from the group consisting of SEQ ID NO:47, and sequences having at least 85%, at least 90%, at least 95%, at least 97%, at least 98%, or at least 99% homology thereto.

In particular aspects, the enhanced hydroxy fatty acid accumulation is in at least one form selected from the group consisting of fatty acids (FA), fatty acid esters, diacylglycerol (DAG), triaclyglcerol (TAG), and combinations thereof. Preferably, the enhanced hydroxy fatty acid accumulation is that of ricinoleic acid, and the enhanced ricinoleic acid accumulation is in at least one form selected from the group consisting of fatty acids (FA), fatty acid esters, diacylglycerol (DAG), triaclyglcerol (TAG), and combinations thereof.

In certain aspects the method for enhancing hydroxy fatty acid accumulation comprises recombinant expression of both: a protein or polypeptide comprising or consisting of an amino acid sequence selected from the group consisting of SEQ ID NO:54, respective biologically active portions thereof, respective sequences having at least 85%, at least 90%, at least 95%, at at least 97%, at least 98%, or at least 99% homology thereto, and respective fusion proteins thereof operatively associated with a heterologous polypeptide; and a protein or polypeptide comprising or consisting of an amino acid sequence selected from the group consisting of SEQ ID NO:56, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. Preferably, the method further comprises recombinant expression of a oleoyl-12-hydroxylase, and preferably, a *Ricinus communis* oleoyl-12-hydroxylase (e.g., an amino acid sequence selected from the group consisting of SEQ ID NO:62, respective biologically active portions thereof, respective sequences having at least 85%, at least 90%, at least 95%, at least 97%, at least 98%, or at least 99% homology thereto, and respective fusion proteins thereof operatively associated with a heterologous polypeptide).

Yet further embodiments provide a method to increase at least one of total lipid content, percent seed germination, and seed weight in transgenic plants, plant tissue, or plant seeds, comprising introducing into at least one plant cell or tissue, at least one expression vector having a DNA sequence that encodes upon expression for at least one protein or polypeptide comprising or consisting of an amino acid sequence selected from the group consisting of SEQ ID NOS:54-59, respective biologically active portions thereof, respective sequences having at least 85%, at least 90%, at least 95%, at least 97%, at least 98%, or at least 99% homology thereto, and respective fusion proteins thereof operatively associated with a heterologous polypeptide, wherein at least one of total lipid content, percent seed germination, and seed weight is, at least in part, afforded. Preferably, the method further comprises recombinant expression of a oleoyl-12-hydroxylase, and most preferably, a *Ricinus communis* oleoyl-12-hydroxylase.

BRIEF DESCRIPTION OF THE DRAWINGS

FIG. 1 shows, according to particular aspects of the present invention, a biochemical pathway illustrating alternate ways of incorporating ricinoleic acid into the triacylglycerol pool.

FIG. 10 shows, according to particular aspects of the present invention, the similarity between plant DGAT2 proteins: Barley DGAT2 (SEQ ID NO:63); Wheat DGAT2 (SEQ ID NO:64); Brassica napus DGAT2 (SEQ ID NO:65); Arabidopsis thaliana (At) DGAT2 (SEQ ID NO:60); Ricinus communis DGAT2 (SEQ ID NO:47); Maize DGAT2 (SEQ ID NO:66); and Rice DGAT2 (SEQ ID NO:67). The lightest gray-highlighted amino acids are identical residues exhibited in all species. The light-gray-highlighted residues are those showing identity in at least four plant species. The dark gray-highlighted show amino acid similarities. The darkest gray-highlighted residues show the stretch of 6 asparagine residues on the RcDGAT2 N terminus. The dark gray bar over the N termini show the region that AtDGAT2 and Brassica napus DGAT2 are lacking.

DETAILED DESCRIPTION OF THE INVENTION

Figure 2:
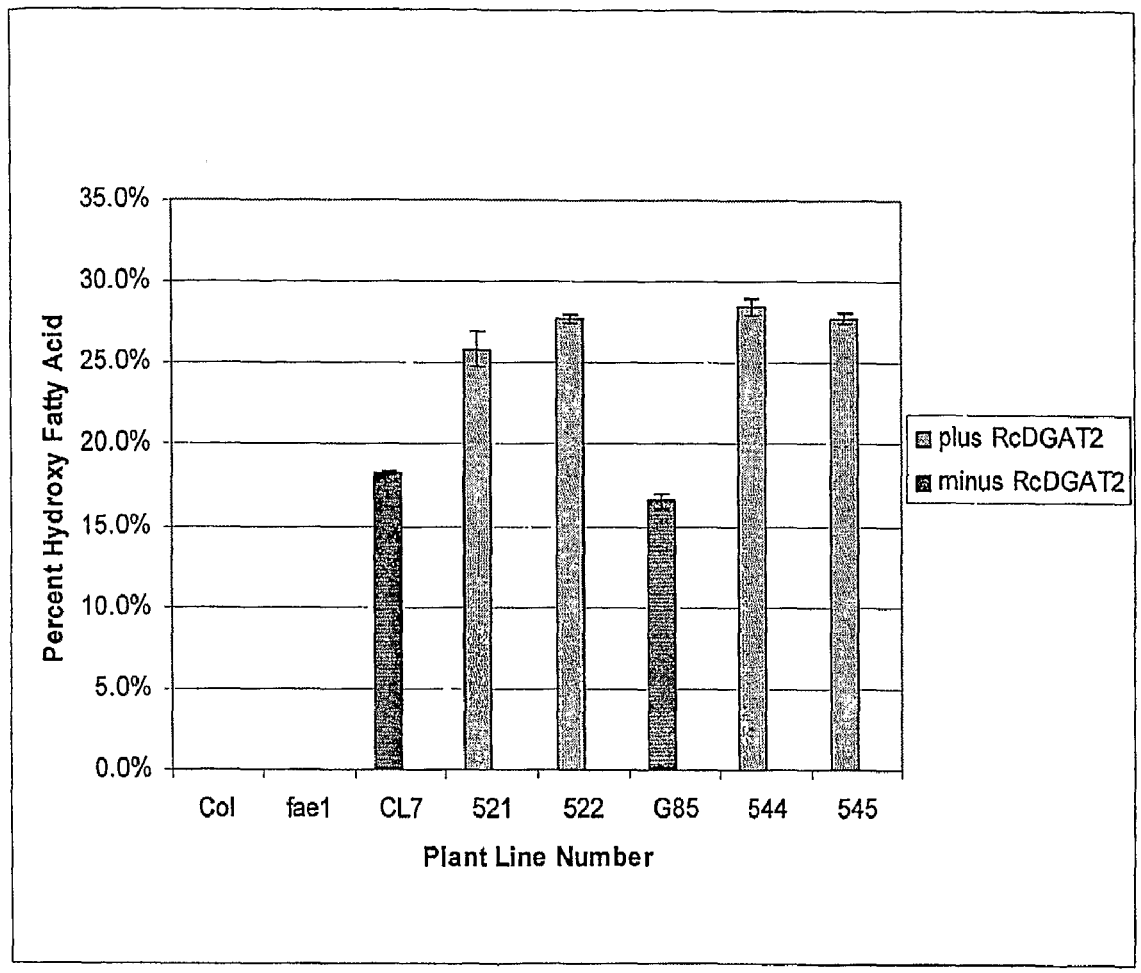
FIG. 2 shows, according to particular aspects of the present invention, a bar graph illustrating the difference in hydroxy fatty acid content of bulk seed from lines containing RcDGAT2 versus lines without RcDGAT2.

As discussed herein above under "Background," plant biotechnologists have, because of the toxic byproducts found in castor bean (Ricinus communis), labored for years to produce a temperate oilseed crop that produces triacylglycerols rich in ricinoleic acid, which is the active component of castor oil. However, these labors have not been sufficient to provide for high level accumulation of ricinloleate; until applicants' present invention, prior art attempts had failed to provide for accumulation of hydroxy fatty acids beyond 17% of the total fatty acid content in any plant seed, including transgenic Arabidopsis seeds.

According to particular aspects, applicants have conceived that a new/additional method of control (e.g., other than simply overexpression of hydroxylase), such as the involvement of other biosynthetic enzymes, is necessary to drive ricinoleic production and/or accumulation. In particular aspects, applicants' conception and inventive strategy is that the genes that encode such other enzymes have co-evolved with the hydroxylase to effectively channel ricinoleate away from membrane phospholipids and into seed triacylglycerols. Starting with applicants' conceptual premise that the hydroxylase has evolved to be efficient in ricinoleic acid production, applicants have further conceived that other enzymes in the castor bean lipid synthesis pathway have similarly evolved; for example that in developing castor seed, one or more steps in the pathway may be catalyzed by enzyme isoforms that display enhanced specificity for ricinoleate-containing substrates.

In particular aspects, therefore, applicants have identified and characterized particular host enzymes and regulatory factors in oil producing plants that mediate limiting steps in ricinoleate synthesis or storage in seed oils, and have replaced them with enzymes from castor having increased specificity for ricinoleate-containing substrates.

Art-Recognized Model System for Oil Producing Plants:

Particular exemplary experiments disclosed herein describe the effects of several castor bean lipid synthesis enzymes on seed oil production in Arabidopsis as a validated model system for oilseed plants generally. Arabidopsis thaliana is an ideal plant model for studying plant oil/seed oil biosynthesis because of its short life cycle, ease of growth, large seed yield, and its art-recognized similarity to other oil crop species, providing a validated model system that is applicable to other oil crop species. Arabidopsis is easily transformed with foreign DNA via Agrobacterium tumefaciens infection. This process, as described herein can be used for manipulating Arabidopsis to mimic the castor bean ricinoleic production pathway.

Therefore, according to additional aspects of the present invention, the instant inventive compositions and methods are effective in providing for accumulation of ricinoleic acid in Arabidopsis, have substantial utility in agriculturally amenable oil producing plants and oilseed crops generally, including but not limited to canola or soybean. At long last, applicants' inventive aspects will allow for effective global ricinoleic acid production, addressing the long-standing need for increased production of ricinoleic acid and its derivatives, and of compositions comprising same.

Identification of Novel and Useful Castor Bean Genes:

Applicants first identified castor bean genes having utility to enhance ricinoleic acid accumulation in transgenic oil producing plants (e.g., Arabidopsis seed oil). Applicants reasoned that the castor oil biosynthetic pathway may generally follow the Kennedy pathway[10]. The core reactions of this pathway are three successive acylation reactions of the hydroxyl groups of glycerol. In addition to these reactions, other less well-characterized accessory reactions may also drive ricinoleate accumulation into TAG.

Abbreviations used herein include the following:
  TAG, Triacylglycerol;
  DAG, Diacylglycerol;
  DGAT, Diacylglycerol Acyltransferase;
  PDAT, Phospholipid: Diacylglycerol Acyltransferase;
  LACS, Long Chain Acyl-CoA Synthetase;
  LPAAT, Lysophosphatidic Acid Acyltransferase;
  FAD2, Fatty Acyl Desaturase 2;
  FAEL, Fatty Acyl Elongase;
  PC, Phosphatidylcholine;
  CoA, Coenzyme A;
  DNA, Deoxyribonucleic Acid;
  RNA, Ribonucleic Acid;
  ORF, Open Reading Frame;
  ER, Endoplasmic Reticulum;
  Rc, Ricinus comniunis;
  At, Arabidopsis thaliana;
  TLC, Thin Layer Chromatography; and
  Ffa, free fatty acid.

With reference to FIG. 1, applicants reasoned that several routes of ricinoleoyl TAG biosynthesis may occur in castor bean developing seeds, each route using a different acyltransferase. Once ricinoleic acid is formed on PC, it might be incorporated into TAG in several ways. Ricinoleic acid may be cleaved from the glycerol backbone by phospholipase $A_2$, then activated by a long-chain acyl-CoA synthetase (LACS)[3], which can then be esterified to glycerol backbones (e.g. to produce TAG) by any of the three acyltransferases: glycerol-3-phosphate acyltransferase (GPAT)[11]; lysophosphatidic acid acyltransferase (LPAT)[12,13]; and diacylglycerol acyltransferase (DGAT)[14] (FIG. 1). Alternatively, ricinoleic acid may be directly transferred from the sn-2 position of PC to the sn-3 position of DAG via phospholipid: diacylglycerol acyltransferase (PDAT)[5]. In these pathways, applicants reasoned that either DGAT or PDAT, respectively, might exhibit the largest level of control in regulating TAG biosynthesis. Additionally, a long chain acyl-CoA synthetase ("LACS") enzyme, for example, may also exhibit levels of control in ricinoleic acid accumulation.

In particular inventive aspects, representative full-length clones for several different steps of this pathway were identified and cloned from a developing castor seed cDNA library. The working EXAMPLES hereunder disclose and describe the effects of expression of these enzymes on the seed lipid composition of hydroxy fatty acid-producing *Arabidopsis* plants, and identify enzymes having a key role in determining the fate of ricinoleic acid, and having substantial utility to provide for higher hydroxy fatty acid (HFA) accumulation in plants, including oil-producing plants and transgenic plants (e.g., *Arabidopsis* seeds, and seeds of other oil-producing plants, including but not limited to soybean, canola, etc).

Specifically, six novel cDNAs (SEQ ID NOS:47-52; see also TABLE 3 herein below) were found by screening a castor bean developing seed cDNA library using degenerate primers based on conserved amino acid sequences. In the cDNA library, two novel DGAT cDNA sequences were found, DGAT1 and DGAT2, two novel PDAT cDNA sequences were found, PDAT1A and PDAT1B, and one novel LACS cDNA, LACS4. Several novel LPAAT cDNA sequences were found, and LPAAT1 was analyzed in detail.

The six cDNAs (i.e., the acyltransferases mentioned above, DGAT and PDAT, along with a LACS enzyme) were transformed (in the context of expression vectors) into hydroxyfatty-acid-producing *Arabidopsis* plants. Additionally, a cDNA belonging to another class of acyltransferases, the lysophosphatidic acid acyltransferases (LPAAT), was included. The LPAAT class may have an indirect function in ricinoleic acid accumulation by allowing for its accumulation in DAG (FIG. 1) and is a worthwhile candidate in this study.

Of these six cDNAs, both RcDGAT2 and RcPDAT1A allowed for promising increases in hydroxy fatty acid content. Both RcDGAT2 and RcPDAT1A expression was pursued in more detail (see Examples below) both in vivo and in vitro. *Arabidopsis* transformants expressing RcDGAT2 along with the castor bean hydroxylase gene were found increase seed ricinoleate levels by 70% (e.g., accumulating hydroxy fatty levels up to 30%). Specifically, in repeated experiments, the triacylglycerol (TAG) fraction of *Arabidopsis* transformants expressing RcDGAT2 and FAH12 (castor hydroxylase; U22378.1) contained significantly higher levels of hydroxy fatty acid (HFA) levels than the parental hydroxylase lines lacking recombinant RcDGAT2 (see EXAMPLE 5, Table 7A below). Comparable results were obtained for RcPDAT1A expressing lines (see EXAMPLE 5 Table 7B below). The HFA content in these lines is by far the highest reported in the literature. Significantly, this enhanced accumulation was not found when the *Arabidopsis* DGAT2 (AtDGAT2) was overexpressed in the same lines.

Additionally, biochemical analyses of the substrate preferences of yeast-expressed AtDGAT2 and RcDGAT2 in yeast microsomes were consistent with the in planta data; namely, yeast-expressed RcDGAT2 was found to work almost six times better with diricinolein as the DAG substrate than diolein, whereas the activity of AtDGAT2 was found to be minimal, being close to the level of the control. These data collectively indicate that the castor bean RcDGAT2 is likely not only a major component in providing for high levels of hydroxy fatty acid found in castor bean seeds, but further establishes that compared to AtDGAT2, RcDGAT2 more effectively channels ricinoleate into castor seed triacylglycerols, and establishes this enzyme as a component having substantial utility for ricinoleate metabolic engineering programs in transgenic plants (including heterologous transgenic plants), including oil-producing plants (e.g., *Arabidopsis* seeds, and seeds of other oil-producing plants, including but not limited to soybean, canola, etc). The present results are broadly generalizable, because of the broad commonality of the relevenat biosynthetic pathway in oil producing plants generally, and particularly in oil seed plants generally.

Collectively the data disclosed herein in the working EXAMPLES, confirm aspects of applicants' original conception that the previous limitations to ricinoleate accumulation in developing oilseeds are indeed due to the lack of compatible TAG biosynthetic enzymatic machinery, and that particular enzyme catalyzed steps, such as that mediated by DGAT, are bottlenecks for HFA production in many oil producing plants. Therefore, according to particular aspects, in developing castor seed, one or more steps in the pathway are catalyzed by enzyme isoforms that display enhanced specificity for ricinoleate-containing substrates, affording novel compositions and methods for removing such bottlenecks in oil producing plants generally. For example, transgenic expression of RcDGAT2 and/or RcPDAT1A, as disclosed herein, removes major bottlenecks in the process of HFA production in plant seeds in the oil seed plant model system *Arabadopsis*, and also in yeast, and support broad implementation of the invention compositions and methods to encompass a variety of plant Overview of General Methods:

Particular embodiments relate generally to enzymes involved in the biosynthesis of hydroxyl fatty acids (e.g., ricinoleic acid (12-hydroxy-octadeca-cis-9-enoic acid: 18:1-OH) and DAG and TAG comprising same). Particular aspects provide novel DNA constructs having substantial utility for expression of *Ricinus communis* nucleic acids (e.g., cDNAs, mRNA, genomic) that encode DGAT (RcDGAT1 and RcDGAT2); RcLPAT; LACS (RcLACS4), and PDAT (RcPDAT1A and RcPDAT1B), and that can be used for expression of these enzymes in plant cells, an cell of other organisms. The novel nucleic acids have substantial utility for enhancing the accumulation of Ricinoleic acid (12-hydroxyoctadeca-cis-9-enoic acid: 18:1-OH) containing fatty acids (e.g., DAG and TAG).

Exemplary constructs contain a DNA sequence encoding the plant DGAT (RcDGAT1 and RcDGAT2); RcLPAT; LACS (RcLACS4), and PDAT (RcPDAT1A and RcPDAT1B) of interest under the control of regulatory elements capable of preferentially directing the expression of the plant DGAT (RcDGAT1 and RcDGAT2); RcLPAT; LACS (RcLACS4), and PDAT (RcPDAT1A and RcPDAT1B) in plant seed tissue, as compared with other plant tissues, when such a construct is expressed in a transgenic plant. Additional aspects provide methods of using a DNA sequence encoding a plant DGAT (RcDGAT1 and RcDGAT2); RcLPAT; LACS (RcLACS4), and PDAT (RcPDAT1A and RcPDAT1B) for modification of the accumulation of hydroxy fatty acids (e.g., ricinoleic acid) produced in a plant seed cell. Plant DGAT (RcDGAT1 and RcDGAT2); RcLPAT; LACS (RcLACS4), and PDAT (RcPDAT1A and RcPDAT1B) sequences exemplified herein include those of castor bean (*Ricinus communis*), and sequences related thereto as herein described. Transgenic plants having increased levels of hydroxy fatty acids (e.g., ricinoleic acid fatty acids) in their seeds as the result of expression of these nucleic acid sequences are also provided.

Plant DGAT (RcDGAT1 and RcDGAT2); RcLPAT; LACS (RcLACS4), and PDAT (RcPDAT1A and RcPDAT1B) DNA sequences of this invention encode for respective amino acids, in the form of proteins, polypeptides or peptide fragments, which amino acids demonstrate the ability to enhance accumulation (levels) of hydroxy fatty acids (e.g., ricinoleic acid fatty acids) under plant enzyme reactive conditions; that is under any necessary conditions are available in an environment (i.e., such factors as temperature, pH, lack of inhibiting substances) which will permit the enzyme to function.

One skilled in the art will readily recognize that antibody preparations, nucleic acid probes (DNA and RNA) and the like may be prepared and used to screen and recover "homologous" or "related" DGAT; RcLPAT; LACS, and PDAT nucleic acids and proteins from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful for gene isolation. For detection, the antibody is labeled using radioactivity or any one of a variety of second antibody/enzyme conjugate systems that are commercially available, and well-known in the art.

Homologous sequences are found when there is an identity of sequence and may be determined upon comparison of sequence information, nucleic acid or amino acid, or through hybridization reactions between a known DGAT (RcDGAT1 and RcDGAT2); RcLPAT; LACS (RcLACS4), and PDAT (RcPDAT1A and RcPDAT1B) and a candidate source. Conservative changes (see in more detail below), such as Glu/Asp, Val/Ile, Ser/Thr, Arg/Lys and Gln/Asn may also be considered in determining sequence homology.

Typically, a lengthy nucleic acid sequence may show as little as 50-60%, 60%-70%, 80% to 80% sequence identity, and more preferably at least about 70% or about 80% sequence identity, between the target sequence and the given plant DGAT (RcDGAT1 and RcDGAT2); RcLPAT; LACS (RcLACS4), and PDAT (RcPDAT1A and RcPDAT1B) of interest excluding any deletions which may be present, and still be considered related. Amino acid sequences are considered homologous by as little as 25% sequence identity between the two complete mature proteins. (see generally, Doolittle, R. F., OF URFS and ORFS (University Science Books, California, 1986).

To obtain additional DGAT (RcDGAT1 and RcDGAT2); RcLPAT; LACS (RcLACS4), and PDAT (RcPDAT1A and RcPDAT1B), a genomic or other appropriate library prepared from the candidate plant source of interest is probed with conserved sequences from one or more DGAT (RcDGAT1 and RcDGAT2); RcLPAT; LACS (RcLACS4), and PDAT (RcPDAT1A and RcPDAT1B) to identify homologously related sequences. Positive clones are then analyzed by restriction enzyme digestion and/or sequencing. When a genomic library is used, one or more sequences may be identified providing both the coding region, as well as the transcriptional regulatory elements of the thioesterase gene from such plant source. Probes can also be considerably shorter than the entire sequence. Oligonucleotides (see below in more detail) may be used, for example, but should be at least about 10, preferably at least about 15, at least about 18, at least about 19, at least about 20, at least about 25, at least about 50, or at least about 100, and preferably at least about 19 or about 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. When longer nucleic acid fragments are employed (>100 bp) as probes, especially when using complete or large cDNA sequences, moderately high stringencies (for example using 50% formamide at 37° C. with minimal washing) can still be used for screening to obtain signal from the target sample with 20-50% deviation, i.e., homologous sequences.

Not only can DGAT (RcDGAT1 and RcDGAT2); RcLPAT; LACS (RcLACS4), and PDAT (RcPDAT1A and RcPDAT1B) sequences such as shown herein be used to identify homologous additional DGAT (RcDGAT1 and RcDGAT2); RcLPAT; LACS (RcLACS4), and PDAT (RcPDAT1A and RcPDAT1B) sequences, but the resulting sequences obtained therefrom may also provide a further method to obtain plant additional DGAT (RcDGAT1 and RcDGAT2); RcLPAT; LACS (RcLACS4), and PDAT (RcPDAT1A and RcPDAT1B) from other plant sources. In particular, PCR may be a useful technique to obtain related plant additional DGAT (RcDGAT1 and RcDGAT2); RcLPAT; LACS (RcLACS4), and PDAT (RcPDAT1A and RcPDAT1B) from sequence data provided herein. One skilled in the art will be able to design oligonucleotide probes based upon sequence comparisons or regions of typically highly conserved sequence.

Once the nucleic acid sequence is obtained, the transcription, or transcription and translation (expression), of the plant additional DGAT (RcDGAT1 and RcDGAT2); RcLPAT; LACS (RcLACS4), and PDAT (RcPDAT1A and RcPDAT1B) in a host cell is desired, to produce a ready source of the enzyme and/or modify the composition of fatty acids and/or diglycerides and/or triglycerides found therein. Other useful applications may be found when the host cell is a plant host cell, in vitro and in vivo. Additionally, as disclosed herein, yeast may be used. For example, by increasing the amount of one or more DGAT (RcDGAT1 and RcDGAT2); RcLPAT; LACS (RcLACS4), and PDAT (RcPDAT1A and RcPDAT1B) enzymes available to the plant biosynthetic complex, an increased percentage of ricinoleic fatty acids may be provided. In a like manner, for some applications, by decreasing the amount of particular enzymes (e.g., desaturase enzymes and/or fatty acyl elongases) available to the plant, in conjunction with an increase of the amount of one or more DGAT (RcDGAT1 and RcDGAT2); RcLPAT; LACS (RcLACS4), and PDAT (RcPDAT1A and RcPDAT1B) enzymes available, a substantial increase in the hydroxy fatty acids may be found.

The nucleic acid sequences which encode plant DGAT (RcDGAT1 and RcDGAT2); RcLPAT; LACS (RcLACS4), and PDAT (RcPDAT1A and RcPDAT1B) enzymes may be used in various constructs, for example, as probes to obtain further sequences. Alternatively, these sequences may be used in conjunction with appropriate regulatory sequences to increase levels of the respective DGAT (RcDGAT1 and RcDGAT2); RcLPAT; LACS (RcLACS4), and PDAT (RcPDAT1A and RcPDAT1B) enzymes of interest in a host cell for recovery or study of the enzyme in vitro or in vivo or to decrease levels or activities of other enzymes of interest for some applications when the host cell is a plant entity, including plant cells, plant parts (including but not limited to seeds, cuttings or tissues) and plants.

A nucleic acid sequence encoding a novel plant DGAT (RcDGAT1 and RcDGAT2); RcLPAT; LACS (RcLACS4), and PDAT (RcPDAT1A and RcPDAT1B) enzyme disclosed herein may include genomic, cDNA or mRNA sequence. "Encoding" means that the sequence corresponds to a particular amino acid sequence either in a sense or anti-sense orientation. By "extrachromosomal" is meant that the sequence is outside of the plant genome of which it is naturally associated. "Recombinant" means that the sequence contains a genetically engineered modification through manipulation via mutagenesis, restriction enzymes, and the like. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the "mature" sequence. The use of the precursor plant DGAT (RcDGAT1 and RcDGAT2); RcLPAT; LACS (RcLACS4), and PDAT (RcPDAT1A and RcPDAT1B) DNA sequence is preferred in plant cell expression cassettes. Other transit peptide sequences, such as a transit peptide of seed ACP, may be employed to translocate the plant DGAT (RcDGAT1 and RcDGAT2); RcLPAT; LACS (RcLACS4), and PDAT (RcPDAT1A and RcPDAT1B) enzymes of this invention to various organelles of interest. Likewise, once a given plant DGAT (RcDGAT1 and RcDGAT2); RcLPAT; LACS (RcLACS4), and PDAT (RcPDAT1A and RcPDAT1B) transit peptide is obtained, it may be used to translocate sequences other than its native coding region.

The complete genomic sequence of the plant DGAT (RcDGAT1 and RcDGAT2); RcLPAT; LACS (RcLACS4), and PDAT (RcPDAT1A and RcPDAT1B) enzymes may be obtained by the screening of a genomic library with a probe, such as a cDNA probe, and isolating those sequences which, for example, regulate expression in seed tissue. In this manner, the transcription and translation initiation regions, introns, and/or transcript termination regions of the plant DGAT (RcDGAT1 and RcDGAT2); RcLPAT; LACS (RcLACS4), and PDAT (RcPDAT1A and RcPDAT1B) enzymes may be obtained for use in a variety of DNA constructs, with or without the DGAT (RcDGAT1 and RcDGAT2); RcLPAT; LACS (RcLACS4), and PDAT (RcPDAT1A and RcPDAT1B) enzymes structural gene. Thus, nucleic acid sequences corresponding to the plant DGAT (RcDGAT1 and RcDGAT2); RcLPAT; LACS (RcLACS4), and PDAT (RcPDAT1A and RcPDAT1B) enzymes of this invention may also provide signal sequences useful to direct transport to a cellular organelle (e.g., into a plastid), 5' upstream non-coding regulatory regions (promoters) having useful tissue and timing profiles, 3' downstream non-coding regulatory region useful as transcriptional and translational regulatory regions and may lend insight into other features of the gene.

Once the desired plant DGAT (RcDGAT1 and RcDGAT2); RcLPAT; LACS (RcLACS4), and PDAT (RcPDAT1A and RcPDAT1B) nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding an inventive plant DGAT (RcDGAT1 and RcDGAT2); RcLPAT; LACS (RcLACS4), and PDAT (RcPDAT1A and RcPDAT1B) may be combined with other non-native, or "heterologous", sequences in a variety of ways. By "heterologous" sequences is meant any sequence which is not naturally found joined to the plant DGAT (RcDGAT1 and RcDGAT2); RcLPAT; LACS (RcLACS4), and PDAT (RcPDAT1A and RcPDAT1B), including, for example, combinations of nucleic acid sequences from the same plant which are not naturally found joined together.

The DNA sequence encoding an inventive plant DGAT (RcDGAT1 and RcDGAT2); RcLPAT; LACS (RcLACS4), and PDAT (RcPDAT1A and RcPDAT1B) may be employed in conjunction with all or part of the gene sequences normally associated with the DGAT (RcDGAT1 and RcDGAT2); RcLPAT; LACS (RcLACS4), and PDAT (RcPDAT1A and RcPDAT1B). In its component parts, for example, a DNA DGAT (RcDGAT1 and RcDGAT2); RcLPAT; LACS (RcLACS4), and PDAT (RcPDAT1A and RcPDAT1B) encoding sequence is combined in a DNA construct having, in the 5' to 3' direction of transcription, a transcription initiation control region capable of promoting transcription and translation in a host cell, the DNA sequence encoding one or more plant DGAT (RcDGAT1 and RcDGAT2); RcLPAT; LACS (RcLACS4), and PDAT (RcPDAT1A and RcPDAT1B), and a transcription and translation termination region.

Potential host cells include both prokaryotic and eukaryotic cells (e.g., yeast, etc.). A host cell may be unicellular or found in a multicellar differentiated or undifferentiated organism depending upon the intended use. Inventive cells may be distinguished by having a plant DGAT (RcDGAT1 and RcDGAT2); RcLPAT; LACS (RcLACS4), and PDAT (RcPDAT1A and RcPDAT1B) foreign to the wild-type cell present therein, for example, by having a recombinant nucleic acid construct encoding a plant DGAT (RcDGAT1 and RcDGAT2); RcLPAT; LACS (RcLACS4), and PDAT (RCPDAT1A and RcPDAT1B) therein.

Depending upon the host, the regulatory regions may vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

Generally, the constructs will involve regulatory regions functional in plants, plant tissues (e.g., seed tissue) or other organisms (e.g., yeast) which provide for modified production of plant DGAT (RcDGAT1 and RcDGAT2); RcLPAT; LACS (RcLACS4), and PDAT (RcPDAT1A and RcPDAT1B), and possibly, modification of the fatty acid composition and/or accumulation (level). The open reading frame, coding for the plant DGAT (RcDGAT1 and RcDGAT2); RcLPAT; LACS (RcLACS4), and PDAT (RcPDAT1A and RcPDAT1B) or functional fragments thereof will be joined at its 5' end to a transcription initiation regulatory region such as, for example, the wild-type sequence naturally found 5' upstream to the respective DGAT (RCDGAT1 and RcDGAT2); RcLPAT; LACS (RcLACS4), and PDAT (RcPDAT1A and RcPDAT1B) structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine synthases, or with napin, ACP promoters and the like. The transcription/translation initiation regions corresponding to such structural genes are found immediately 5' upstream to the respective start codons. In embodiments wherein the expression of one or more of the DGAT (RcDGAT1 and RcDGAT2); RcLPAT; LACS (RcLACS4), and PDAT (RcPDAT1A and RcPDAT1B) proteins is desired in a plant host, the use of all or part of the complete plant DGAT (RcDGAT1 and RcDGAT2); RcLPAT; LACS (RcLACS4), and PDAT (RcPDAT1A and RcPDAT1B) gene is desired; namely all or part of the 5' upstream non-coding regions (promoter) together with the structural gene sequence and 3' downstream non-coding regions may be employed. Alternatively, if a different promoter is desired, such as a promoter native to the plant host of interest or a modified promoter, i.e., having transcription initiation regions derived from one gene source and translation initiation regions derived from a different gene source, including the sequences encoding the DGAT (RcDGAT1 and RcDGAT2); RcLPAT; LACS (RcLACS4), and PDAT (RcPDAT1A and RcPDAT1B) of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto," which references are hereby incorporated by reference. Transcription initiation regions which are preferentially expressed in seed tissue, i.e., which are undetectable in other plant parts, are considered desirable for fatty acid modifications and/or accumulation in order to minimize any disruptive or adverse effects of the gene product.

Regulatory transcript termination regions may be provided in DNA constructs of this invention as well. Transcript termination regions may be provided by the DNA sequence encoding the plant DGAT (RcDGAT1 and RcDGAT2); RcLPAT; LACS (RcLACS4), and PDAT (RcPDAT1A and RcPDAT1B) or a convenient transcription termination region derived from a different gene source, for example, the transcript termination region which is naturally associated with the transcript initiation region. In particular embodiments (e.g., where the transcript termination region is from a different gene source), it will contain at least about 0.5 kb, preferably about 1-3 kb of sequence 3' to the structural gene from which the termination region is derived.

Plant expression or transcription constructs having a plant DGAT (RcDGAT1 and RcDGAT2); RcLPAT; LACS (RcLACS4), and PDAT (RcPDAT1A and RcPDAT1B) as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, *Cuphea*, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to *Agrobacterium* infection may be successfully transformed via tripartite or binary vector methods of *Agrobacterium*-mediated transformation. Additionally, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*, Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. Included with the expression construct and the T-DNA will be one or more markers, which allow for selection of transformed *Agrobacterium* and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

Once a transgenic plant is obtained which is capable of producing seed having a modified fatty acid composition and/or accumulation level, traditional plant breeding techniques, including methods of mutagensis, may be employed to further manipulate the fatty acid composition. Alternatively, additional foreign fatty acid modifying DNA sequence may be introduced via genetic engineering to further manipulate the fatty acid composition. It is noted that the method of transformation is not critical to this invention. However, the use of genetic engineering plant transformation methods (e.g., to insert a single desired DNA sequence) is critical. Heretofore, the ability to modify the fatty acid composition of plant oils was limited to the introduction of traits that could be sexually transferred during plant crosses or viable traits generated through mutagensis. Through the use of genetic engineering techniques which permit the introduction of inter-species genetic information and the means to regulate the tissue-specific expression of endogenous genes, a new method is available for the production of plant seed oils with modified fatty acid compositions and/or accumulations using the inventive DGAT (RCDGAT1 and RcDGAT2); RcLPAT; LACS (RcLACS4), and PDAT (RcPDAT1A and RCPDAT1B) nucleic acids and proteins. In addition, there is the potential for the development of novel plant seed oils upon application of the tools described herein.

One may choose to provide for the transcription or transcription and translation of one or more other sequences of interest in concert with the expression of a plant DGAT (RcDGAT1 and RcDGAT2); RcLPAT; LACS (RcLACS4), and PDAT (RcPDAT1A and RcPDAT1B) in a plant host cell. In particular, the reduced expression of one or more Fatty Acyl Desaturases (e.g., Fatty Acyl Desaturase 2; FAD2) and/or reduced expression of one or more Fatty Acyl Elongases, in combination with expression of a plant DGAT (RcDGAT1 and RcDGAT2); RcLPAT; LACS (RcLACS4), and PDAT (RcPDAT1A and RcPDAT1B) may be preferred in some applications.

For providing a plant transformed for the combined effect of more than one nucleic acid sequence of interest, typically, but not necessarily a separate nucleic acid construct will be provided for each. The constructs, as described above, contain transcriptional or transcriptional or transcriptional and translational regulatory control regions. One skilled in the art will be able to determine regulatory sequences to provide for a desired timing and tissue specificity appropriate to the final product in accord with the above principles (e.g., respective expression or anti-sense constructs). When two or more constructs are to be employed, whether they are both related to the same fatty acid modifying sequence or a different fatty acid modifying sequence, it may be desired that different regulatory sequences be employed in each cassette to reduce spontaneous homologous recombination between sequences. The constructs may be introduced into the host cells by the same or different methods, including the introduction of such a trait by crossing transgenic plants via traditional plant breeding methods, so long as the resulting product is a plant having both characteristics integrated into its genome.

An inventive plant DGAT (RcDGAT1 and RcDGAT2); RcLPAT; LACS (RcLACS4), and PDAT (RcPDAT1A and RcPDAT1B) includes any sequence of amino acids, such as a protein, polypeptide, or peptide fragment, obtainable from a plant source which is capable of catalyzing the respective biological activity in a plant host cell, i.e., in vivo, or in a plant cell-like environment, i.e., in vitro. "A plant cell-like environment" means that any necessary conditions are available in an environment (i.e., such factors as temperatures, pH, lack of inhibiting substances) which will permit the enzyme to function.

By decreasing the amount of one or more Fatty Acyl Desaturases (e.g., Fatty Acyl Desaturase 2; FAD2) and/or one or more Fatty Acyl Elongases, an increased percentage of hydroxy fatty acids may be provided. Using anti-sense, transwitch, ribozyme or some other expression reducing technology (e.g., mutants), a decrease in the amount of one or more Fatty Acyl Desaturases (e.g., Fatty Acyl Desaturase 2; FAD2) and/or one or more Fatty Acyl Elongases available to the plant cell is produced, resulting in a higher hydroxy fatty acid percentages.

Oils with increased percentages of hydroxyl fatty acids (e.g., ricinoleic fatty acids) are desired. By manipulation of various aspects of the DNA constructs (e.g., choice of promoters, number of copies, etc.) and traditional breeding methods, one skilled in the art may achieve even greater levels of hydroxy fatty acid percentages in rapeseed and other plant species.

Biologically Active Variants

Variants of plant DGAT (RcDGAT1 and RcDGAT2); RcLPAT; LACS (RcLACS4), and PDAT (RcPDAT1A and RcPDAT1B) enzymes have substantial utility in various inventive aspects. Variants can be naturally or non-naturally occurring. Naturally occurring variants are found in plants or other species and comprise amino acid sequences which are substantially identical to the amino acid sequences shown in SEQ ID NOS:54-59, and include natural sequence polymorphisms. Species homologs of the protein can be obtained using subgenomic polynucleotides of the invention, as described herein, to make suitable probes or primers for screening cDNA expression libraries from other plant species, or organisms, identifying cDNAs which encode homologs of the protein, and expressing the cDNAs as is known in the art.

Non-naturally occurring variants which retain substantially the same biological activities as naturally occurring DGAT (RcDGAT1 and RcDGAT2); RcLPAT; LACS (RcLACS4), and PDAT (RcPDAT1A and RcPDAT1B) protein variants, are also included here. Preferably, naturally or non-naturally occurring variants have amino acid sequences which are at least 75%, at least 85%, at least 90%, or at least 95% identical to the amino acid sequences shown in SEQ ID NOS:54-59. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243: 3552-59 (1969) and adopted at 37 C.F.R. §§1.821-1.822, abbreviations for amino acid residues are shown in Table A:

TABLE A

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

Guidance in determining which amino acid residues can be substituted, inserted, or deleted without abolishing biological or immunological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p. 224).

Such substitutions may be made in accordance with those set forth in TABLE B as follows:

TABLE B

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative (or non-conservative) substitutions.

Variants of the DGAT (RcDGAT1 and RcDGAT2); RcLPAT; LACS (RcLACS4), and PDAT (RcPDAT1A and RcPDAT1B) disclosed herein (e.g., variants of SEQ ID NOS: 54-59) include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins (Mark et al., U.S. Pat. No. 4,959,314).

Preferably, amino acid changes in the DGAT (RcDGAT1 and RcDGAT2); RcLPAT; LACS (RcLACS4), and PDAT (RcPDAT1A and RcPDAT1B) variants (e.g., in the variants of SEQ ID NOS:54-59) are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of Herstatin and/or RBD Int8 polypeptide protein or polypeptide variants are of the same type as a protein comprising the amino acid sequence encoded by the nucleotide sequences shown in SEQ ID NO:1 or 2, although the properties and functions of variants can differ in degree.

DGAT (RcDGAT1 and RcDGAT2); RcLPAT; LACS (RcLACS4), and PDAT (RcPDAT1A and RcPDAT1B) polypeptides variants (e.g., variants of SEQ ID NOS:54-59) include glycosylated forms, aggregative conjugates with other molecules, and covalent conjugates with unrelated chemical moieties (e.g., pegylated molecules). Herstatin and/or RBD Int8 polypeptide variants also include allelic variants (e.g., polymorphisms), species variants, and muteins. Truncations or deletions of regions which do not preclude functional activity of the proteins are also variants. Covalent variants can be prepared by linking functionalities to groups which are found in the amino acid chain or at the N- or C-terminal residue, as is known in the art.

It will be recognized in the art that some amino acid sequence of the DGAT (RcDGAT1 and RcDGAT2); RcLPAT; LACS (RcLACS4), and PDAT (RcPDAT1A and RcPDAT1B) polypeptides (e.g., SEQ ID NOS:54-59) of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors (Ostade et al., Nature 361:266-268, 1993). Thus, the DGAT (RcDGAT1 and RcDGAT2); RcLPAT; LACS (RcLACS4), and PDAT (RcPDAT1A and RcPDAT1B) polypeptides (e.g., SEQ ID NOS:54-59) of the present inventive aspects may include one or more amino acid substitutions, deletions or additions, either from natural mutations or human manipulation.

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing formulations.

Amino acids in the inventive DGAT (RcDGAT1 and RcDGAT2); RcLPAT; LACS (RcLACS4), and PDAT (RcPDAT1A and RcPDAT1B) polypeptides that are essential for function can be identified by methods known in the art, such as site-directed mutagenesis or alanine-scanning mutagenesis (Cunningham and Wells, Science 244:1081-1085, 1989). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., J. Mol. Biol. 224:899-904, 1992 and de Vos et al. Science 255:306-312, 1992).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given Herstatin and/or RBD Int8 polypeptide will not be more than 50, 40, 30, 25, 20, 15, 10, 5 or 3.

In addition, pegylation of DGAT (RcDGAT1 and RcDGAT2); RcLPAT; LACS (RcLACS4), and PDAT (RcPDAT1A and RcPDAT1B) polypeptides (e.g., of SEQ ID NOS:54-59) and/or muteins is expected to provide such improved properties as increased half-life, solubility, and protease resistance. Pegylation is well known in the art.

Functional DGAT (RcDGAT1 and RcDGAT2); RcLPAT; LACS (RcLACS4), and PDAT (RcPDAT1A and RcPDAT1B) polypeptides (e.g., of SEQ ID NOS:54-59), and functional variants thereof, are those proteins that display one or more of the biological activities of their respective DGAT (RcDGAT1 and RcDGAT2); RcLPAT; LACS (RcLACS4), and PDAT (RcPDAT1A and RcPDAT1B) polypeptides (e.g., of SEQ ID NOS:54-59). In particular aspects, such functional variants and portions thereof have at least 85%, at least 90%, at least 95%, at least 97%, at least 98%, or at least 99% homology to the respective DGAT (RcDGAT1 and RcDGAT2); RcLPAT; LACS (RcLACS4), and PDAT (RcPDAT1A and RcPDAT1B) polypeptides (e.g., of SEQ ID NOS:54-59), or respective portions thereof.

Fusion Proteins

Fusion proteins comprising proteins or polypeptide fragments of inventive DGAT (RcDGAT1 and RcDGAT2); RcLPAT; LACS (RcLACS4), and PDAT (RcPDAT1A and RcPDAT1B) polypeptides (e.g., SEQ ID NOS:54-59) can also be constructed. Fusion proteins are useful for generating antibodies against amino acid sequences and for use in various targeting and assay systems. For example, fusion proteins can be used to identify proteins which interact with inventive DGAT (RcDGAT1 and RcDGAT2); RcLPAT; LACS (RcLACS4), and PDAT (RcPDAT1A and RcPDAT1B) polypeptides (e.g., SEQ ID NOS:54-59) or which interfere with the respective biological functions. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the inventive DGAT (RcDGAT1 and RcDGAT2); RcLPAT; LACS (RcLACS4), and PDAT (RcPDAT1A and RcPDAT1B) polypeptides (e.g., SEQ ID NOS:54-59) or can be prepared from biologically active variants of inventive DGAT (RcDGAT1 and RcDGAT2); RcLPAT; LACS (RcLACS4), and PDAT (RcPDAT1A and RcPDAT1B) polypeptides (e.g., SEQ ID NOS:54-59), such as those described above. The first protein segment can include a full-length inventive DGAT (RcDGAT1 and RcDGAT2); RcLPAT; LACS (RcLACS4), and PDAT (RcPDAT1A and RcPDAT1B) polypeptide (e.g., a full-length sequence selected from SEQ ID NOS:54-59).

Other first protein segments can consist of contiguous sub-amino acid regions from SEQ ID NOS:54-59.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and viral protein fusions. Other fusion are possible, as would be recognized by one skilled in the art.

These fusions can be made, for example, by covalently linking two protein segments or by standard procedures in the art of molecular biology. Recombinant DNA methods can be used to prepare fusion proteins, for example, by making a DNA construct which comprises a coding region for the protein sequence of one of SEQ ID NOS:54-59 in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MJC; Watertown, Mass.), and Quantum Biotechnologies (Montreal, Canada; 1-888-DNA-KITS).

Preferred Aspects of the Present Invention:

Particular aspects provide a novel isolated DNA sequence encoding a novel protein or polypeptide comprising or consisting of an amino acid sequence selected from the group consisting of SEQ ID NOS:54-59, respective biologically active portions thereof, and respective sequences having at least 85%, at least 90%, at least 95%, at least 97%, at least 98%, or at least 99% homology thereto. In certain aspects, the isolated coding sequence is selected from the group consisting of SEQ ID NOS:47-52 of *Ricinus communis*, and sequences having at least 85%, at least 90%, at least 95%, at least 97%, at least 98%, or at least 99% homology thereto.

Additional aspects provide a novel isolated protein or polypeptide, comprising or consisting of an amino acid sequence selected from the group consisting of SEQ ID NOS:54-59 of *Ricinus communis*, respective biologically active portions thereof, and respective sequences having at least 85%, at least 90%, at least 95%, at least 97%, at least 98%, or at least 99% homology thereto. Certain embodiments provide for fusion proteins comprising these novel sequences.

Further aspects provide a transfected cell, comprising at least one expression vector having a DNA sequence that encodes upon expression a protein or polypeptide comprising or consisting of an amino acid sequence selected from the group consisting of SEQ ID NOS:54-59, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. Preferably, the DNA sequence comprises a sequence selected from the group consisting of SEQ ID NOS: 47-52, and sequences having at least 85%, at least 90%, at least 95%, at least 97%, at least 98%, or at least 99% homology thereto.

Additional embodiments provide a novel antibody or epitope-binding fragment thereof specific for an amino acid sequence selected from the group consisting of SEQ ID NOS: 54-59, respective epitope-bearing portions thereof, and respective sequences having at least 85%, at least 90%, at least 95%, at least 97%, at least 98%, or at least 99% homology thereto. Preferably, the antibody or epitope-binding fragment thereof is a monoclonal antibody or antigen-binding fragment thereof.

Yet additional embodiments provide a method to enhance hydroxy fatty acid accumulation in plants, plant tissue, or plant seeds, comprising introducing, into at least one plant cell or tissue, at least one expression vector having a DNA sequence that encodes upon expression for at least one *Ricinus communis* enzymatic activity selected from the group consisting of RcDGAT2, RcPDAT1, RcLPAT1, and RcLACS4, provided that recombinant RcDGAT2 is expressed, wherein enhanced hydroxy fatty acid accumulation in the plant cell or tissue is, at least in part, afforded. Preferably, the method further comprises recombinant expression of a *Ricinus communis* oleoyl-12-hydroxylase.

Further embodiments provide method to enhance hydroxy fatty acid accumulation in plants, plant tissue, or plant seeds, comprising introducing, into at least one plant cell or tissue, at least one expression vector having a DNA sequence that encodes upon expression for at least one protein or polypeptide comprising or consisting of an amino acid sequence selected from the group consisting of SEQ ID NOS:54-59, respective biologically active portions thereof, respective sequences having at least 85%, at least 90%, at least 95%, at least 97%, at least 98%, or at least 99% homology thereto, and respective fusion proteins thereof operatively associated with a heterologous polypeptide, wherein enhanced hydroxy fatty acid accumulation in the plant cell or tissue is, at least in part, afforded. Preferably, the at least one expression vector comprises a DNA sequence that encodes upon expression at least one protein or polypeptide comprising or consisting of an amino acid sequence selected from the group consisting of SEQ ID NOS:54 and 56, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. More preferably, the at least one expression vector comprises a DNA sequence that encodes upon expression a protein or polypeptide comprising or consisting of an amino acid sequence selected from the group consisting of SEQ ID NO:54, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. Preferably the method further comprises recombinant expression of an oleoyl-12-hydroxylase, and most preferably, a *Ricinus communis* oleoyl-12-hydroxylase. In particular aspects, the *Ricinus communis* oleoyl-12-hydroxylase comprises or consists of an amino acid sequence selected from the group consisting of SEQ ID NO:62, respective biologically active portions thereof, respective sequences having at least 85%, at least 90%, at least 95%, at least 97%, at least 98%, or at least 99% homology thereto, and respective fusion proteins thereof operatively associated with a heterologous polypeptide.

Preferably, the DNA sequence of the at least one expression vector comprises a sequence selected from the group consisting of SEQ ID NOS:47 and 49, and sequences having at least 85%, at least 90%, at least 95%, at least 97%, at least 98%, or at least 99% homology thereto. Preferably, the DNA sequence comprises a sequence selected from the group consisting of SEQ ID NO:47, and sequences having at least 85%, at least 90%, at least 95%, at least 97%, at least 98%, or at least 99% homology thereto.

In particular aspects, the enhanced hydroxy fatty acid accumulation is in at least one form selected from the group consisting of fatty acids (FA), fatty acid esters, diacylglycerol (DAG), triaclyglcerol (TAG), and combinations thereof. Preferably, the enhanced hydroxy fatty acid accumulation is that of ricinoleic acid, and the enhanced ricinoleic acid accumulation is in at least one form selected from the group consisting of fatty acids (FA), fatty acid esters, diacylglycerol (DAG), triaclyglcerol (TAG), and combinations thereof.

In certain aspects the method for enhancing hydroxy fatty acid accumulation comprises recombinant expression of both: a protein or polypeptide comprising or consisting of an amino acid sequence selected from the group consisting of SEQ ID NO:54, respective biologically active portions thereof, respective sequences having at least 85%, at least 90%, at least 95%, at at least 97%, at least 98%, or at least 99% homology thereto, and respective fusion proteins thereof operatively associated with a heterologous polypeptide; and a protein or polypeptide comprising or consisting of an amino acid sequence selected from the group consisting of SEQ ID NO:56, respective biologically active portions thereof, respective sequences having at least 85%, at least 90%, at least 95%, at least 97%, at least 98%, or at least 99% homology thereto, and respective fusion proteins thereof operatively associated with a heterologous polypeptide. Preferably, the method further comprises recombinant expression of a oleoyl-12-hydroxylase, and preferably, a *Ricinus communis* oleoyl-12-hydroxylase (e.g., an amino acid sequence selected from the group consisting of SEQ ID NO:62, respective biologically active portions thereof, respective sequences having at least 85%, at least 90%, at least 95%, at least 97%, at least 98%, or at least 99% homology thereto, and respective fusion proteins thereof operatively associated with a heterologous polypeptide).

Yet further embodiments provide a method to increase at least one of total lipid content, percent seed germination, and seed weight in transgenic plants, plant tissue, or plant seeds, comprising introducing into at least one plant cell or tissue, at least one expression vector having a DNA sequence that encodes upon expression for at least one protein or polypeptide comprising or consisting of an amino acid sequence selected from the group consisting of SEQ ID NOS:54-59, respective biologically active portions thereof, respective sequences having at least 85%, at least 90%, at least 95%, at least 97%, at least 98%, or at least 99% homology thereto, and respective fusion proteins thereof operatively associated with a heterologous polypeptide, wherein at least one of total lipid content, percent seed germination, and seed weight is, at least in part, afforded. Preferably, the method further comprises recombinant expression of a oleoyl-12-hydroxylase, and most preferably, a *Ricinus communis* oleoyl-12-hydroxylase.

Antibodies or Antibody Fragments

Further aspects provide antibodies specific for plant DGAT (RcDGAT1 and RcDGAT2); RcLPAT; LACS (RcLACS4), or PDAT (RcPDAT1A and RcPDAT1B) enzymes of this invention Suitable antibodies may be polyclonal, monoclonal, or antigen and epitope binding portions of antibodies. Antibodies may be derived by conventional hybridoma based methodology, from antisera isolated from validated protein inoculated animals or through recombinant DNA technology. Alternatively, inventive antibodies or antibody fragments may be identified in vitro by use of one or more of the readily available phage display libraries. Exemplary methods are disclosed herein.

Baculovirus. Target proteins (e.g., plant DGAT (RcDGAT1 and RcDGAT2); RcLPAT; LACS (RcLACS4), and PDAT (RcPDAT1A and RcPDAT1B) enzymes of this invention) can be used in a baculovirus based system. By this method, target protein cDNAs or epitope-bearing fragments thereof are ligated into a suitable plasmid vector that is subsequently used to transfect Sf9 cells to facilitate protein production. In addition, it may be advantageous to incorporate an epitope tag or other moiety to facilitate affinity purification of the target protein. Clones of Sf9 cells expressing a particular protein are identified, e.g., by enzyme-linked immunosorbant assay (ELISA), lysates are prepared and the target protein purified by affinity chromatography. The purified target protein is, for example, injected intraperitoneally, into BALB/c mice to induce antibody production. It may be advantageous to add an adjuvant, such as Freund's adjuvant, to increase the resulting immune response.

Serum is tested for the production of specific antibodies, and spleen cells from animals having a positive specific antibody titer are used for cell fusions with myeloma cells to generate hybridoma clones. Supernatants derived from hybridoma clones are tested for the presence of monoclonal antibodies having specificity against a particular disclosed protein (e.g., SEQ ID NOS:54-59, or fragments thereof). For a general description of monoclonal antibody methodology, See, e.g., Harlow and Lane, *Antibodies: A Laboratory Manual*, Cold Spring Harbor Laboratory (1988).

In addition to the baculovirus expression system, other suitable bacterial or yeast expression systems may be employed for the expression of a particular target protein or polypeptides thereof. As with the baculovirus system, it may be advantageous to utilize one of the commercially available affinity tags to facilitate purification prior to inoculation of the animals. Thus, the target protein cDNA or fragment thereof may be isolated by, e.g., agarose gel purification and ligated in frame with a suitable tag protein such as 6-His, glutathione-S-transferase (GST) or other such readily available affinity tag. See, e.g., Molecular Biotechnology: Principles and Applications of Recombinant DNA, ASM Press pp. 160-161 (ed. Glick, B. R. and Pasternak, J. J. 1998).

Exemplary Nucleic Acid Sequences:

In addition to the inventive coding sequences of DGAT (RcDGAT1 and RcDGAT2); RcLPAT; LACS (RcLACS4), and PDAT (RcPDAT1A and RcPDAT1B) nucleic acid sequences disclosed herein (e.g., SEQ ID NOS:47-52, and related genomic and RNA sequence), examples of oligonucleotides of length X (in nucleotides), as indicated by polynucleotide positions with reference to, e.g., SEQ ID NOS:47-52, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, . . . (Y—(X−1));

where Y equals the length (nucleotides or base pairs) of, for example, SEQ ID NO:47 (1023); (RcDGAT2 orf)

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO of length Y is equal to Y−(X−1). For example Z=1023−19=1004 of either sense or antisense sets of SEQ ID NO:47, where X=20.

Examples of inventive 20-mer oligonucleotides include the following set of 1004 oligomers (and the antisense set complementary thereto), indicated by polynucleotide positions with reference to SEQ ID NO:47:

1-20, 2-21, 3-22, 4-23, 5-24, . . . and 1004-1023.

Likewise, examples of inventive 25-mer oligonucleotides include the following set of 999 oligomers (and the antisense set complementary thereto), indicated by polynucleotide positions with reference to SEQ ID NO:47:

1-25, 2-26, 3-27, 4-28, 5-29, . . . and 999-1023.

The present invention encompasses, for each of SEQ ID NOS:47-52 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to modulate expression (e.g., siRNA and antisense), and to ascertain genetic and epigenetic parameters of the genomic sequence corresponding to SEQ ID NOS:47-52. Preferred sets of such oligonucleotides or modified oligonucleotides of length X are those consecutively overlapping sets of oligomers corresponding to SEQ ID NOS:47-52 (and to the complements thereof).

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., BioTechniques 6:958-976, 1988) or intercalating agents (Zon, Pharm. Res. 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

Oligonucleotides having modified backbones include those retaining a phosphorus atom in the backbone, and those that do not have a phosphorus atom in the backbone.

Preferred modified oligonucleotide backbones include phosphorothioates or phosphorodithioate, chiral phosphorothioates, phosphotriesters and alkyl phosphotriesters, aminoalkylphosphotriesters, methyl and other alkyl phosphonates including methylphosphonates, 3'-alkylene phosphonates and chiral phosphonates, phosphinates, phosphoroamidates or phosphordiamidates, including 3'-amino phosphoroamidate and aminoalkylphosphoroamidates, and phosphorodiamidate morpholino oligomers (PMOs), thiophosphoroamidates, phosphoramidothioates, thioalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

The antisense oligonucleotide may also comprise at least one modified sugar moiety selected from the group including, but not limited to arabinose, 2-fluoroarabinose, xylulose, hexose and 2'-O-methyl sugar moieties.

The antisense oligonucleotide may comprise at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine (see also U.S. Pat. No. 5,958,773 and patents disclosed therein).

In addition to antisense oligos, representative siRNA sequence regions are disclosed herein; namely, in view of the above algorithm in combination with the teachings on sequences, design (e.g., length, structure, composition, etc), preparation and use thereof, provided herein below under "siRNA." Methods of preparing and using siRNA are generally disclosed in U.S. Pat. No. 6,506,559, incorporated herein by reference (see also reviews by Milhavet et al., Pharmacological Reviews 55:629-648, 2003; and Gitlin et al., J. Virol. 77:7159-7165, 2003; incorporated herein by reference).

The siRNA may comprise one or more strands of polymerized ribonucleotide, and may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition.

Example 1

Lipid Metabolic Genes from Castor Bean Developing Endosperm were Identified; Materials and Methods Used for Identification of Novel Castor Genes Overview. Unaccompanied introduction of the castor bean hydroxylase cDNA can produce up to ~17% HFA in total Arabidopsis seed lipids[7-9], but no one has pushed HFA accumlulation beyond this level. In one aspect, applicants' conception is that in developing castor seed, one or more steps in the biosynthetic pathway may be catalyzed by enzyme isoforms that display enhanced specificity for ricinoleate-containing substrates, such that optimal HFA production is mediated by a coordinate group of enhanced specificity enzymes. Aspects of the present invention, therefore, identify novel additional TAG metabolic enzymes from castor bean that can breach the prior art 17% HFA accumulation barrier. A castor bean developing endosperm library was screened for genes with known or possible roles in BFA incorporation into triacylglycerol (TAG).

The sought after cDNA sequences were those with possible roles in hydroxy fatty acid incorporation into TAG based on the proposed pathways shown in FIG. 1. In this scheme, a diacylglycerol acyltransferase (DGAT) is responsible for the acylation of diacylglyceraol (DAG) from an activated fatty acid. According to one aspect of applicants' conception, a castor bean DGAT enzyme is responsible for ricinoleic acid accumulation into triacylglyceraol (TAG), and its overexpression in a hydroxy-fatty-acid-producing *Arabidopsis* line allows for more hydroxy fatty acid accumulation. Likewise, in an alternate proposed pathway, ricinoleic acid is directly transferred from the sn-2 position of phosphatidylcholine (PC) onto DAG by phospholipid: diacylglycerol acyltransferase (PDAT). Again, if a castor bean PDAT is involved in regulating ricinoleic acid conversion to TAG, then its overexpression would lead to more hydroxy fatty acid accumulation in an *Arabidopsis* line expressing the hydroxylase cDNA. In addition to the DGAT and PDAT acyltransferases, other regulatory enzymes could be responsible for TAG incorporation. A long-chain acyl-CoA synthetase (LACS) enzyme specific for ricinoleic acid could be responsible for efficiently activating ricinoleic acid to ricinoleoyl-CoA, allowing DGAT to transfer ricinoleic acid to DAG. Additionally, an LPAAT (aka, LPAT) enzyme could be responsible for transferring ricinoleic acid from ricinoleoyl-CoA to glycerol 3-phosphate, forming phosphatidic acid, which is subsequently converted to DAG. This DAG could then be incorporated into TAG by either a DGAT or PDAT enzyme. Accordingly, in consideration of the possible existence and potential roles for castor DGAT, PDAT, LACS, and LPAAT enzymes, full-length cDNAs were sought after in a developing seed castor bean cDNA library.

Degenerate primers (TABLE 2 below in this Example) were designed based on regions of amino acid identity between known and predicted proteins of plant species (e.g., DGAT, PDAT, LACS, and LPAT proteins). These primers were used to amplify partial sequences from a castor bean cDNA library (either a *Ricinus communis* seed specific full-length cDNA library developed in applicants' laboratory, or from a similar library provide to applicants by Paul Roessler).

Gene-specific primers (TABLE 2) were then used to isolation of full-length cDNA sequences by 5' and 3' RACE (Rapid Amplification of cDNA Ends) reactions.

Sequence information from the generated products was used to create end-to-end amplification primers. Full length sequences were analyzed and re-amplified out of the castor cDNA library for comparison. All DNA sequencing was performed using an ABI-Prism 3100-Avant Genetic Analyzer (Applied Biosystems, Foster City, Calif.) and all DNA analysis was performed on Vector NTI Suite software (Bethesda, Md.).

Six cDNA clones were acquired (TABLE 3 below). These included two classes of DGAT gene (cDNA) sequences, namely RcDGAT1 (SEQ ID NO:48) (~74% amino acid identity to AtDGAT1 (At2g19450)[16,17]) and RcDGAT2 (SEQ ID NO:47) (~71% amino acid identity to AtDGAT2 (At3g51520)[18]). Several LPAAT full-length cDNA sequences were also found, and one putative LPAT (SEQ ID NO:51) (RcLPAT1, ~92% identity to putative *Arabidopsis* LPAT At5g60620) was cloned and analyzed. Additionally, one LACS cDNA, RcLACS4 (SEQ ID NO:52) was cloned and analyzed (showing-85% identity to AtLACS4 (At4g23850)[19]). Two closely related PDAT cDNAs were also been cloned; namely RcPDAT1A (SEQ ID NO:49) (~81% identity to ATPDAT (At5g13640)) and RcPDAT1B (SEQ ID NO:50) (~83% identity to AtPDAT1 (At5g13640)).

After obtaining the full length cDNA sequences (see TABLE 3 herein below for open reading frames of novel cDNAs, the cDNAs were amplified out of the castor cDNA library using end-specific primers containing restriction sites appropriate for cloning into pBLUESCRIPT SK™ (Stratagene, Cedar Creek, Tex.) (see EXAMPLE 2, below for details).

TABLE 2

Degenerate primers were designed according to regions of amino acid conservation between plant species. The primers were used for finding castor bean ORFs from cDNA library and subsequent PCR and cloning.

| Gene Name | Primer Name | Sequence | Forward or Reverse | Use | Approx. Product Size |
|---|---|---|---|---|---|
| RcLACS4 | AMPBS | CGIASIASIGGIVHWCYIAARGG (SEQ ID NO: 1) | forward | degenerate primer for LACS hunt used with primer ACSDRKK | 900 |
| RcLACS4 | ACSDRKK | RTCNCCNGTRTRNARCCANC (SEQ ID NO: 2) | reverse | degenerate primer for LACS hunt used with primer AMPBS | 900 |
| RcLACS4 | RcLACS4 5N | GTGGATGTATGCCTAGAATCTGTTC (SEQ ID NO: 3) | forward | Used with T7 for 3' RACE | 1000 |
| RcLACS4 | RcLACS4 3' | CACCAATATCACCTGTGTGGAACCA (SEQ ID NO: 4) | reverse | Used with M13R for 5' RACE | 2000 |
| RcLACS4 | RcLACS4 5'Pst | ACTACACTGCAGAAATGGCACAACAGA GGCAGAG (SEQ ID NO: 5) | forward | Used with RcLACS4 3'Xho for cloning into pOEA2 | 2010 |

TABLE 2-continued

Degenerate primers were designed according to regions of amino acid conservation between plant species. The primers were used for finding castor bean ORFs from cDNA library and subsequent PCR and cloning.

| | | | | | |
|---|---|---|---|---|---|
| RcLACS4 | RcLACS4 3'Xho | GATCAACTCGAGTCAAGCACTGGGTTT GCTTGC (SEQ ID NO: 6) | reverse | Used with RcLACS4 5'Pst for cloning into pOEA2 | 2010 |
| RcDGAT2 | DGAT2 down | GGIYKICCIACIAYIACRTKIATNGG (SEQ ID NO: 7) | reverse | degenerate primer for DGAT2 hunt used with DGAT up | 500 |
| RcDGAT2 | DGAT2 up | CARWSIGCIGGICTITTYAAYCT (SEQ ID NO: 8) | forward | degenerate primer for DGAT2 hunt used with DGAT down | 500 |
| RcDGAT2 | RcDGAT2 5N | GTAACGCTGTGTTTCGCACACCAGT (SEQ ID NO: 9) | forward | Used with T7 for 3' RACE OR RcDGAT2 3' for RcDGAT2-specific PCR | 850; 330 |
| RcDGAT2 | RcDGAT2 3' | ACCGAGAACTCCCCAAAAGACAATTG (SEQ ID NO: 10) | reverse | Used with M13R for 5' RACE OR RcDGAT2 5N for RcDGAT2-specific PCR | 1000; 330 |
| RcDGAT2 | RcDGAT2 PstI | ACTACACTGCAGAAATGGGGGAAGAAG CGAATCATAA (SEQ ID NO: 11) | forward | Used with RcDGAT2 XhoI for cloning into pOEA2 | 1030 |
| RcDGAT2 | RcDGAT2 XhoI | GATCAACTCGAGTCAAAGAATTTCAAG (SEQ ID NO: 12) | reverse | Used with RcDGAT2 PstI for cloning into pOEA2 | 1030 |
| RcDGAT2 | RcDGAT2 BamHI | TCAGATGGTACCAAATGGGGGAAGAAG CGAATCATAA (SEQ ID NO: 13) | forward | Used with RcDGAT2 XhoI for cloning into pYES2 | 1030 |
| RcDGAT1, RcLPAAT1 | DGAT1 up | CARWSIGCIGGICTITTYAAYCT (SEQ ID NO: 14) | forward | degenerate primer for DGAT1 hunt used with DGAT1 down1 & down2 | 1140, 825 |
| RcDGAT1, RcLPAAT1 | DGAT1 down | TGRTARTAIAGIAGIACRCACATIGG (SEQ ID NO: 15) | reverse | degenerate primer for DGAT1 hunt used with DGAT1 up1 and up2 | 1140, 680 |
| RcDGATI, RcLPAAT1 | DGAT1 up2 | TCICTIGYITAYTTYATGVTIGCN (SEQ ID NO: 16) | forward | degenerate primer for DGAT1 hunt used with DGAT1 down1 & down2 | 680, 370 |
| RcDGAT1, RcLPAAT1 | DGAT1 down2 | ACNGGCATRTTCCAIAKICKCCAR (SEQ ID NO: 17) | reverse | degenerate primer for DGAT1 hunt used with DGAT1 up1 and up2 | 825, 370 |
| RcDGAT1 | RcDGAT1 5N | TGTGCTGTCTTTCTCTCCCAGTA (SEQ ID NO: 18) | forward | Used with M13F for 3' RACE | 1000 |
| RcDGAT1 | RcDGAT1 3out | TAAATTCGGAACTGAGAGCTTCAGA (SEQ ID NO: 19) | reverse | Used with T3 for 5' RACE-primary reaction | 1000 |
| RcDGAT1 | RcDGAT1 3in | CTTTTAAAGGGTGTTGAGAATTC (SEQ ID NO: 20) | reverse | Used with M13R for 5' RACE OR T3 for 5' RACE- secondary reaction | 900; 950 |
| RcDGAT1 | RcDGAT1 5'Pst | CGTTGACTGCAGAAATGACGATTCTCG AAACGCCAGAA (SEQ ID NO: 21) | forward | Used with RcDGAT1 XhoI for cloning into pOEA2 | 1570 |
| RcDGAT1 | RcDGAT1 3'Xho | TCATCACTCGAGTCAGTTCCCATCGCG ATTCATTAGGT (SEQ ID NO: 22) | reverse | Used with RcDGAT1 PstI for cloning into pOEA2 | 1570 |
| RcLPAAT1 | RcLPAAT1 5' ATG | AGCACTGCGGGTAAACTAAACTC (SEQ ID NO: 23) | forward | Used with capped oligo dT primer for 3' RACE | 1000 |
| RcLPAAT1 | RcLPAAT1 5' Pst | CGTTGACTGCAGAAATGAGCACTGCGG GTAAACTAAAC (SEQ ID NO: 24) | forward | Used with RcLPAAT1 3' Xho for cloning into pOEA2 | 1100 |
| RcLPAAT1 | RcLPAAT1 3' Xho | CTACGACTCGAGTTACTTCTCCTCCAG GCGCCGTA (SEQ ID NO: 25) | reverse | Used with RcLPAAT1 5' Pst for cloning into pOEA2 | 1100 |

TABLE 2-continued

Degenerate primers were designed according to regions of
amino acid conservation between plant species. The primers
were used for finding castor bean ORFs from cDNA library
and subsequent PCR and cloning.

| Gene Name | Primer Name | Sequence | Forward or Reverse | Use | Approx. Band Size |
|---|---|---|---|---|---|
| AtDGAT2 | AtDGAT2 PstI | ACTACACTGCAGAAATGGGTGGTTCCA GAGAGTTC (SEQ ID NO: 26) | forward | Used with AtDGAT2 XhoI for cloning into pOEA2 | 950 |
| AtDGAT2 | AtDGAT2 XhoI | TACGATCTCGAGTCAAAGAATTTTCAG CTCAAGATC (SEQ ID NO: 27) | reverse | Used with AtDGAT2 PstI for cloning into pOEA2 | 950 |
| AtDGAT2 | AtDGAT2 5N | TTCATATGCAACATGATGCTGAG (SEQ ID NO: 28) | forward | Used with AtDGAT2 3'Sph for AtDGAT2-specific PCR | 380 |

| Gene Name | Primer Name | Sequence | Forward or Reverse | Use | Approx. Product Size |
|---|---|---|---|---|---|
| AtDGAT2 | AtDGAT2 3' Sph | ACTACACTGCAGAAATGGGTGGTTCCA GAGAGTTC (SEQ ID NO: 29) | reverse | Used with AtDGAT2 5N for AtDGAT2-specific PCR | 380 |
| AtDGAT2 | AtDGAT2 BamHI | TCAGATGGTACCAAATGGGTGGTTCC AGAGAGTTC (SEQ ID NO: 30) | forward | Used with AtDGAT2 XhoI for cloning into pYES2 | 950 |
| RcPDAT | motif 7 | TAYTTYYTICAYTTYMTIAARTGGGT (SEQ ID NO: 31) | reverse | Used with M13F for PDAT hunt- primary reaction | 1300 |
| RcPDAT | motif 8 | GCNCAYTTYTCNYAYGGNATHGCHGA (SEQ ID NO: 32) | reverse | Used with M13F for PDAT hunt- secondary reaction | 700 |
| RcPDAT | motif 9 | AARTAYTGGTCIAAYCCHYTNGARACH AA (SEQ ID NO: 33) | reverse | Used with M13F for PDAT hunt- primary reaction | 600 |
| RcPDAT | motif 10 | TAYGGIGTIGGIATHCCHACNGA (SEQ ID NO: 34) | reverse | Used with M13F for PDAT hunt- secondary reaction | 550 |
| RcPDAT1A | RcPDAT1A 5' | ATGTCGATTTTGAGACGGAGATTAAG (SEQ ID NO: 35) | forward | Used with T3 for 5' RACE | 1600 |
| RcPDAT1A | RcPDAT1A 5'Asc | TACACAGGCGCGCCAAATGTCGATTTT GAGACGGAGATTA (SEQ ID NO: 36) | forward | Used with RcPDAT1A Xho for cloning into pOEA2 | 2000 |
| RcPDAT1A | RcPDAT1A 3'Xho | GATCAACTCGAGCTATGAATCTATAGC GGCCAAGT (SEQ ID NO: 37) | reverse | Used with RcPDAT1A Asc for cloning into pOEA2 | 2000 |
| RcPDAT1B | RcPDAT1B 5' | ATGCCTGTAATTCGGAGGAAAAAAC (SEQ ID NO: 38) | forward | Used with T3 for 5' RACE | 1600 |
| RcPDAT1B | RcPDAT1B 3out | AATGATCGTACTCTCTAATGTATGTTC (SEQ ID NO: 39) | reverse | Used with T3 for 5' RACE- primary reaction | 1000 |
| RcPDAT1B | RcPDAT1B 3in | CAGCCATCTTCATCGCCATCATTAG (SEQ ID NO: 40) | reverse | Used with T3 for 5' RACE- secondary reaction | 950 |
| RcPDAT1B | RcPDAT1B 5' Pst | ACTAGACTGCAGAAATGCCTGTAATTC GGAGGAAAAAAC (SEQ ID NO: 41) | forward | Used with RcPDAT1B 3'Xho for cloning into pOEA2 | 2000 |
| RcPDAT1B | RcPDAT1B 3'Xho | GTCGATCTCGAGTTACAGTGGTAATTT GATCTTCTGA (SEQ ID NO: 42) | reverse | Used with RcPDAT1B 5'Pst for cloning into pOEA2 | 2000 |
| | capped oligo dT | T20(A) + T20(C) + T20(G) in equimolar | | | |
| | M13F | GTAAAACGACGGCCAGT (SEQ ID NO: 43) | | | |

TABLE 2-continued

Degenerate primers were designed according to regions of amino acid conservation between plant species. The primers were used for finding castor bean ORFs from cDNA library and subsequent PCR and cloning.

| | | |
|---|---|---|
| M13R | GGAAACAGCTATGACCATG | (SEQ ID NO: 44) |
| T7 | GTAATACGACTCACTATAGGGC | (SEQ ID NO: 45) |
| T3 | AATTAACCCTCACTAAAGGG | (SEQ ID NO: 46) |

Nucleotide abbreviations used: B = C, T, G; D = A, T, G; H = A, C, T; I = inosine; K = T, G; M = A, C; R = A, G; S = C, G; Y = C, T; and N = A, T, C, G

TABLE 3

All of the novel open reading frame sequences were cloned and expressed in *Arabidopsis* seeds. The Rc sequences were those found by using the degenerate primers listed in TABLE 2, against the castor bean developing seed cDNA library.

AtDGAT2 ORF(At3g51520)- 945 bases (SEQ ID NO: 53)
```
  1 ATGGGTGGTT CCAGAGAGTT CCGAGCTGAG GAACATTCAA ATCAATTCCA
    CTCTATCATC GCCATGGCCA TCTGGCTTGG CGCCATTCAC TTCAACGTCG 101 CTCTTGTTCT CTGTTCTCTC ATTTTCCTTC CTCCTTCTCT ATCTCTCATG
    GTCTTGGGCT TGCTCTCTCT GTTTATCTTT ATCCCAATCG ATCATCGTAG 201 CAAATATGGT CGTAAGCTCG CTAGGTACAT ATGCAAGCAC GCGTGTAATT
    ATTTCCCCGT CTCTCTGTAC GTCGAGGATT ACGAAGCTTT CCAGCCTAAT 301 CGTGCCTATG TCTTTGGTTA TGAACCACAT TCGGTGCTAC CGATTGGAGT
    TGTTGCTCTT TGTGATCTCA CAGGGTTTAT GCCTATTCCT AACATTAAAG 401 TTCTTGCAAG TAGTGCTATA TTCTACACTC CCTTTCTAAG GCATATATGG
    ACATGGTTAG GGCTCACCGC TGCTTCTAGG AAGAATTTCA CTTCCCTTTT 501 GGATTCTGGC TACAGTTGTG TTCTTGTACC TGGTGGTGTG CAGGAGACTT
    TTCATATGCA ACATGATGCT GAGAATGTCT TCCTTTCAAG GAGAAGAGGA 601 TTTGTGCGCA TAGCCATGGA ACAGGGGAGC CCTCTGGTTC CAGTATTCTG
    CTTTGGTCAG GCACGCGTGT ACAAATGGTG GAAGCCGGAT TGTGATCTCT 701 ATCTTAAACT ATCTAGAGCA ATCAGATTCA CCCCGATCTG CTTCTGGGGA
    GTTTTTGGAT CACCATTACC GTGTCGACAG CCTATGCATG TGGTCGTTGG 801 TAAACCAATA GAAGTCACAA AAACTCTGAA GCCAACTGAC GAAGAGATTG
    CTAAGTTTCA TGGCCAGTAT GTGGAAGCGC TTAGGGATCT GTTTGAGAGG

901 CACAAGTCCC GAGTCGGCTA TGATCTTGAG CTGAAAATTC TTTGA
```

RcDGAT2 ORF (1023 bases) (SEQ ID NO: 47)
```
  1 ATGGGGGAAG AAGCGAATCA TAATAATAAT AATAATAATA TCAATAGTAA
    TGATGAGAAG AATGAAGAGA AATCAAATTA TACAGTTGTA AATTCGAGAG 101 AACTATACCC AACGAACATA TTTCACGCAC TGTTAGCGTT GAGCATATGG
    ATTGGTTCAA TCCATTTCAA TCTCTTCTTA CTCTTCATCT CTTATCTCTT 201 CCTTTCTTTT CCCACATTCC TCCTGATTGT TGGATTTTTT GTGGTGTTAA
    TGTTCATTCC GATCGACGAA CACAGTAAGT TGGGCCGTCG TTTGTGCAGG 301 TATGTATGCA GACATGCGTG CAGTCATTTT CCGGTAACTC TCCATGTTGA
    AGACATGAAT GCTTTTCATT CTGATCGTGC TTACGTTTTT GGTTATGAGC 401 CACATTCAGT ATTTCCCCTT GGTGTTTCTG TACTATCAGA TCACTTTGCT
    GTCCTGCCCC TTCCTAAAAT GAAGGTCCTT GCAAGTAACG CTGTGTTTCG 501 CACACCAGTT TTAAGGCATA TATGGACATG GTGTGGTCTT ACATCAGCAA
    CAAAGAAAAA TTTCACTGCC CTCCTAGCAT CTGGTTATAG TTGCATTGTG 601 ATTCCCGGTG GAGTTCAAGA CATTTTATA TGAAGCATG GCTCTGAGAT
    TGCTTTCCTT AAGGCGAGAA GAGGGTTTGT CCGAGTAGCT ATGGAGATGG
```

TABLE 3-continued

All of the novel open reading frame sequences
were cloned and expressed in *Arabidopsis*
seeds. The Rc sequences were those found by
using the degenerate primers listed in TABLE 2,
against the castor bean developing seed cDNA
library.

```
 701 GTAAACCCTT GGTTCCAGTT TTCTGCTTTG GTCAATCGAA CGTGTACAAG
     TGGTGGAAAC CTGATGGCGA GTTATTTATG AAAATTGCTA GAGCTATTAA

801 GTTCAGCCCA ATTGTCTTTT GGGGAGTTCT CGGTTCTCAT TTACCGCTAC
     AACGTCCAAT GCATGTTGTC GTCGGTAAAC CGATTGAGGT GAAGCAAAAT

901 CCACAGCCTA CAGTGGAAGA GGTCTCAGAA GTACAGGGTC AGTTTGTTGC
     GGCACTTAAA GATCTTTTTG AAAGGCATAA AGCACGGGTT GGCTATGCAG

1001 ACCTTACACT TGAAATTCTT TGA
```

RcDGAT1 ORF (1566 bases) (SEQ ID NO: 48)
```
   1 ATGACGATTC TCGAAACGCC AGAAACTCTT GGCGTCATCT CCTCCTCCGC
     CACTTCCGAT CTCAACCTCT CTCTCCGACG TAGACGGACC TCAAATGACT 101 CCGATGGTGC ACTTGCTGAT TTGGCTTCGA AGTTTGATGA TGATGACGAC
     GTAAGATCGG AAGATTCTGC TGAAAATATT ATCGAAGATC CTGTAGCAGC 201 GGTTACTGAA TTGGCGACAG CAAAGAGTAA CGGAAAAGAC TGTGTTGCCA
     ATAGTAATAA GGATAAAATT GATAGCCATG GAGGATCATC GGATTTTAAA 301 CTTGCATATA GGCCTTCGGT TCCAGCTCAC CGGTCACTTA AGGAGAGTCC
     GCTTAGCTCT GATTTAATAT TTAAACAAAG TCATGCAGGT CTGTTTAACC 401 TTTGTATAGT AGTGCTCGTA GCTGTTAACA GCAGGCTCAT CATTGAGAAT
     TTAATGAAGT ATGGCTGGTT AATTAAGACG GCTTTTGGT TTAGTTCAAG 501 ATCATTGAGA GATTGGCCGC TTTTTATGTG CTGTCTTTCT CTCCCAGTAT
     TCCCCCTTGC TGCCTATCTA GTTGAGAAGG CCGCATATCG AAAATATATA 601 TCTCCGCCTA TTGTTATTTT CCTTCATGTG ATCATCACCT CAGCAGCTGT
     TTTGTACCCA GCTTCTGTAA TTCTCAGTTG TGAATCTGCT TTTTTATCTG 701 GTGTCACATT GATGGAACTT GCTTGTATGG TATGGTTGAA ATTGGTATCC
     TATGCACATA CAAACTATGA TATGAGAGCG ATCGCTGACA CCATTCATAA 801 GGAAGATGCA TCCAATTCTT CTAGTACAGA GTATTGTCAT GATGTGAGCT
     TTAAGACTTT GGCGTACTTC ATGGTCGCAC CCACATTATG TTACCAGCCA 901 AGTTATCCTC GCACAGCATT TATTAGAAAG GGCTGGGTGT TCCGTCAATT
     TGTCAAACTA ATAATTTTTA CAGGATTCAT GGGATTTATC ATAGAACAAT 1001 ACATCAATCC TATCGTCCAG AATTCTCAAC ACCCTTTAAA AGGGGATCTC
     TTATATGCCA TTGAGAGGGT TCTGAAGCTC TCAGTTCCGA ATTTATATGT 1101 GTGGCTCTGC TTGTTCTACT GCTTTTTTCA CCTGTGGTTG AATATAGTTG
     CTGAGCTCCT TCGCTTCGGT GACCGGGAGT TCTACAAAGA TTGGTGGAAT 1201 GCAAAAACTG TTGAGGAGTA CTGGAGGATG TGGAATATGC CTGTTCACAA
     GTGGATGGTT CGCCATATCT ACTTCCCATG CCTACGTCGT AAAATACCAA 1301 GGGGGGTAGC AATAGTTATT GCTTTCTTCG TTTCAGCTGT ATTTCATGAG
     TTGTGCATTG CTGTTCCTTG CCACATGTTC AAACTTTGGG CTTTTTTTGG 1401 AATAATGTTT CAGATTCCTT TAGTTGTGAT CACTAATTAT TTTCAAAGGA
     AGTTCAGAAG CTCAATGGTG GGAAATATGA TCTTCTGGTT CTTTTTCTGC 1501 ATTCTCGGCC AACCTATGTG TGTACTGTTG TATTACCATG ACCTAATGAA
     TCGCGATGGG AACTGA
```

RCPDAT1A ORF (1992 bases) (SEQ ID NO: 49)
```
   1 ATGTCGATTT TGAGACGGAG ATTAAGAGTG CAAAATTCTT CCCAAATTGA
     GGCCGACAAC GATGAGAAAG AGAAGGAGAA GCGAAAGAGA AGAAAAGAGA 101 TCAAGAAATG GAGGTGCGTG GACAATTGCT GTTGGTTTAT AGGTTTTATA
     TGTTCGATGT GGTGGTTTTT ACTATTTTTA TACAATGCAA TGCCTGCTTC 201 TTTTCCTCAA TATGTGACGG AGGCGATAAC GGGACCGATG CCGGACCCAC
     CTGGCGTTAA ATTAAGGAAG GAAGGGTTGA CTGTCAAACA TCCGGTGGTT 301 TTTGTGCCTG GCATTGTTAC AGGTGGACTT GAGTTATGGG AAGGACATCA
     GTGTGCTGAT GGTTTGTTTA GAAAACGACT TTGGGGTGGT ACATTTGGTG
```

TABLE 3-continued

All of the novel open reading frame sequences were cloned and expressed in *Arabidopsis* seeds. The Rc sequences were those found by using the degenerate primers listed in TABLE 2, against the castor bean developing seed cDNA library.

```
 401 ATCTCTACAA AAGACCACTA TGCTGGGTTG AGCATATGTC TCTGGACAAT
     GAAACAGGAC TAGACCCTCC TGGCATTAGG GTCAGGGCTG TATCTGGACT

501 TGTGGCAGCT GATTATTTTG CAGCAGGTTA TTTTGTCTGG GCAGTTTTAA
     TTGCTAATTT GGCTCGCCTT GGGTATGAGG AGAAAAACAT GTATATGGCT

601 GCATATGACT GGAGACTATC ATTTCAGAAC ACTGAGATTA GGGACCAAAG
     TTTGAGCAGG ATAAAAAGTA ATATAGAACT CATGGTGGCT ACCAATGGCG

701 GGAATAAGGT GGTTGTTCTT CCACATTCAA TGGGTGTTCC ATACTTTCTG
     CATTTCATGA AATGGGTAGA GGCACCAGCT CCAATGGGTG GTGGGGTGG

801 ACCTGATTGG TGTGCCAAGC ACATAAAAGC GGTGATCAAT ATTGGTGGAC
     CATTTCTGGG TGTGCCAAAA GCAATCTCAT CACTTTTCTC AAATGAAGGA

901 AGGGATATTG CTGCAGCCAG GGCTTTCGCG CCAGGATTTT TGGATAAGGA
     TGTTTTTGGT CTTCAAACTT TTCAGCATGC AATGCGATTG ACTCGGACAT

1001 GGGATTCAAC CATGTCCATG ATACCAAAAG GTGGGGAAAC TATCTGGGGT
     GGCCTTGATT GGTCGCCTGA AGGAGTCTAC AACTGTGGTT CAAACACACC

1101 AAAGAACAAT AATACCCAGA CTGCAGGTCA AACTGGGAAA GGAACTTCAA
     GTTTCACAGA AGGTGTGAAC TATGGGAGAA TTATATCGTT TGGGAAAGAT

1201 GTGGCTGAGC TTCATTCTTC CAAATTGAT AGGATAGATT TCAGGGATGC
     TGTTAAGGGT AATAGAGTTG CAAACAATTG TGACATCTGG ACGGAGTACC

1301 AAGAAATGGG TATTGGAGGT ATCAAAGCTG TTGCTGATTA TAAAGTATAC
     ACAGCTGGAT CAGTTATAGA TCTGCTGCAT TTTGTAGCTC CTAAGCTTAT

1401 GGCACGTGGA GATGCTCATT TTTCACATGG GATTGCGGAC AATTTGGACG
     ATCCAAAATA TGAGCACTAC AAATATTGGT CAAACCCTTT GGAAACAAGA

1501 TTACCAGATG CTCCTGAGAT GGAGTTATAT TCTATGTATG GAATTGGAAT
     ACCGACTGAA AGAGCATATA TTTACAAGCT AACTCTAACC AGTGAATGCG

1601 CTATTCCCTT TCAGATAGAT ACCTCAGTGA CAGGTGGAAG CGAGAACTCT
     TGTCTAAAAG ATGGAACTCT TAATGTTAAT GGAGACGAGA CAGTTCCTGT

1701 ATTAAGTGCT GGTTTTATGT TTGCAAAGGG TTGGCGAGGG AAAACTAGAT
     TCAACCCTTC AGGCATTCAT ACTTATATAA GGGAATATAA TCACGCTCCA

1801 CCTGCTAATC TTCTGGAGGG TCGAGGCACC CAGAGTGGTG CTCATGTTGA
     TATCTTGGGG AATTTTGCAT TAATAGAGGA CGTTTTAAGG ATAGCAGCTG

1901 GAGCTAGAGG AGAGGATTTG GGAGGAGACC GAGTTTATTC TGATATTTTC
     AAATGGTCTG AGAAGATCAA CTTGGCCGCT ATAGATTCAT AG
```

RcPDAT1B ORF (2058 bases) (SEQ ID NO: 50)

```
   1 ATGCCTGTAA TTCGGAGGAA AAACCCACT TCTGAACCCA ACAAAAATTC
     AGCATCAGAC TCAAAAACGC CAAGCGAGGA AGAGGAACAT GAACAAGAAC

101 AGGAACAAGA AGAAGATAAA AATAACAAAA AGAAATACCC AAAGAAGAAG
     AGCAGTGAAA TCAATGCAAA AAAATGGTCA TGCATAGACA GCTGTTGTTG

201 GTTTGTTGGT TGCATCTGCG TGACGTGGTG GGTTTTACTA TTTCTTTACA
     ATGCAGTGCC TGCGTCTTTG CCTCAATACG TAACTGAGGC AATCACGGGT

301 CCTTTACCCG ATCCACCTGG TGTTAAGCTG AAAAAGAGG GATTAACAGC
     AAAGCATCCA GTGGTTTTTG TACCTGGGAT TGTTACCGCG GGGCTTGAAT

401 TGTGGGAAGG CCATCAGTGT GCTGATGGGC TGTTTAGGAA ACGGCTCTGG
     GGTGGAACTT TTGGAGAAGT TTATAAGAGG CCTCTCTGCT GGGTAGAGCA

501 TATGTCTCTA GACAATGAAA CTGGATTGGA TCCTCCTGGT ATAAGGGTCA
     GGCCAGTCTC TGGACTTGTG GCTGCTGATT ACTTTGCTCC AGGCTATTTT

601 GTGTGGGCTG TTCTGATTGC TAATTTGGCA CGCATTGGAT ATGAGGAGAA
     AACAATGTTC ATGGCCTCAT ACGATTGGAG ACTTTCATTT CAGAACACTG

701 AGGTCCGTGA CCAAACATTA AGCCGGATGA AGAGTAATAT AGAACTTATG
     GTTTCTATCA ATGGTGGAAA TAAGGCAGTT ATTGTTCCAC ATTCCATGGG
```

TABLE 3-continued

All of the novel open reading frame sequences
were cloned and expressed in *Arabidopsis*
seeds. The Rc sequences were those found by
using the degenerate primers listed in TABLE 2,
against the castor bean developing seed cDNA
library.

```
 801 TGTTTTGTAC TTTCTGCATT TTATGAAGTG GGTTGAGGCA CCAGCTCCAA
     TGGGAGGAGG TGGTGGACCA GATTGGTGTG CTAAGCATAT CAAGGCAGTC

901 ATGAACATTG GTGGTCCATT TTTAGGTGTT CCCAAAGCTG TTGCTGGGCT
     TTTCTCGGCT GAAGCAAGAG ATATTGCAGT TGCCAGGGCC ATAGCACCAG

1001 GTTTCTTAGA TAATGATATG TTCCGCCTAC AAACATTGCA ACACATGATG
     AGGATGTCTC GCACATGGGA TTCGACCATG TCAATGATAC CAAGAGGTGG

1101 GGACACTATC TGGGGCGATC TTGATTGGTC ACCTGAAGAA GGTTACATTC
     CTAGAAAGAA AAGGCAGAGA AATAATGCAA CTGATAATGT AAACGAAGGT

1201 GGGGCCGAAA GTGAGATTTC TCAAAGAAAG ATTGTTAGAT ATGGAAGAAT
     GATATCATTT GGGAAAAATA TAGCAGAGGC ACCTTCATAT GATATTGAAA

1301 GGATTGACTT TAGGGATGCT GTTAAAGGTC GTAGTGTGGC AAATAATACC
     TGCCTTGATG TGTGGACTGA ATACCATGAA ATGGGATTCG GAGGTATTAA

1401 AGCCGTTGCA GAGTATAAGG TCTACACTGC TGGATCTACT ATAGAGCTGC
     TTCAGTTTGT CGCCCCAAAA ATGATGGAGC GTGGTAGTGC TCATTTTTCT

1501 TATGGAATTG CTGACAATTT GGAGGACCCA AAATATGAGC ACTACAAATA
     CTGGTCAAAT CCCCTGGAGA CAAAGTTACC TAATGCTCCA GAAATGGAAA

1601 TATTTTCCAT GTATGGAGTT GGCATACCAA CAGAAAGAGC TTATGTTTAT
     GAGTTTTCTC CTGCTGCTGA GTGCTACATT CCATTTCAGA TTGATACATC

1701 AGCTAATGAT GGCGATGAAG ATGGCTGTCT GAAAGATGGA GTCTATACTG
     TTGATGGGGA TGAGACTGTT CCTGTTTTAA GTGCAGGCTT CATGTGTGCT

1801 AAAGCTTGGC GTGGGAAAAC CAGATTTAAT CCTTCAGGAA GTCGAACATA
     CATTAGAGAG TACGATCATT CTCCTCCAGC TAATTTGCTA GAGGGCCGAG

1901 GCACCCAAAG TGGTGCCCAT GTTGATATAA TGGGTAATTT TGCTTTAATC
     GAGGATATTA TGAGGGTGGC AGCCGGGGCT ACAGGAGAAG ATTTGGGAGG

2001 CGATCAAGTG TATTCAGATA TCTTTAAGTG GTCTCAGAAG ATCAAATTAC
     CACTGTAA

RcLPAAT1 ORF (1128 bases) (SEQ ID NO: 51)
   1 ATGAGCACTG CGGGTAAACT AAACTCATCG AGCTCAGAAT TGGACTTGGA
     TCGACCTAAT ATCGAAGATT ATCTTCCTTC TGGATCCTCT ATTCATGAAC 101 CTCACGGCAA GCTCCGCCTG CGTGATTTGC TGGATATTTC GCCAGCCCTA
     ACAGAAGCAG CTGGTGCAAT TGTTGATGAC TCGTTTACAC GATGTTTCAA 201 GTCGAATCCT CCTGAACCAT GGAATTGGAA TATATATCTA TTTCCCCTAT
     GGTGTTGTGG TGTTGTGATT CGATATGGGA TTTTGTTCCC TGTCAGGGTT 301 CTGGTGCTGA CGATAGGGTG GATAATATTT CTTTCAGCGT ACATTCCTGT
     GCATTTGCTA CTGAAAGGAC ATGAGAAGTT GAGGAAAAAG TTAGAGAGGT 401 GTTTGGTGGA GTTAATTTGC AGCTTCTTTG TGGCATCATG GACTGGAGTT
     GTCAAGTACC ATGGGCCACG GCCTAGCATT CGACCTAAAC AGGTTTTTGT 501 GGCTAATCAT ACCTCCATGA TTCATTTTAT CGTCTTAGAG CAGATGACTG
     CATTTGCTGT TATTATGCAA AAACATCCTG GTTGGGTTGG ACTTTTACAA 601 AGCACTATAC TAGAGAGTGT TGGTTGTATC TGGTTCAACC GTTCAGAGGC
     AAAAGATCGC GAAATTGTAG CAAAAAAGTT AAGGGACCAT GTTCAGGGTG 701 CTGACAATAA CCCCCTTCTC ATATTTCCTG AAGGGACTTG TGTAAATAAC
     CACTATACTG TGATGTTCAA GAAGGGTGCA TTTGAACTGG GGTGTACCGT 801 TTGCCCAATT GCAATCAAAT ACAATAAAAT TTTTGTTGAT GCATTTTGGA
     ACAGCAGGAA GCAGTCCTTT ACAACGCATC TGCTGCAACT TATGACATCA 901 TGGGCTGTTG TTTTGTGATGT CTGGTACTTG AGCCACAAA ATCTGAGACC
     TGGAGAAACA CCCATTGAGT TTGCAGAGAG GGTCAGGGAC ATAATATCTG 1001 TACGAGCAGG TCTTAAAAAG GTTCCTTGGG ATGGATATCT GAAGTATTCT
     CGCCCTAGCC CAAAACATAG AGAGAGAAAG CAACAAAGCT TGCTGAGTC
```

TABLE 3-continued

All of the novel open reading frame sequences were cloned and expressed in Arabidopsis seeds. The Rc sequences were those found by using the degenerate primers listed in TABLE 2, against the castor bean developing seed cDNA library.

```
1101 AGTGCTACGG CGCCTGGAGG AGAAGTAA

RcLACS4 ORF (2001 bases) (SEQ ID NO: 52)
   1 ATGGCACAAC AGAGGCAGAG AAAGTATTTG ATAGAAGTAG AGAAGGCCAA
     AGAAGCTAAA GATGGAAAGC CATCAGTTGG TCCTGTTTAT CGCAGTCTCT 101 TTGCTAAAGA TGGTTTTCCT CCTCCCATTC CCGGCTTGGA TTCTTGCTGG
     GATGTTTTTC GCATGAGCGT GGAGAAATAT CCTAATAATC CCATGCTTGG 201 TCACCGAGAG TTTGTGAATG GCAAGGCTGG TAAATACGTG TGGCAAACTT
     ACAAACAAGT ATATGATTTG GTCATCAAAG TTGGTAATGC TATACGGAGC 301 TGTGGTGTTG AACCGGGAGA AAAATGTGGT ATTTATGGTG CCAACAGCGC
     TGAGTGGATA ATGAGCATGG AGGCCTGCAA TGCTCACGGG CTTTATTGTG 401 TTCCCTTATA TGACACTTTA GGTGCTGGTG CTGTGGAGTA TATCATATGC
     CATGCCGAGG TCTCAATTGC TTTTGTAGAA GAAAAGAAAA TTCCCGAGCT 501 GTTAAAAACA TTTCCAAGTG CTGCACAATA CATAAAAACA ATTGTGAGCT
     TTGGCAACAT TGCACGGGAA CAAAGAGAAG AGATGGAGAA GTTTGGTTTA 601 GTAGCATATT CTTGGGAAGA CTTTTTTAAA AACTGGGGGG AGAATAAACA
     ATATGATCTC CCAGAGAAAA AGAAAGTGA TATCTGCACT ATAATGTATA 701 CCAGCGGAAC AACTGGCGAT CCGAAGGGAG TAATGATTTC AAATGATAGC
     ATTGTGACCA TTATAGCTGG GGTGAGAAGG CTACTTGAGA GTGTGAATGA 801 ACAGTTGACT TCAGAAGATG TATACCTTTC ATACCTTCCA CTCGCTCATA
     TCTTTGATCG AGTGATTGAG GAGCTATTTA TTTCGCACGG TGCTTCTATA 901 GGGTTCTGGC GAGGGGACGT CAAATTATTA ATTGAAGACA TTGGGGAGCT
     TAAACCAACT ATTTTCTGTG CTGTTCCCCG TGTATTAGAT AGAATACATT 1001 CAGGTTTGAC ACAGAAGATT TCTTCAGGAG GCTTCTTAAA AAACAAATTA
     TTCAATTTAG CATACTCATA CAAACTAAGT TGCATGAAGA AGGGGCTAGC 1101 ACATGATGAG GCATCGCCAC TTTCTGACAA ACTTGTCTTT GATAAGGTAA
     AACAAGGGTT GGGAGGAAAA GTACGGCTTA TTTTATCAGG AGCTGCACCT 1201 CTTGCTATCC ATGTAGAAGC TTTCTTGCGG GTGGTCTCAT GTGCTCATGT
     TTTGCAAGGA TATGGTCTGA CAGAAACCTG TGCTGGCACT TTTGTCTCAC 1301 TACCAAATGA AATGGCAATG CTTGGCACAG TGGGCCCTCC TGTGCCAAAT
     GTGGATGTAT GCCTAGAATC TGTTCCTGAA ATGAATTATG ATGCTCTTTC 1401 AAGCACACCC CGTGGAGAAA TTTGTGTGAG GGGGAGTACT GTCTTTGCTG
     GTTACTACAA ACGAGAAGAC CTCACCAAGG AGGTCCTGAT TGATGGCTGG 1501 TTCCACACAG GTGATATTGG TGAATGGCAA GCAGATGGGA GCTTGAAAAT
     TATTGACCGG AAGAAGAACA TATTTAAACT TCCTCAAGGA GAATATGTTG 1601 CAGTTGAGAA CTTGGAGAAT ATTTATGGTC TTGCTTCTGA TGTTGATTCG
     ATATGGGTTT ATGGGAACAG CTTCGAGTCA TTCCTTGTTG CTGTTGTTAA 1701 CCCCAATAAG CAAGCTCTTG AACATTGGGC ACAAGAGAAT AGTGTGGATG
     GGGACTTCAA ATCCCTTCGC GAAAATCCAA GGGCAAAACA ATATATTATT 1801 GGAGAGCTCA CAAAGATTGG CAAAGAAAAA AAGCTGAAAG GTTTCGAATC
     TATTAAAGCT GTTCATCTTG ATCCTGAGCC ATTTGACATA GAACGTGATC 1901 TCCTCACTCC TACATATAAG AAAAAGAGGC CCCAGTTGCT CAAATACTAC
     CAGAAAGTTA TTGACGACAT GTATAAAAAC GCAAGCAAAC CCAGTGCTTG

2001 A
```

Example 2

Plant Expression Vectors were Constructed

Full length cDNA sequences were amplified out of the full length cDNA library (see TABLE 2 above for primers used) using Pfu Ultra DNA polymerase and cloned into a seed-specific plant expression vector, pOEA2 (DOW Agrosciences).

The restriction sites used for cloning were PstI and XhoI in all cases except for PDAT1A, which had an internal PstI restriction site and AscI was used instead.

The pOEA2 vector contains a multiple cloning site driven by the seed specific promoter, phaseolin (Slightom et al., 1983). A BASTA resistance marker is also present for plant selection as well as a *spectinomycin resistance gene* for selection in *Agrobacteriun tumefaciens* (strain GV3101) and *E. coli* (strain DH10B).

Example 3

Plant Material, Growth Conditions, Transformation and Line Selection

Methods:
*Arabidopsis thaliana*, Columbia (Col-O) ecotype was grown in soil in 4 inch pots maintained at 22° C. under a 16 h day and 8 h night photoperiod in greenhouse conditions.

A marker-less castor bean hydroxylase construct containing the phaseolin (Slightom et al., 1983) seed-specific promoter was developed and used to transform the fae1 *Arabidopsis* mutant line (AC56; Kunst et al., 1992) using the floral dip method (Clough and Bent, 1998). This resulted in a large amount of T1 seed, which was planted on soil and allowed to produce T2 seed. The T2 seed was screened for hydroxy fatty acid content using bulk seed fatty acid analysis. T2 seed from lines containing hydroxy fatty acid was then grown, resulting in T3 seed, amongst these being homozygous lines CL7 and CL37. These two seeds lines were verified to be homozygous for the hydroxylase cDNA by performing single seed fatty acid analysis as well as growing up T3 plants and screening the T4 seed by fatty acid analysis.

The two hydroxylase-expressing *Arabidopsis* lines, CL7 and CL37, were used for testing the effects of the castor bean cDNAs on HFA accumulation. As indicated, the parent for these two lines was the fae1 mutant[20] that is defective in 18-carbon fatty acid elongation. By using fae1, the HFAs 18:1-OH and 18:2-OH cannot be elongated to the respective 20 carbon species, 20:1-OH and 20:2-OH, that are normally present in *Arabidopsis* seeds expressing the hydrolase cDNA, thus simplifying the seed fatty acid profiles. The CL7 and CL37 hydroxylase-containing lines were transformed with *Agrobacteriun tunefaciens* (strain GV3101) containing a cDNA constructs corresponding to one of the cDNA sequences listed in TABLE 3 (SEQ ID NOS:47-52 and SEQ ID NO:53), according to the floral dip method (Clough and Bent, 1998). T1 seeds were harvested and subsequently screened on soil watered with 430 µL/L Finale herbicide (Farnam Companies, Phoenix, Ariz.). The T1 plants that were able to grow under BASTA selection were allowed to produce T2 seed. For detecting the AtDGAT2 transgene (comprising SEQ ID NO:53) in T1 plants, the AtDGAT2 3N2 primer and the phaseolin promoter primer were used. The T2 seed was screened by bulk seed fatty acid analysis and compared to untransformed CL7 and CL37 seed. The lines that contained the RcDGAT2 cDNA were further screened using single seed fatty acid analysis to determine the lines containing one site of cDNA insertion. The lines showing a 3:1 segregation pattern in single seed analysis were then sown on nonselective soil. DNA extraction was performed (Lukowitz et al., 2000) on T2 young leaf material, followed by gene-specific PCR. For detection of the RcDGAT2 cDNA, primers RcDGAT2 5N and RcDGAT2 3' were used (TABLE 2). ExTaq HS polymerase (Takara, Japan) was used for PCR under the following conditions: initial denaturation at 96° C. for 5 minutes followed by 32 cycles of 30 seconds at 94° C., 30 seconds at 58° C., and 1 minute at 72° C., with a final 10 minutes at 72° C. RcDGAT2 CL37 T3 seed was collected and used for seed yield, 100 seed weight, fatty acid, and total lipid analyses.

For line CL7 RcDGAT2, T3 seed from 4 sublines showing the highest hydroxy fatty acid content was sown alongside one subline with the lowest hydroxy fatty acid content. DNA extraction (Lukowitz et al., 2000) was performed on T3 young leaf material, followed by RcDGAT2-specific PCR using the same conditions and primers as above. T4 seed was collected and seed yield, 100 seed weight, fatty acid, and total lipid analyses were performed (see EXAMPLES 4, and 6, respectively below).

Example 4

Castor Bean cDNA Expression in *Arabidopsis*; Seed Yield, 100 Seed Weight, and Lipid Analysis were Determined In addition to fatty acid compositions (discussed in detail below in this EXAMPLE 5), other phenotypic effects were searched for in the lines containing RcDGAT2. Non-fatty acid plant growth characteristics monitored were seedling growth, rosette diameter, time of bolting, and time of flowering. Unlike fatty acid composition, all of these other characteristics were found to be uniform throughout the different lines and were similar to that seen in the neighboring wild-type Columbia plants. Seed yield and 100 seed weight were also determined.
Seed Yield:

Methods. To obtain seed yield, the total seed from each individual plant was harvested and carefully sifted from all other plant materials and placed in its own vial. Each vial of seeds was then carefully weighed before seeds were further used in the present studies.

Results. Seed yield was assayed and compared with parental CL7 and wild-type seed yield. Wild-type Columbia plants were found to produce more seed than both the CL7 and CL7 RcDGAT2 lines. Columbia seed yield levels were about 1.3 g, which was twice the amount of seed found in some of the other lines (FIG. 3).

Figure 3:
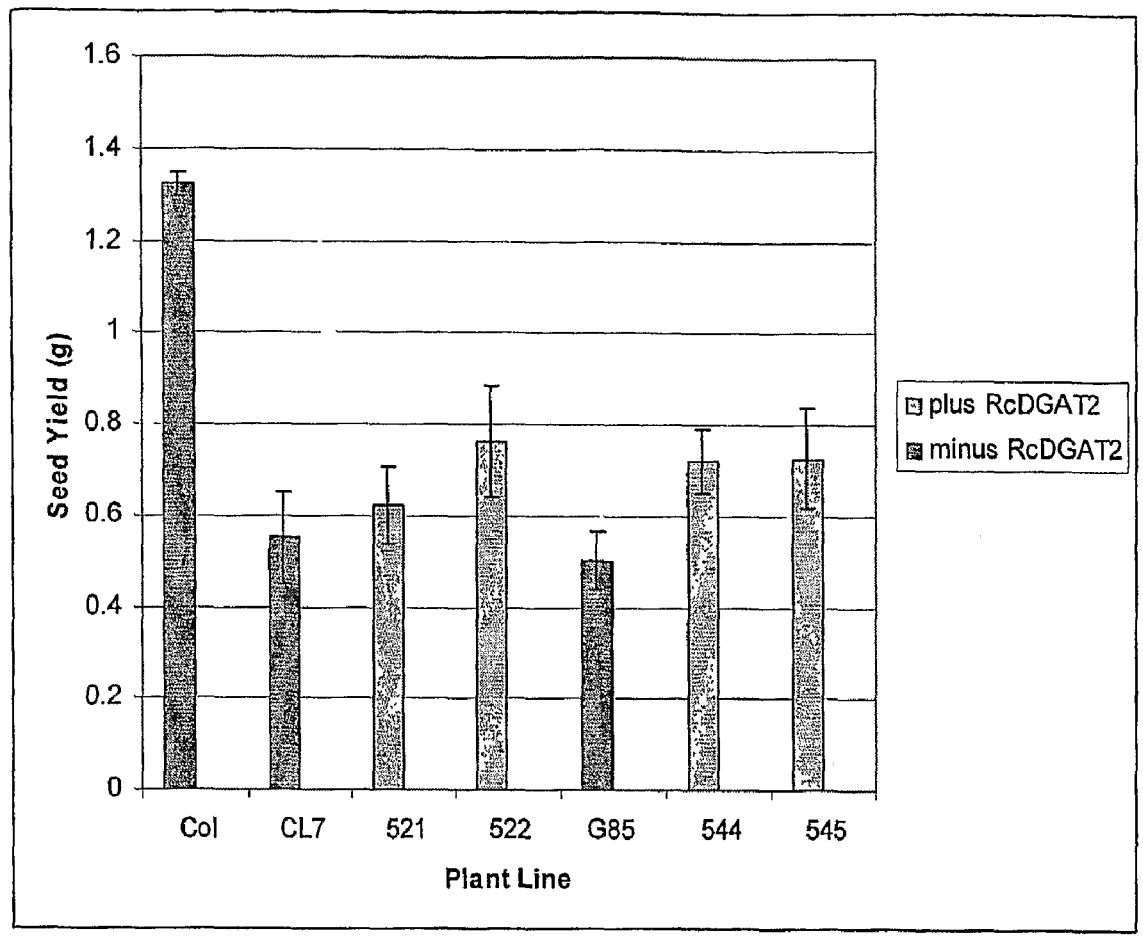
FIG. 3 shows, according to particular aspects of the present invention, a bar graph illustrating seed yield from individual plants, calculated as described hereunder.

Specifically, FIG. 3 shows a bar graph illustrating seed yield from individual plants, calculated as described hereunder. The graph represents the averages of seed yield from six plants of each line, except for Columbia, where only two plants were used. "Col" represents wild-type Columbia plants. CL7 is the parent line that was used for RcDGAT2 transformation. Lines 521 and 522 represent progeny from subline 102 and contain the RcDGAT2 cDNA. Lines 544, 545, and G85 are progeny from subline 104. Lines 544 and 545 contain the RcDGAT2 cDNA, while G85 is a non-RcDGAT2 segregant. In all cases, n=6, except for Col, where n=2. Error bars represent standard error.

When comparing the lines containing RcDGAT2 with the lines not containing RcDGAT2, the seed yield varied from 0.5 g to 0.75 g. The presence of RcDGAT2 into the CL7 background did not seem to increase seed yield.

Although plant growth and appearance were not affected, several seed characteristics were noticed. The same T4 seed lines that were used for the fatty acid analysis above were used for lipid content and 100 seed weight analyses.
100 Seed Weight Analyses:

Methods. To calculate the 100 seed weight, 500 seeds from each separate line were counted out with the aid of the Syngene Bio Imaging System and the software packages Gene Snap and Gene Tools (Synoptics, Cambridge, England). The seed was then weighed and the resulting number of milligrams was divided by 5 to obtain 100 seed weight.

Figure 4:
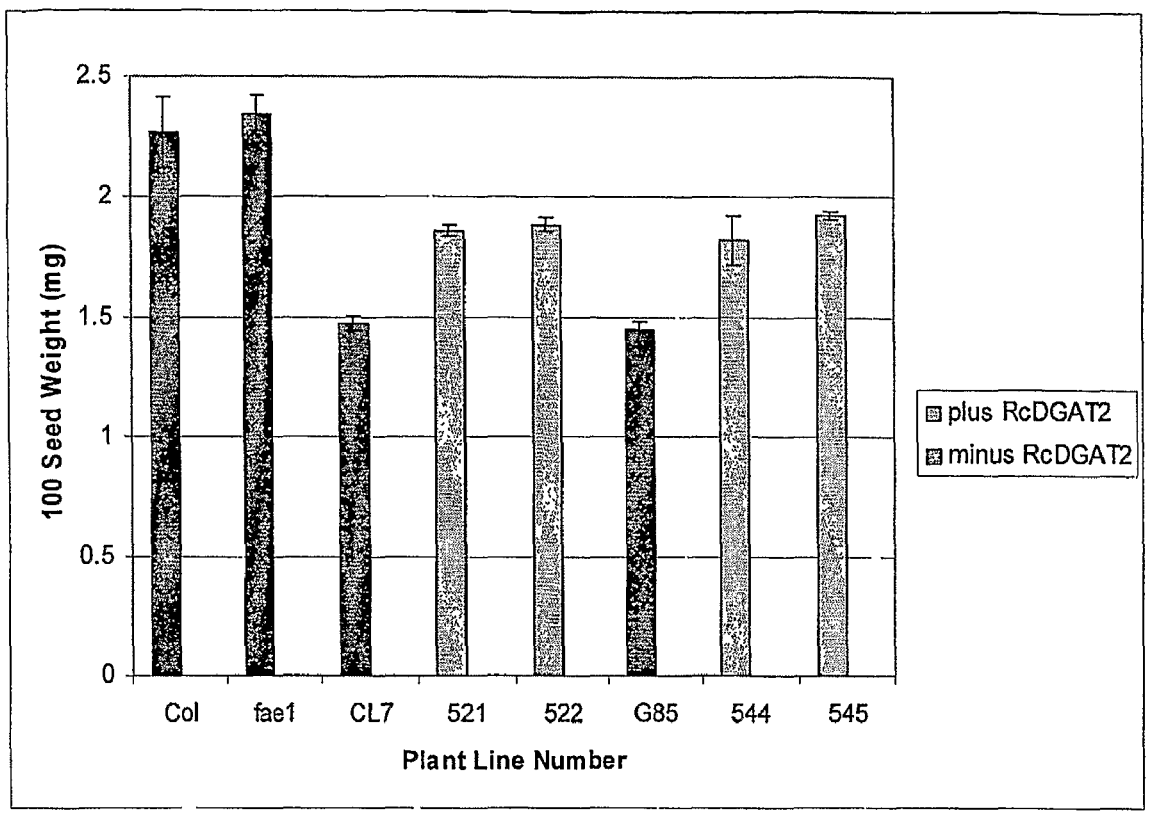
FIG. 4 shows, according to particular aspects of the present invention, a bar graph illustrating '100 seed weight' of RcDGAT2 lines versus non-RcDGAT2 lines. Lines 521 and 522 are sibling RcDGAT2 lines from the subline 102 parent. Lines 544 and 545 are RcDGAT2 sibling lines from the subline 104 parent. Line G85 is a non-RcDGAT2 $T_4$ sibling from the same subline 104 parent as lines 544 and 545. CL7 is the hydroxylase-containing line originally used for RcDGAT2 transformation. In all cases, n=6 except for fae1, where n=2. Error bars represent standard error.

Results. FIG. 4 shows the results from the 100 seed weight analysis. Wild-type Columbia and linefae1 seed was found to weigh about 2.4 mg per 100 seeds. The CL7 parent seed along with the non-RcDGAT2 segregant seed were found to weigh about 1.45 mg per 100 seeds. Although sublines containing RcDGAT2 did not reach the 100 seed weight seen for wild-type seed, levels were found to be almost 30% higher than the CL7 parent and the G85 non-RcDGAT2 segregant. An average of 1.8-1.9 mg was found for these RcDGAT2-containing sublines in comparison to 1.45 mg for non-RcDGAT2 containing lines.

Total Lipid Content:

Methods. Total lipid content was determined by performing quantitative gas chromatography. Exactly 20 seeds were counted and placed in a glass tube with 20 µg 17:0 standard fatty acid. Seeds were then derivatized with the 17:0 fatty acid as above and extracted in 100 µL hexane, with 1 µL being used for injection into the gas chromatograph. Total lipid content was calculated by determining the ratio of the total fatty acid peak area (minus 17:0 standard) to the 17:0 standard peak area and then multiplying this number by 20 µg.

Figure 5:
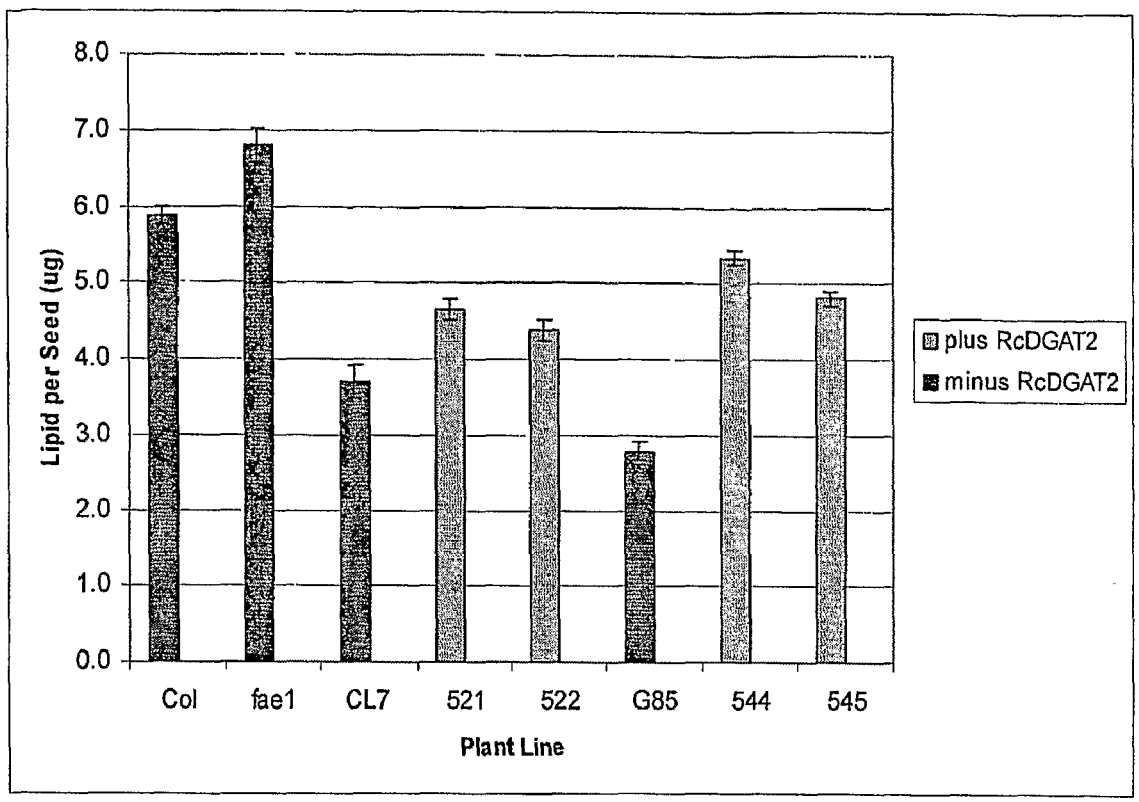
FIG. 5 shows, according to particular aspects of the present invention, a bar graph illustrating seed lipid content based on quantitative gas chromatography. RcDGAT2 CL7 $T_4$ seed from lines 521, 522, 544, and 545 were compared with lines not containing RcDGAT2: G85, CL7, fae1, and wild-type Columbia seed. Experiments were performed in triplicate and the average taken for each line. Error bars represent standard error.

Results. Lipid content of the seed was another seed characteristic demonstrated to be higher in lines containing RcDGAT2 than in lines not containing RcDGAT2. As seen in FIG. 5, the amount of total lipid in lines containing the RcDGAT2 cDNA varied from 4.3 to 5.2 µg per seed. This level was higher than the 2.85 to 3.8 µg per seed seen in line G85 and the CL7 parent. However, in both of these cases, the total lipid content did not reach the levels of wild-type Columbia or the fae1 seed. The levels in these untransformed lines varied from 5.9 to 6.8 µg per seed (FIG. 5).

Example 5

Castor Bean cDNA Expression in *Arabidopsis*; Fatty Acid Compositions and Seed Germination Percentage Were Determined Determination of Fatty Acid Composition:

Methods. The fatty acid composition of seeds was determined by gas chromatography after derivatization with 2.5% (v/v) H2SO4 in methanol for 1 hour (Miquel and Browse, 1992). For bulk seed analysis, 50-100 seeds were used per sample and extracted in 200 µL hexane, with 1 µL used for injection into the gas chromatograph. For single seed analysis, single seeds from each line were placed in individual vials and extracted in 100 µL hexane, with 3 µL being analyzed by gas chromatography for each sample. T2 seed lines showing a 3:1 segregation ratio of high:low hydroxy fatty acid levels were considered to have one transgene insertion site. Both types of samples were run on a 15 m×0.25 mm ID AT-WAX Alltech column (Alltech, Deerfield, Ill.). The gas chromatograph program followed was: initial temperature at 190° C. for 2 minutes followed by a ramp increase of 10° C./min to 230° C. The final temperature was held for 4 minutes.

Results. Both the CL7 and CL37 lines (castor hydroxylase-only *Aradopsis* lines) exhibit 15-18% total hydroxy fatty acid content (18:1-OH+18:2-OH; TABLE 4 below). When compared to the parent fae1 line, an increase in 18:0+18:1 content is observed, a decrease in 18:2 and 18:3 content, and an increase in 16:0 content. This alteration in the fatty acid profile from the parent line is the same trend that was seen by other groups when *Arabidopsis* lines were transformed with the castor bean hydroxylase cDNA (Broun and Somerville, 1997; Smith et al., 2003).

The various castor bean cDNAs were seed-specifically expressed under the phaseolin promoter (Slightom et al., 1983) in lines CL7 and CL37. BASTA herbicide resistance was used as a selectable marker. Initially, RcDGAT1, RcDGAT2, and RcLPAAT1 were expressed in CL7 while RcPDAT1A, RcPDAT1B, and RcLACS4 were expressed in CL37. Upon fatty acid analysis of T2 seed from the transformed lines (TABLE 4), RcDGAT2- and RcPDAT1A-containing lines were both found to have an increase in hydroxy fatty acid content.

In T2 seed, this number was found to be up to 25% hydroxy fatty acid out of the total lipid content. As for RcDGAT1, RcPDAT1B, RcLPAAT1, and RcLACS4, the hydroxy fatty acid levels in the T2 seed were found to be 15-19% (TABLE 4). These levels were similar to the parent line hydroxy fatty acid content. Thus, RcDGAT2 and RcPDAT1A expression caused the most significant increased in hydroxy fatty acid content, and was studied in more detail.

TABLE 4

Bulk Seed fatty acid analysis of $T_2$ seed from hydroxylase lines transformed with different castor bean cDNAs. Shown here are the percentages each fatty acid contributes to the total seed lipid. CL7 was transformed with RcDGAT2, RcDGAT1 or RcLPAAT1. CL37 hydroxylase-containing lines were transformed with RcPDAT1A, RcPDAT1B, or RcLACS4. Four $T_1$ lines, each representing a different transformation event, were grown from the RcDGAT2 transformation. The fatty acid profiles of the resulting $T_2$ seed are represented. For the RcDGAT1 cDNA, six $T_1$ lines were grown. RcLPAAT1 and RcPDAT1A each had three $T_1$ lines grown, and only one line was grown for the RcLACS4 and RcPDAT1B cDNA transformation events.

| Plant Name | 16:0 | 18:0 + 18:1 | 18:2 | 18:3 | 20:1 | 18:1-OH | 18:2-OH | Total OH |
|---|---|---|---|---|---|---|---|---|
| RcDGAT2 #101 | 17.7 | 26.6 | 25.7 | 7.4 | 2.0 | 19.1 | 1.5 | 20.6 |
| RcDGAT2 #102 | 15.5 | 29.7 | 23.0 | 6.7 | 1.6 | 21.0 | 2.5 | 23.5 |
| RcDGAT2 #103 | 14.1 | 34.1 | 20.2 | 5.8 | 1.6 | 21.1 | 3.1 | 24.2 |
| RcDGAT2 #104 | 14.2 | 34.8 | 20.1 | 5.8 | 1.7 | 20.6 | 2.8 | 23.4 |
| RcDGAT1 #101 | 16.0 | 32.9 | 23.1 | 6.8 | 1.5 | 17.5 | 2.1 | 19.6 |
| RcDGAT1 #102 | 14.3 | 38.2 | 21.9 | 5.7 | 1.4 | 15.9 | 2.6 | 18.5 |
| RcDGAT1 #103 | 16.8 | 34.6 | 23.3 | 6.4 | 1.5 | 15.4 | 2.0 | 17.4 |
| RcDGAT1 #104 | 16.1 | 35.9 | 23.3 | 5.9 | 1.4 | 15.3 | 2.0 | 17.3 |
| RcDGAT1 #105 | 14.6 | 37.0 | 21.0 | 6.4 | 1.5 | 16.9 | 2.5 | 19.5 |
| RcDGAT1 #106 | 15.6 | 37.2 | 20.6 | 6.3 | 1.8 | 16.4 | 2.1 | 18.5 |
| RcLPAAT1 #1 | 14.3 | 40.7 | 17.8 | 6.4 | 1.5 | 16.6 | 2.6 | 18.4 |
| RcLPAAT1 #2 | 13.4 | 36.6 | 18.2 | 7.1 | 8.2 | 13.6 | 2.9 | 18.2 |
| RcLPAAT1 #3 | 13.5 | 40.3 | 18.3 | 6.9 | 1.5 | 16.4 | 2.9 | 18.1 |
| RcPDAT1A-C | 11.2 | 35.5 | 21.8 | 7.1 | 0.5 | 19.4 | 4.5 | 23.9 |
| RcPDAT1A-D | 11.8 | 35.1 | 21.6 | 7.2 | 0.5 | 19.3 | 4.4 | 23.8 |

TABLE 4-continued

Bulk Seed fatty acid analysis of $T_2$ seed from hydroxylase lines transformed with different castor bean cDNAs. Shown here are the percentages each fatty acid contributes to the total seed lipid. CL7 was transformed with RcDGAT2, RcDGAT1 or RcLPAAT1. CL37 hydroxylase-containing lines were transformed with RcPDAT1A, RcPDAT1B, or RcLACS4. Four $T_1$ lines, each representing a different transformation event, were grown from the RcDGAT2 transformation. The fatty acid profiles of the resulting $T_2$ seed are represented. For the RcDGAT1 cDNA, six $T_1$ lines were grown. RcLPAAT1 and RcPDAT1A each had three $T_1$ lines grown, and only one line was grown for the RcLACS4 and RcPDAT1B cDNA transformation events.

| Plant Name | 16:0 | 18:0 + 18:1 | 18:2 | 18:3 | 20:1 | 18:1-OH | 18:2-OH | Total OH |
|---|---|---|---|---|---|---|---|---|
| RcPDAT1A-E | 11.5 | 35.1 | 21.2 | 6.2 | 0.5 | 20.9 | 4.6 | 25.5 |
| RcLACS4 A | 17.8 | 36.5 | 23.9 | 6.1 | 0.5 | 15.0 | 0.2 | 15.2 |
| RcPDAT1B | 15.5 | 35.4 | 24.7 | 7.6 | 1.4 | 13.0 | 2.5 | 15.5 |
| CL7 | 12.5 | 44.0 | 19.9 | 5.6 | 1.4 | 12.7 | 3.8 | 16.5 |
| CL37 | 16.0 | 37.3 | 22.4 | 5.5 | 0.4 | 15.2 | 3.1 | 18.3 |
| Col | 9.3 | 16.8 | 29.5 | 20.4 | 23.5 | 0.0 | 0.0 | 0.0 |

RcDGAT2 T4 Seed Fatty Acid Analysis. The transformation of line CL7 with the RcDGAT2 cDNA resulted in a small percentage of T1 seed containing the cDNA. This T1 seed was grown on soil containing BASTA herbicide, allowing only the seed with the selectable marker to grow. The plants that showed resistance to the BASTA herbicide contained one or more than one insertion site.

To determine which plants contained only one insertion site, all of the T1 plants were allowed to set seed. The lines having only one insertion site set seed according to a 3:1 Mendelian segregation of high hydroxy fatty acid (>20%) to parental hydroxy fatty acid (15-18%) levels. Single seed fatty acid analysis was used to determine which T1 plants exhibited this segregation ratio.

TABLE 5 shows two T1 plant lines that exhibited ratios close to 3:1. Subline 162 showed a ratio of 10:3, while subline 104 showed a ratio of 10:6. From these data, it was concluded that sublines 102 and 104 contained single insertion sites.

TABLE 5

Fatty acid profiles of single seeds from sublines 102 and 104 RcDGAT2, in line CL7. Profiles are represented from highest hydroxy fatty acid content to lowest. The thick line in each table represents the putative division point between high hydroxy fatty acid seed and lower hydroxy fatty acid seed.

| | 16:0 | 18:0 + 18:1 | 18:2 | 18:3 | 20:1 | 18:1-OH | 18:2-OH | Total OH |
|---|---|---|---|---|---|---|---|---|
| RcDGAT25 #102 | 15.9 | 25.8 | 21.0 | 7.8 | 3.2 | 21.5 | 4.8 | 26.3 |
| 12 | 15.3 | 27.8 | 22.0 | 6.7 | 2.7 | 20.4 | 5.2 | 25.6 |
| 20 | 15.3 | 24.2 | 24.8 | 7.3 | 3.1 | 20.8 | 4.5 | 25.2 |
| 10 | 18.1 | 28.4 | 20.8 | 6.3 | 1.8 | 20.3 | 4.4 | 24.7 |
| 9 | 13.5 | 35.6 | 18.5 | 5.1 | 2.8 | 19.1 | 5.3 | 24.4 |
| 11 | 18.6 | 23.3 | 24.1 | 7.1 | 2.5 | 20.7 | 3.7 | 24.4 |
| 19 | 19.5 | 25.0 | 21.8 | 6.7 | 2.7 | 20.7 | 3.6 | 24.3 |
| 6 | 19.6 | 23.4 | 25.2 | 7.1 | ~5 | 20.6 | ~2 | 22.6 |
| 16 | 19.4 | 25.1 | 24.0 | ~8 | 8.2 | 18.4 | 4.1 | 22.5 |
| 18 | 17.9 | 27.0 | 22.0 | 7.2 | 3.5 | 18.9 | 3.5 | 22.3 |
| 13 | 16.0 | 42.3 | 19.0 | 4.4 | 1.5 | 12.7 | 4.2 | 16.9 |
| 2 | 15.5 | 41.5 | 21.2 | 4.7 | ~5 | 12.0 | ~3 | 15.0 |
| 1 | 18.1 | 31.7 | 18.8 | 11.3 | 6.8 | 10.9 | 2.5 | 13.4 |
| RcDGAT2 #104 | | | | | | | | |
| 8 | 20.2 | 38.5 | ~20 | 7.9 | ~5 | 28.1 | ~2 | 30.1 |
| 16 | 14.9 | 30.0 | 19.9 | 5.8 | 2.2 | 22.1 | 5.1 | 27.3 |
| 20 | 16.6 | 26.2 | 21.8 | 6.7 | 3.0 | 20.7 | 5.0 | 25.7 |
| 17 | 18.0 | 24.6 | 22.9 | 6.8 | 2.9 | 19.8 | 4.9 | 24.8 |
| 3 | 13.2 | 34.3 | 18.4 | 6.8 | 2.5 | 19.7 | 5.1 | 24.7 |
| 6 | 12.7 | 27.9 | 16.9 | 8.2 | 9.9 | 18.4 | 6.0 | 24.4 |
| 5 | 12.3 | 37.7 | 17.5 | 5.6 | 2.9 | 19.2 | 4.9 | 24.0 |
| 12 | 16.7 | 32.5 | 19.0 | 5.5 | 2.7 | 19.5 | 4.1 | 23.6 |
| 13 | 16.6 | 26.7 | 23.9 | 6.0 | 2.9 | 21.2 | 2.7 | 23.9 |
| 2 | 12.5 | 37.0 | 17.2 | 7.7 | 5.5 | 16.2 | 4.0 | 20.1 |
| 10 | 13.3 | 37.8 | 20.5 | 7.3 | 2.2 | 13.6 | 5.3 | 18.9 |
| 4 | 30.2 | ~35 | ~20 | 11.5 | ~5 | 18.7 | 0.0 | 18.7 |
| 9 | 17.6 | 33.7 | 21.1 | 5.7 | 4.4 | 14.9 | 2.6 | 17.5 |
| 1 | 10.8 | 36.9 | 17.5 | 11.9 | 6.4 | 13.2 | 3.4 | 16.6 |
| 11 | 17.2 | 37.8 | 17.7 | 5.5 | 5.9 | 11.5 | 4.3 | 15.8 |
| 18 | 10.7 | 28.7 | 20.7 | 11.5 | ~5 | 13.0 | 2.8 | 15.8 |

Because the T2 seed of RcDGAT2 segregants showed an increase in hydroxy fatty acid content, a seed population homozygous for RcDGAT2 would most likely show an even further increase. Several lines were grown and homozygous individuals were selected for further propagation. To start, sublines 102 and 104 T2 seed was grown on nonselective soil and T3 seed was allowed to set. RcDGAT2-specific PCR was performed on all of the T2 plant population as well as bulk seed analysis on T3 seed. T3 seed from T2 individuals testing positive for RcDGAT2-specific PCR was sown and T4 seed was allowed to set. This subset consisted of two lines (521 and 522) from subline 102 and two lines (544 and 545) from subline 104. These T3 lines were all found to contain the RcDGAT2 cDNA based on RcDGAT2-specific PCR and were assumed to be homozygous for the RcDGAT2 cDNA. A third line (G85) from subline 104 was grown alongside the above lines. This line was a non-RcDGAT2 segregant, testing negative in RcDGAT2-specific PCR. As controls, the CL7 parent line as well as wild-type Columbia plants were grown under the same conditions adjacent to the above five plant lines.

Once the five sublines produced T4 seed, fatty acid analysis was performed. The four lines containing RcDGAT2 were found to have an increase in bulk seed hydroxy fatty acid levels when compared to their respective T2 parent (FIG. 2).

Specifically, FIG. 2 shows a bar graph illustrating the difference in hydroxy fatty acid content of bulk seed from lines containing RcDGAT2 versus lines without RcDGAT2. Data represented are the averages of 6 sibling lines derived from the same parent, except for Col and fae1, which only had 2 separate seed lines. The averages shown here are the same that were represented in TABLE 5. "Col" represents wild-type Columbia plants. CL7 is the parent line that was used for RcDGAT2 transformation. Lines 521 and 522 are lines containing RcDGAT2 derived from the same $T_1$ parent. Lines 544, 545, and G85 are sibling lines derived from the same $T_1$ parent. Lines 544 and 545 contain the RcDGAT2 cDNA while G85 is a non-RcDGAT2 segregant. Error bars represent standard error.

The highest level attained in bulk seed analysis was found to be 30.8% in plant #2 of subline 544 (TABLE 7A below). This level is ~1.7 times higher than the CL7 parent level of ~18%. On average, levels ranged from 25.9% to 28.5% in the four lines containing RcDGAT2. Levels in G85, the non-RcDGAT2 sibling, were ~16.5%, and CL7 exhibited levels of 18.3%. The average levels in the RcDGAT2 T4 seed was roughly 1.5 times higher in hydroxy fatty acid levels that the average levels of G85 and CL7.

CL37 lines. Likewise homozygous CL37 lines were obtained for the PDAT1A transgene. Data from six representative lines are in TABLE 7B.

TABLE 7B

Seed Fatty Acid compositions of CL37 lines (FAH12) homozygous for the PDAT1A Transgene. The table values are Fatty Acid Composition (percent of total fatty acids).

| Line | 16:0 | 18:0 | 18:1 | 18:2 | 18:3 | 20:1 | 18:1-OH | 18:2-OH | Total OH |
|---|---|---|---|---|---|---|---|---|---|
| D | 11.1 | 6.1 | 22.8 | 18.5 | 5.5 | <1 | 22.8 | 6.3 | 29.1 |
| H | 10.4 | 6 | 24.1 | 16.3 | 5.2 | <1 | 22.4 | 7.5 | 29.9 |
| J | 11.7 | 6.9 | 27.8 | 18.6 | 5.8 | <1 | 22.7 | 6.4 | 29.1 |
| M | 12.2 | 6.2 | 25.6 | 19 | 5.5 | <1 | 24 | 7.5 | 31.5 |
| R | 12.9 | 7.4 | 24.6 | 19.4 | 5.6 | <1 | 23.8 | 6.2 | 30 |
| T | 10.8 | 5.8 | 21.8 | 16.8 | 4.9 | <1 | 22.3 | 7 | 29.3 |

The percent of total fatty acids in the CL37 lines (FAH12) homozygous for the PDAT1A transgene ranged from 29.1% to 31.5%.

Therefore, both RcDGAT2 and RcPDAT1A expression caused the substantial increases in hydroxy fatty acid content, and respective homozygous lines had the highest levels

TABLE 7A

Results of bulk seed gas chromatograph analysis of RcDGAT2 in CL7 $T_4$ seed. This table shows the fatty acid profile of seed from representative sibling lines. This RcDGAT2 CL7 seed was compared with the fatty acid profile of the fae1 mutant parental line and the CL7 line used for RcDGAT2 transformation. Col represents wild-type Columbia seed. Lines 521, 522, 544, and 545 are four different lines that tested positive for RcDGAT2-specific PCR. Line G85 is a non-RcDGAT2 sibling derived from the same $T_1$ parent plant as lines 544 and 545. Six plants from each line were used for these averages, except for Col and fae1, where two plants were used. The averages and standard error represented here were used for the construction of the graph shown in FIG. 2.

| Plant Line | 16:0 | 18:0 | 18:1 | 18:2 | 18:3 | 20:1 | 18:1-OH | 18:2-OH | Total OH | Average | Std Error |
|---|---|---|---|---|---|---|---|---|---|---|---|
| Col #1 | 8.8% | 3.4% | 15.7% | 31.6% | 23.2% | 16.0% | 0.0% | 0.0% | 0.0% | 0.0% | 0.0% |
| Col #2 | 9.1% | 3.2% | 16.4% | 31.5% | 22.9% | 15.4% | 0.0% | 0.0% | 0.0% | | |
| fae1 #1 | 10.1% | 3.4% | 28.6% | 36.9% | 20.2% | 0.3% | 0.0% | 0.0% | 0.0% | 0.0% | 0.0% |
| fae1 #2 | 10.2% | 3.7% | 29.2% | 36.6% | 19.5% | 0.3% | 0.0% | 0.0% | 0.0% | | |

TABLE 7A-continued

Results of bulk seed gas chromatograph analysis of RcDGAT2 in CL7 T$_4$ seed.
This table shows the fatty acid profile of seed from representative sibling lines.
This RcDGAT2 CL7 seed was compared with the fatty acid profile of the fae1 mutant
parental line and the CL7 line used for RcDGAT2 transformation.
Col represents wild-type Columbia seed. Lines 521, 522, 544, and 545 are
four different lines that tested positive for RcDGAT2-specific PCR.
Line G85 is a non-RcDGAT2 sibling derived from the same T$_1$ parent plant
as lines 544 and 545. Six plants from each line were used for these averages,
except for Col and fae1, where two plants were used.
The averages and standard error represented
here were used for the construction of the graph shown in FIG. 2.

| Plant Line | 16:0 | 18:0 | 18:1 | 18:2 | 18:3 | 20:1 | 18:1-OH | 18:2-OH | Total OH | Average | Std Error |
|---|---|---|---|---|---|---|---|---|---|---|---|
| CL7 #1 | 15.8% | 6.9% | 31.8% | 22.0% | 5.4% | 0.4% | 14.7% | 3.1% | 17.7% | 18.3% | 0.1% |
| CL7 #2 | 15.2% | 6.4% | 32.2% | 22.3% | 5.5% | 0.4% | 15.0% | 3.0% | 18.0% | | |
| CL7 #3 | 17.2% | 7.3% | 28.5% | 22.5% | 5.5% | 0.4% | 15.5% | 3.0% | 18.5% | | |
| CL7 #4 | 17.8% | 7.5% | 28.7% | 21.8% | 5.1% | 0.5% | 15.3% | 3.4% | 18.7% | | |
| CL7 #5 | 16.9% | 7.2% | 27.5% | 23.9% | 5.8% | 0.4% | 15.6% | 2.8% | 18.4% | | |
| CL7 #6 | 13.3% | 5.9% | 34.0% | 22.0% | 5.9% | 0.4% | 15.0% | 3.4% | 18.5% | | |
| RcDGAT2 521 #1 | 11.9% | 5.4% | 30.2% | 23.2% | 8.4% | 0.4% | 16.5% | 4.0% | 20.5% | 25.9% | 1.1% |
| RcDGAT2 521 #2 | 12.3% | 5.8% | 26.2% | 21.9% | 7.1% | 0.4% | 21.7% | 4.6% | 26.3% | | |
| RcDGAT2 521 #3 | 12.8% | 6.2% | 25.4% | 20.9% | 6.1% | 0.4% | 23.8% | 4.5% | 28.3% | | |
| RcDGAT2 521 #4 | 12.1% | 5.8% | 27.7% | 20.9% | 6.9% | 0.4% | 21.9% | 4.3% | 26.2% | | |
| RcDGAT2 521 #5 | 13.6% | 6.2% | 21.0% | 23.9% | 7.3% | 0.3% | 23.6% | 4.0% | 27.7% | | |
| RcDGAT2 521 #6 | 11.7% | 5.4% | 28.7% | 21.0% | 6.5% | 0.4% | 21.9% | 4.4% | 26.3% | | |
| RcDGAT2 522 #1 | 13.1% | 6.5% | 23.2% | 22.0% | 6.6% | 0.4% | 23.9% | 4.4% | 28.2% | 27.7% | 0.3% |
| RcDGAT2 522 #2 | 12.3% | 5.6% | 26.7% | 21.0% | 6.1% | 0.4% | 23.6% | 4.4% | 28.0% | | |
| RcDGAT2 522 #3 | 13.1% | 6.0% | 26.1% | 20.8% | 6.0% | 0.4% | 23.9% | 3.8% | 27.7% | | |
| RcDGAT2 522 #4 | 12.7% | 6.0% | 25.4% | 21.5% | 6.5% | 0.4% | 22.9% | 4.6% | 27.5% | | |
| RcDGAT2 522 #5 | 12.0% | 5.8% | 28.4% | 20.5% | 6.5% | 0.4% | 22.0% | 4.5% | 26.5% | | |
| RcDGAT2 522 #6 | 12.4% | 5.6% | 26.3% | 20.6% | 6.3% | 0.4% | 23.9% | 4.6% | 28.5% | | |
| G85 #1 | 15.3% | 6.7% | 31.6% | 22.5% | 5.6% | 0.4% | 14.9% | 2.9% | 17.8% | 16.5% | 0.4% |
| G85 #2 | 16.4% | 7.4% | 32.2% | 21.1% | 5.1% | 0.4% | 14.6% | 2.9% | 17.4% | | |
| G85 #3 | 16.8% | 7.4% | 30.3% | 22.6% | 5.8% | 0.4% | 14.1% | 2.6% | 16.7% | | |
| G85 #4 | 18.4% | 8.0% | 29.3% | 21.2% | 5.1% | 2.1% | 13.5% | 2.5% | 16.0% | | |
| G85 #5 | 18.6% | 8.0% | 29.3% | 20.7% | 4.9% | 2.3% | 13.6% | 2.6% | 16.2% | | |
| G85 #6 | 19.8% | 8.3% | 29.1% | 19.8% | 4.5% | 3.5% | 12.8% | 2.3% | 15.1% | | |
| RcDGAT2 544 #1 | 11.6% | 5.6% | 26.8% | 21.3% | 7.0% | 0.4% | 22.8% | 4.6% | 27.4% | 28.5% | 0.5% |
| RcDGAT2 544 #2 | 12.3% | 5.8% | 22.4% | 21.7% | 6.7% | 0.4% | 26.1% | 4.7% | 30.8% | | |
| RcDGAT2 544 #3 | 11.6% | 5.4% | 26.7% | 21.0% | 6.6% | 0.4% | 23.5% | 4.9% | 28.3% | | |
| RcDGAT2 544 #4 | 12.9% | 6.2% | 23.3% | 22.7% | 7.2% | 0.4% | 22.9% | 4.3% | 27.2% | | |
| RcDGAT2 544 #5 | 11.6% | 5.5% | 26.1% | 21.1% | 6.5% | 0.4% | 24.2% | 4.6% | 28.8% | | |
| RcDGAT2 544 #6 | 11.8% | 5.8% | 25.5% | 21.6% | 6.5% | 0.4% | 24.0% | 4.4% | 28.4% | | |
| RcDGAT2 545 #1 | 12.9% | 6.2% | 21.9% | 23.3% | 7.0% | 0.4% | 24.0% | 4.2% | 28.3% | 27.8% | 0.3% |
| RcDGAT2 545 #2 | 12.6% | 6.0% | 23.2% | 23.3% | 7.0% | 0.4% | 22.9% | 4.5% | 27.5% | | |
| RcDGAT2 545 #3 | 11.8% | 5.3% | 24.8% | 22.6% | 7.4% | 0.4% | 23.1% | 4.7% | 27.8% | | |
| RcDGAT2 545 #4 | 12.3% | 5.3% | 25.2% | 23.0% | 7.1% | 0.4% | 22.7% | 4.2% | 26.8% | | |
| RcDGAT2 545 #5 | 12.8% | 5.9% | 21.7% | 23.0% | 7.1% | 0.4% | 24.7% | 4.5% | 29.2% | | |
| RcDGAT2 545 #6 | 11.5% | 5.2% | 26.5% | 21.8% | 7.4% | 0.4% | 22.3% | 4.9% | 27.2% | | |

Example 6

Verification of Reproducibility of Hydroxy Fatty Acid Increases by Retransformation of RcDGAT2 into *Arabidopsis*)

To verify that the hydroxy fatty acid increase was a consistent trend with the presence of RcDGAT2, the RcDGAT2 cDNA was retransformed into hydroxy fatty acid-producing *Arabidopsis* lines. The CL7 parental line was again transformed with RcDGAT2 in addition to the other hydroxylase-expressing line, CL37. It was decided to use CL37 in addition to CL7 because CL37 did not exhibit the low percent germination seen in CL7, but instead showed germination similar to that seen in Columbia seed. The experiment progressed in a similar manner as performed above. T1 seed was germinated on selective soil, allowing only transgenic seed to grow. The resulting T1 plants were used in RcDGAT2-specific PCR to verify the presence of the RcDGAT2 cDNA. T2 seed was then allowed to set and analyzed for hydroxy fatty acid content. TABLE 8 shows the fatty acid profiles of the T2 seed.

TABLE 8

Fatty Acid Profile of CL37 and CL7 RcDGAT2 T2 Seed. RcDGAT2 was transformed into CL37 and retransformed into CL7. Here are the fatty acid profiles of the bulk $T_2$ seed compared with the profiles of untransformed CL7 and CL37 seed. Seed from three CL37 RcDGAT2 $T_1$ plants and two CL7 RcDGAT2 $T_1$ plants are represented here.

| Sample Name | 16:0 | 18:0 + 18:1 | 18:2 | 18:3 | 20:1 | 18:1-OH | 18:2-OH | Total OH |
|---|---|---|---|---|---|---|---|---|
| CL37 RcDGAT2 #1 | 15.3 | 34.6 | 20.7 | 6.9 | 1.5 | 17.5 | 3.5 | 21.0 |
| CL37 RcDGAT2 #2 | 13.1 | 36.9 | 18.7 | 6.9 | 1.6 | 19.3 | 3.5 | 22.8 |
| CL37 RcDGAT2 #3 | 12.0 | 39.8 | 17.9 | 6.7 | 1.4 | 17.2 | 5.0 | 22.2 |
| CL7 RcDGAT2 #1 | 14.7 | 27.9 | 21.2 | 6.8 | 1.4 | 23.7 | 4.2 | 27.9 |
| CL7 RcDGAT2 #2 | 13.2 | 31.5 | 21.0 | 6.8 | 1.4 | 21.7 | 4.4 | 26.1 |
| CL7 | 12.5 | 44.0 | 19.9 | 5.6 | 1.4 | 12.7 | 3.8 | 16.5 |
| CL37 | 16.0 | 37.3 | 22.4 | 5.5 | 1.4 | 15.2 | 3.1 | 18.3 |
| Col | 9.3 | 16.8 | 29.5 | 20.4 | 23.5 | 0.0 | 0.0 | 0.0 |

Hydroxy fatty acid content was found to reach above 22% in the CL37 background and above 27% in the CL7 background. Because the hydroxy fatty acid increase seen in CL7 was already studied (see EXAMPLE 5 above) to the T4 seed generation, the CL37 seed was only analyzed further.

Single seed analysis was performed on the RcDGAT2 CL37 T2 segregating seed population. This was to determine which of the transgenic lines contained one genomic insertion site. It was found that line #1 had a 21:8 segregation ratio of high hydroxy fatty acid (19.6-30.6) to lower hydroxy fatty acid (14.1-18.7; TABLE-9). This was very close to the 3:1 Mendelian segregation ratio expected and it was assumed that this line contained only one insertion site.

TABLE 9

Single Seed Analysis of CL37 RcDGAT2 #1. Fatty acid profiles of $T_2$ single seeds from subline CL37 RcDGAT2 #1. Profiles are represented from highest hydroxy fatty acid content to lowest. The thick line represents the putative division point between high hydroxy fatty acid seed and lower hydroxy fatty acid seed.

| DGAT2 CL37-14 #1 | 16:0 | 18:0 | 18:1 | 18:2 | 18:3 | 20:1 | 18:1-OH | 18:2-OH | Tot OH |
|---|---|---|---|---|---|---|---|---|---|
| 5 | 10.8% | 5.4% | 27.9% | 19.3% | 5.7% | 0.4% | 27.9% | 2.7% | 30.6% |
| 30 | 15.0% | 7.4% | 25.5% | 18.7% | 6.6% | 0.3% | 23.4% | 3.1% | 26.5% |
| 3 | 15.6% | 7.0% | 25.5% | 19.5% | 6.1% | 0.3% | 23.5% | 2.6% | 26.1% |
| 29 | 12.1% | 9.0% | 26.5% | 22.0% | 5.3% | 0.3% | 23.3% | 1.5% | 24.8% |
| 20 | 14.7% | 7.4% | 28.2% | 18.8% | 6.3% | 0.3% | 21.4% | 2.9% | 24.3% |
| 27 | 14.5% | 8.0% | 30.8% | 17.3% | 5.6% | 0.2% | 21.4% | 2.2% | 23.6% |
| 6 | 13.8% | 7.3% | 31.7% | 17.7% | 5.8% | 0.3% | 20.7% | 2.6% | 23.3% |
| 21 | 19.7% | 8.8% | 10.2% | 29.7% | 7.7% | 1.3% | 21.2% | 1.4% | 22.6% |
| 19 | 13.1% | 6.8% | 30.1% | 18.2% | 7.3% | 1.9% | 18.6% | 4.0% | 22.6% |
| 15 | 17.1% | 10.4% | 23.6% | 18.6% | 7.5% | 0.3% | 21.4% | 1.2% | 22.6% |
| 26 | 13.4% | 7.0% | 33.1% | 16.6% | 7.0% | 0.3% | 19.0% | 3.6% | 22.6% |
| 24 | 12.3% | 5.8% | 36.3% | 17.4% | 5.4% | 0.3% | 19.1% | 3.5% | 22.6% |
| 11 | 13.7% | 5.7% | 31.6% | 20.5% | 6.5% | 0.3% | 19.4% | 2.4% | 21.8% |
| 4 | 12.6% | 6.0% | 35.2% | 18.3% | 6.0% | 0.3% | 18.2% | 3.4% | 21.6% |
| 22 | 12.8% | 6.4% | 35.8% | 16.8% | 6.8% | 0.3% | 17.8% | 3.4% | 21.2% |
| 17 | 15.2% | 8.7% | 29.4% | 17.8% | 7.7% | 0.4% | 18.0% | 2.7% | 20.8% |
| 8 | 10.9% | 5.2% | 41.3% | 16.5% | 5.7% | 0.3% | 16.4% | 3.6% | 20.0% |
| 2 | 11.3% | 5.0% | 40.6% | 16.9% | 6.0% | 0.3% | 16.3% | 3.7% | 19.9% |
| 10 | 12.2% | 7.3% | 36.7% | 16.7% | 6.9% | 0.3% | 15.5% | 4.4% | 19.9% |
| 13 | 11.7% | 4.8% | 38.1% | 18.8% | 6.7% | 0.3% | 16.2% | 3.4% | 19.6% |
| 14 | 12.1% | 3.7% | 42.2% | 16.1% | 5.8% | 0.4% | 17.7% | 2.0% | 19.6% |
| 12 | 13.5% | 4.1% | 34.9% | 21.6% | 6.8% | 0.4% | 17.4% | 1.4% | 18.7% |
| 16 | 11.0% | 3.8% | 43.6% | 16.4% | 6.1% | 0.4% | 16.6% | 2.1% | 18.7% |
| 7 | 11.7% | 3.3% | 42.0% | 18.5% | 5.8% | 0.4% | 15.5% | 2.8% | 18.4% |
| 23 | 12.0% | 4.2% | 36.2% | 22.0% | 7.2% | 0.4% | 15.8% | 2.2% | 18.0% |
| 18 | 21.9% | 11.5% | 13.5% | 26.6% | 7.6% | 1.2% | 16.3% | 1.4% | 17.7% |
| 28 | 13.3% | 7.5% | 38.5% | 17.2% | 5.8% | 0.4% | 15.7% | 1.5% | 17.3% |
| 25 | 14.7% | 5.9% | 33.3% | 24.6% | 6.1% | 0.3% | 13.6% | 1.6% | 15.1% |
| 9 | 18.2% | 4.1% | 12.8% | 35.8% | 14.5% | 0.5% | 13.4% | 0.8% | 14.1% |
| CL37 | 23.1% | 8.5% | 8.2% | 31.8% | 9.1% | 0.9% | 16.9% | 1.6% | 18.5% |

Figure 7:
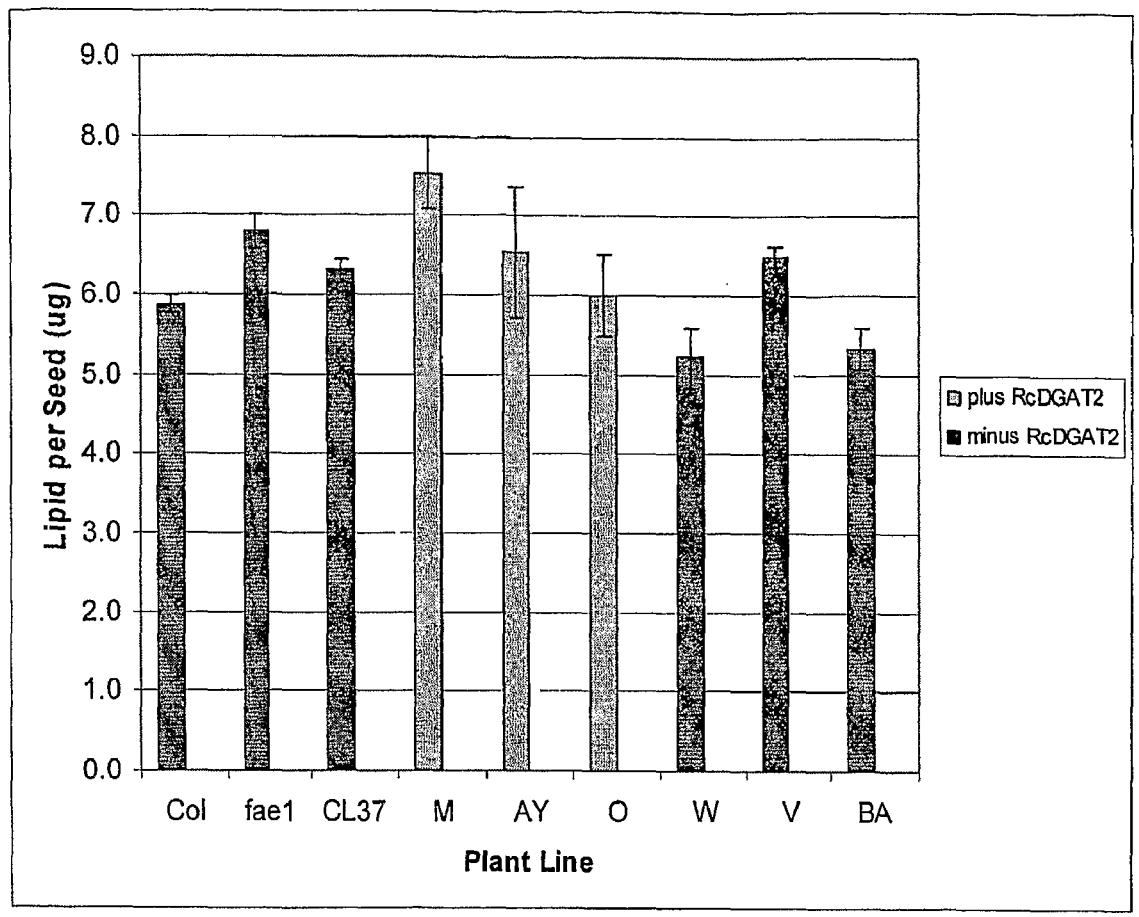
FIG. 7 shows, according to particular aspects of the present invention, total lipid content analysis of CL37 $T_3$ seed based on quantitative gas chromatography. $T_3$ seed from lines containing RcDGAT2 (M, AY, O) were compared with $T_3$ seed from sibling lines not containing RcDGAT2 (W, V, BA). Wild-type Columbia seed along with fae1 and CL7 parent seed were also used in the comparison. Each measurement was taken in triplicate and the average value is represented here. Error bars represent standard error.

This T2 seed line was sown on nonselective soil and allowed to set seed. T2 plants were analyzed for RcDGAT2 presence and subsequent T3 seed fatty acid analysis was completed. When the T3 seed was analyzed, the hydroxy fatty acid content increased to 28.6%, as seen in subline M (TABLE 10). In the interest of time, lines were not pursued to the T4 seed generation and homozygous lines were not determined.

in between that seen in Columbia (5.9 µg lipid per seed) and line fae1 (6.8 µl lipid per seed; FIG. 7). Contrastingly, the presence of the RcDGAT2 cDNA in line CL7 caused an increase in lipid seed content (FIG. 5), bringing levels closer to Columbia seed lipid content. Thus, the RcDGAT2 cDNA was able to increase seed lipid content in a line with low levels (CL7), but may not raise levels in a line with already normal levels (CL37).

TABLE 10

Fatty Acid Profile of CL37 RcDGAT2 $T_3$ Seed Lines. Bulk seed analysis was performed on $T_3$ seed from a $T_2$ segregating plant population. These $T_2$ plants were progeny from the CL37 RcDGAT subline #1 (see TABLE 7). Lines M, O, P, R, S, and T contained RcDGAT2 while lines N and Q did not.

| Plant Name | 16:0 | 18:0 | 18:1 | 18:2 | 18:3 | 20:1 | 18:1-OH | 18:2-OH | Tot OH |
|---|---|---|---|---|---|---|---|---|---|
| RcDGAT2 CL37-M | 9.4% | 3.5% | 31.3% | 19.1% | 7.6% | 0.5% | 21.6% | 7.0% | 28.6% |
| RcDGAT2 CL37-O | 9.5% | 4.3% | 31.1% | 19.0% | 8.8% | 0.4% | 19.3% | 7.6% | 26.9% |
| RcDGAT2 CL37-P | 11.2% | 4.1% | 34.7% | 18.4% | 6.8% | 0.5% | 18.3% | 6.0% | 24.3% |
| RcDGAT2 CL37-R | 11.4% | 3.9% | 35.5% | 21.8% | 7.8% | 0.5% | 13.4% | 5.8% | 19.2% |
| RcDGAT2 CL37-S | 10.7% | 4.1% | 31.1% | 23.8% | 9.3% | 0.5% | 15.2% | 5.4% | 20.6% |
| RcDGAT2 CL37-T | 11.0% | 5.5% | 35.6% | 19.3% | 7.1% | 0.4% | 15.7% | 5.5% | 21.2% |
| RcDGAT2 CL37-N | 10.5% | 4.0% | 40.5% | 19.8% | 6.9% | 0.4% | 12.2% | 5.7% | 17.9% |
| RcDGAT2 CL37-Q | 10.6% | 3.8% | 35.0% | 23.6% | 9.2% | 0.5% | 11.9% | 5.3% | 17.2% |
| CL37-14 | 11.7% | 5.4% | 39.1% | 20.2% | 6.7% | 0.4% | 11.5% | 4.8% | 16.4% |
| Col | 8.5% | 3.1% | 17.1% | 31.3% | 21.6% | 18.1% | 0.0% | 0.0% | 0.0% |

Figure 6:
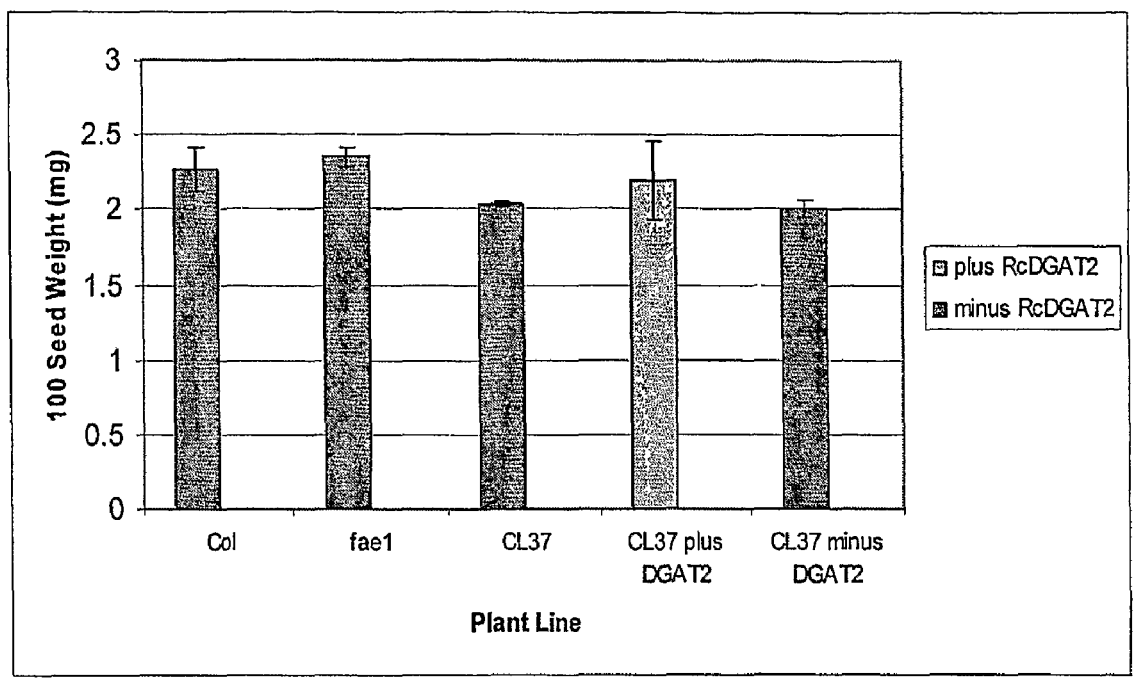
FIG. 6 shows, according to particular aspects of the present invention, a bar graph illustrating '100 seed weight' of RcDGAT2 lines versus non-RcDGAT2 lines. Six lines containing RcDGAT2 were compared with six sibling lines not containing RcDGAT2. These lines were progeny from the same $T_2$ parent (RcDGAT2 CL37 #1—see Table 5). In all cases, n=6, except for CL37, where n=2. Error bars represent standard error.

Since the 100 seed weight and lipid content of RcDGAT2 CL7 seed increased in comparison to the parental seed, these parameters were also measured in the RcDGAT2 CL37 seed. The 100 seed weight of CL37 without RcDGAT2 was found to be less than wild-type Columbia and fae1 seed, which showed about 2.35 mg (FIG. 6). Also, the CL37 RcDGAT2-containing T3 seed was not found to be significantly higher in 100 seed weight than the CL37 not containing RcDGAT2. Although the average of CL37 seed with the RcDGAT2 cDNA was 2.2 mg versus the ~2 mg of the CL37 seed without the RcDGAT2 cDNA, the standard error bars overlapped (FIG. 6). According to these data, it seems that RcDGAT2 does not increase 100 seed weight. This is in contrast to the CL7 seed, where seed containing RcDGAT2 was found to be significantly greater in 100 seed weight than CL7 seed not containing RcDGAT2. However, the CL7 seed without RcDGAT2 was found to be ~1.45 mg (FIG. 4), which was significantly lower than the CL37 seed without RcDGAT2 at ~2 mg. The data indicate that RcDGAT2 indirectly causes an increase in seed weight in lines with very low 100 seed weight levels, but may not have a significant effect on lines having levels close to wild-type levels.

Similarly, total seed lipid content in CL37 lines containing the RcDGAT2 cDNA did not increase from CL37 parental seed levels. Lines containing the RcDGAT2 cDNA, lines M, AY, and O, showed 7.5 µl, 6.6 µg, and 6.0 µg lipid per seed, respectively (FIG. 7). In comparison, the non-RcDGAT2 segregants, lines W, V, and BA, showed 5.2 µg, 6.5 µg, and 5.3 µg lipid per seed, respectively. Based on these data, the presence of the RcDGAT2 cDNA did not seem to cause an increase in the lipid content in the CL37 line. Also, the CL37 line did not show seed lipid content levels lower than Columbia or fael seed as line CL7 did. It displayed 6.3 µg lipid per seed, a level Example 7

Seed Percent Germination was Determined

As the experiments of EXAMPLE 5 with the T4 sublines were performed, it was noticed that the percent seed germination of the CL7 parent was low in comparison to wild-type Columbia seed. Therefore, percent germination studies were performed.

Methods. Seed was sterilized by placing ~50 seeds in an Eppendorf tube with 500 µL bleach solution: 10% bleach, 0.1% SDS, 50% ethanol. Seeds were incubated for 10 minutes on a rotating platform and then washed with 500 µL sterile water 5 times under sterile conditions. Sterile 0.1% agarose was added to disperse the seeds within the tube and then plated on Murashige and Skoog basal medium with sucrose and agar (Sigma, St Louis, Mo.). Plates were incubated at 4° C. for 2 days and then placed at room temperature under a 16 h day and 8 h night photoperiod. After 7-9 days in the light, the number of germinated and ungerminated seeds was counted.

Results. When measured, the percent germination of CL7 seed was found to be ~10% (TABLE 6) as opposed to the 92% germination of Columbia seed. It was also noticed that the sublines containing the RcDGAT2 cDNA had a higher germination percentage than their CL7 parent. The analysis of T3 seed of sublines 521, 522, 544, 545 showed a vast increase in percent germination when compared to their non-RcDGAT2 sibling G85 as well as their CL7 parent. There was an increase in germination from the 10% seen in both G85 and CL7 to an average of 67-83% in the lines containing RcDGAT2.

TABLE 6

T₃ seed germination analysis of seed containing the RcDGAT2 cDNA versus seednot containing the RcDGAT2 cDNA. CL7 was the parental line used for RcDGAT2 transformation. Sublines 521 and 522 were lines from subline 102 and both contained the RcDGAT2 cDNA. Sublines 544, 545, and G85 were progeny from subline 104. Sublines 544 and 545 both contained the RcDGAT2 cDNA, while G85 did not. Germination analysis was performed in duplicate.

|     | Germinated | Total | % Germination | Average |
|-----|------------|-------|---------------|---------|
| Col | 35         | 39    | 89.7%         | 92.1%   |
|     | 51         | 54    | 94.4%         |         |
| CL7 | 5          | 56    | 8.9%          | 10.6%   |
|     | 6          | 49    | 12.2%         |         |

TABLE 6-continued

T₃ seed germination analysis of seed containing the RcDGAT2 cDNA versus seednot containing the RcDGAT2 cDNA. CL7 was the parental line used for RcDGAT2 transformation. Sublines 521 and 522 were lines from subline 102 and both contained the RcDGAT2 cDNA. Sublines 544, 545, and G85 were progeny from subline 104. Sublines 544 and 545 both contained the RcDGAT2 cDNA, while G85 did not. Germination analysis was performed in duplicate.

|     | Germinated | Total | % Germination | Average |
|-----|------------|-------|---------------|---------|
| 521 | 35         | 71    | 49.3%         | 67.0%   |
|     | 33         | 39    | 84.6%         |         |
| 522 | 35         | 60    | 58.3%         | 73.8%   |
|     | 33         | 37    | 89.2%         |         |
| 544 | 42         | 66    | 63.6%         | 77.8%   |
|     | 69         | 75    | 92.0%         |         |
| 545 | 23         | 33    | 69.7%         | 82.5%   |
|     | 62         | 65    | 95.4%         |         |
| G85 | 3          | 47    | 6.4%          | 10.3%   |
|     | 6          | 42    | 14.3%         |         |

Example 8

**AtDGAT2 Overexpression in *Arabidopsis* did not Cause an Increase in Hydroxy Fatty Acid, and did not Exhibit the Same Effect as the RcDGAT2 cDNA**

Because the effects of RcDGAT2 on both CL7 and CL37 showed increased hydroxy fatty acid levels, applicants wanted to determine if this effect was specific to RcDGAT2. The phenomenon exhibited by RcDGAT2 could be a phenomenon exhibited by DGAT2 enzymes in general and not specific to RcDGAT2. For this reason, the AtDGAT2 cDNA (At3g51520) was overexpressed in the CL37 parental line.

Methods. T1 seed was germinated on selective soil and the resistant plants were allowed to set seed. To verify the presence of the transgene (versus the presence of the endogenous AtDGAT2), PCR was carried out on T1 plants using one primer specific to the AtDGAT2 cDNA and one primer specific to the phaseolin promoter. The T2 seed from these plants was used for bulk seed fatty acid analysis.

Results. Six lines with AtDGAT2 transgene incorporation are shown in TABLE 11. The hydroxy fatty acid content of these lines was found to be similar to the level found in CL37. These levels ranged from 15.3% to 18.7% compared to the 17.6% found in the CL37 parent line (TABLE 11). Based on this T2 seed analysis, it was concluded that the AtDGAT2 cDNA did not cause an increase in hydroxy fatty acid and did not exhibit the same effect as the RcDGAT2 cDNA.

TABLE 11

Fatty Acid Analysis of CL37 AtDGAT2 T₂ Seed. AtDGAT2 was transformed into parent line CL37. T₂ seed fatty acid profiles are represented here along with CL37 parental seed, wild-type Columbia seed, and fae1 seed. Analysis was performed in triplicate and the average values are represented here.

| Plant Line | 16:0  | 18:0 | 18:1  | 18:2  | 18:3  | 20:1  | 18:1-OH | 18:2-OH | Total OH |
|------------|-------|------|-------|-------|-------|-------|---------|---------|----------|
| Col        | 9.4%  | 2.5% | 14.0% | 33.9% | 25.1% | 14.9% | 0.0%    | 0.0%    | 0.0%     |
| fae1       | 9.9%  | 3.0% | 26.7% | 37.3% | 22.6% | 0.3%  | 0.0%    | 0.0%    | 0.0%     |
| CL37       | 12.0% | 4.7% | 38.7% | 20.2% | 6.5%  | 0.4%  | 12.1%   | 5.4%    | 17.6%    |
| AtDGAT2 A  | 13.9% | 4.3% | 37.5% | 19.2% | 6.1%  | 0.4%  | 16.0%   | 2.7%    | 18.6%    |
| AtDGAT2 B  | 13.5% | 4.7% | 34.6% | 22.4% | 7.4%  | 0.3%  | 13.3%   | 3.8%    | 17.1%    |
| AtDGAT2 C  | 12.3% | 4.8% | 39.7% | 18.0% | 6.4%  | 0.3%  | 14.0%   | 4.4%    | 18.5%    |
| AtDGAT2 D  | 12.7% | 4.7% | 35.1% | 21.6% | 7.2%  | 0.3%  | 13.1%   | 5.3%    | 18.4%    |
| AtDGAT2 E  | 12.9% | 4.6% | 34.8% | 21.5% | 7.1%  | 0.3%  | 14.5%   | 4.3%    | 18.7%    |
| AtDGAT2 F  | 13.7% | 4.0% | 36.0% | 21.3% | 9.4%  | 0.4%  | 11.9%   | 3.4%    | 15.3%    |

Example 9

RcDGAT2 and AtDGAT2 was Expressed in Yeast Cells; RcDGAT2 cDNA Expression in Yeast Cells Allowed for Efficient Tag Biosynthesis from Diricinolein, which was Much More Efficient than Using Diolein as a Substrate. Also, Atdgat2 Expression in this Yeast Strain Resulted in Activity that is Comparable to the pYES2 Control

The above evidence that RcDGAT2 worked better than AtDGAT2 in vivo was followed by an experiment to test the in vitro effects on TAG production. RcDGAT2 and AtDGAT2 were both overexpressed in *S. cerevisiae* strain H1228, which lacks the yeast DGAT2 gene, DGA1. This gene has been shown to be responsible for most of the TAG accumulation in yeast, and when knocked out, only about 30% TAG remains in the yeast cells (Sandager et al., 2002). The use of this knockout line allowed for a low TAG baseline in the yeast cells and easy detection of TAG accumulation due to RcDGAT2 or AtDGAT2 expression.

Methods. Both the RcDGAT2 and AtDGAT2 cDNA sequences were subcloned into pYES2 (Invitrogen, Carlsbad, Calif.) using the restriction sites KpnI and XhoI. Transformation into the *Saccharomyces cerevisiae* mutant strain H1228 (kindly provided by Sten Stymne and Ulf Stahl; Sandager et al., 2002) was performed using the S.c. Easy Comp Transformation KitM (Invitrogen, Carlsbad, Calif.). As a control, the wild-type yeast strain G175 (also provided by Sten Stymne and Ulf Stahl; Sandager et al., 2002) was used. Cells were grown under uracil selection on SD minimal base with—uracil dropout powder at 30° C. overnight (BD Biosciences, Palo Alto, Calif.). Cells were spun down and resuspended in induction media, SD Gal minimal base with—uracil dropout powder. Cells were allowed to grow overnight before being harvested, washed with sterile water, and then resuspended in 5 mL phosphate buffered saline solution, pH 7.2 (Sigma-Aldrich, St. Louis, Mo.) with an added tablet of complete, mini EDTA-free protease inhibitor cocktail (Roche, Penzberg, Germany). In a 4° C. cold room, cells were lysed with 600 micron glass beads using a tabletop bead-beater for 4 minutes, alternating samples every minute. Unlysed cells and cell debris was separated out by low speed centrifugation (700 g) at 4° C. The supernatant was then pelleted at 100,000 g at 4° C. for 30 minutes. The resulting pellet was resuspended in phosphate buffered saline solution with 20% glycerol. Samples were stored at −80° C. before proceeding with enzyme assay.

DGAT2 activity assay and TLC analysis. Protein was dispersed from the yeast microsomes by sonicating samples on ice for 2 minutes using 30-second cycles. For the assay, 250 μg of protein was added to 120 μM DAG, 18 μM [$^{14}$C] oleoyl-CoA (American Radiolabeled Chemicals, St. Louis, Mo.; diluted 1:10 with cold oleoyl-CoA to make 110,000 dpm), 5 mM ATP, 5 mM CoASH, and 1 mM MgSO4. The volume was brought to a total of 500 μL with phosphate buffered saline solution. Sn-1,2 Diolein, sn-1,2 dilinolein (Nu-Chek, Elysian, Minn.), or sn-1,2 diricinolein (generously provided by Tom McKeon, Turner et al., 2003) were used as the DAG substrate. Assays were performed at 25° C. for 15 minutes with shaking at 100 rev/min. Proceeding with lipid extraction protocol stopped the reaction.

Lipid Extraction. Lipids were extracted as described previously[37]. Briefly for lipid extraction, 3 mL chloroform:methanol (1:2), 1 mL chloroform, and 1 mL HAJRA solution (4 mL: 0.2 M $H_3PO_4$/1 M KCl; Hajra, 1974) were added to the assay tube. Samples were vortexed and centrifuged at 4,000 g to separate phases. The lower phase was extracted into a clean tube while the upper phase was re-extracted with 1 mL chloroform. Samples were then dried down completely under a stream of argon and then dissolved in 100 μL chloroform before loading onto a TLC plate. All 100 μL of the extracted lipid was loaded onto a Si250 TLC plate (J. T. Baker, Phillipsburg, N.J.), which was developed in hexane:ethyl ether:acetic acid (35:70:1.5). The separated fractions were viewed by briefly placing TLC plate in iodine vapor chamber. A plate showing standard fraction migrations was viewed by spraying TLC plates with a lipid charring solution (3% cupric acetate, 8% phosphoric acid) cupric acid and baking plate for 10 minutes at 180° C. Autoradiographic images were taken from the plates by 48-hour exposure on X-Omat Blue XB-1 autoradiographic film (Kodak, Rochester, N.Y.). TAG fractions were scraped and analyzed for radioactivity by scintillation count using 20 mL "Budget Solve" scintillation fluid (Research Products International, Prospect, Ill.) diluted with 1/10 volume of distilled water.

Results. Microsomes from the yeast cells exhibiting the overexpression of RcDGAT2, AtDGAT2, and the pYES2 control vector were isolated alongside the wild-type yeast strain G175. These were used in an enzyme assay using different DAG substrates along with concentrations of ATP, CoASH, and $MgCl_2$. The assays were stopped after 15 minutes by performing a lipid extraction on the reaction. The incorporation of the radioactivity was viewed by running the samples on TLC plates and subsequent exposure to autoradiography film.

Figure 8A:
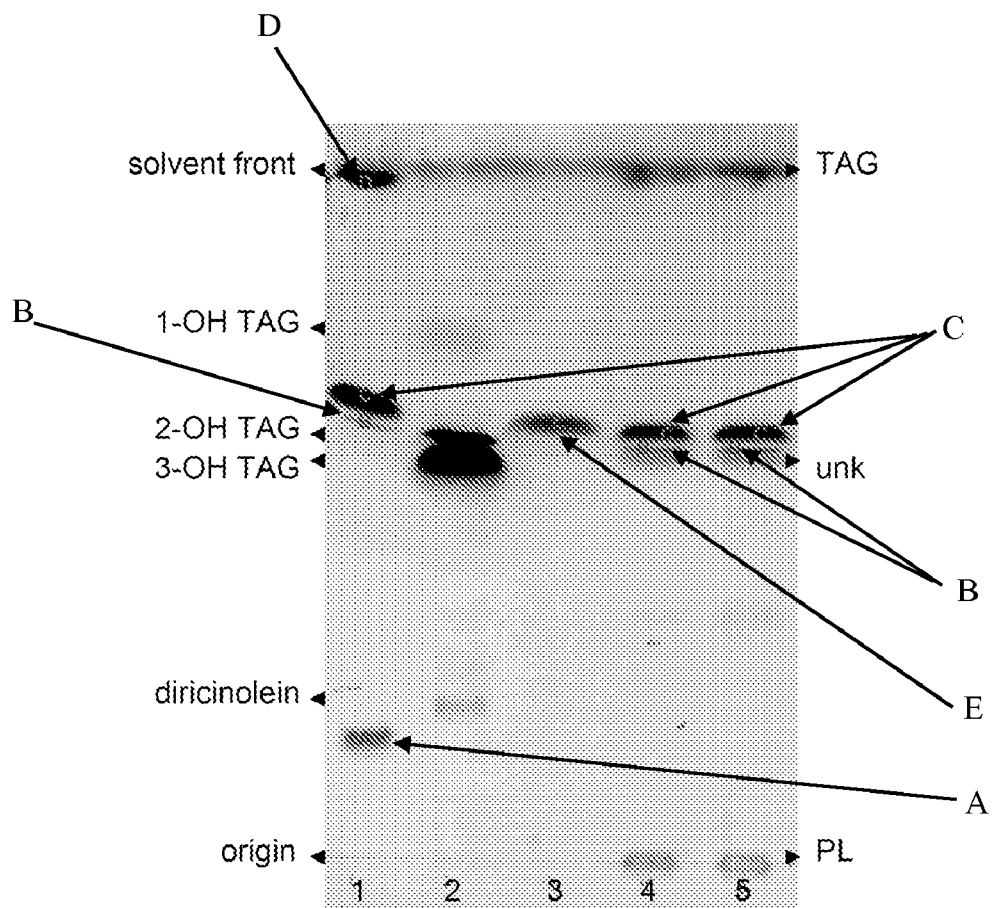
FIG. 8A shows, according to particular aspects of the present invention, enzyme assays conducted on yeast microsomal protein using 120 µM of DAG substrate and 18 µM [$^{14}$C] oleoyl-CoA with 5 mM ATP, 5 m CoASH, and 1 mM MgSO$_4$ for 15 minutes. Lipid fractions were separated by TLC and imaged by autoradiography.
Figure 8B:
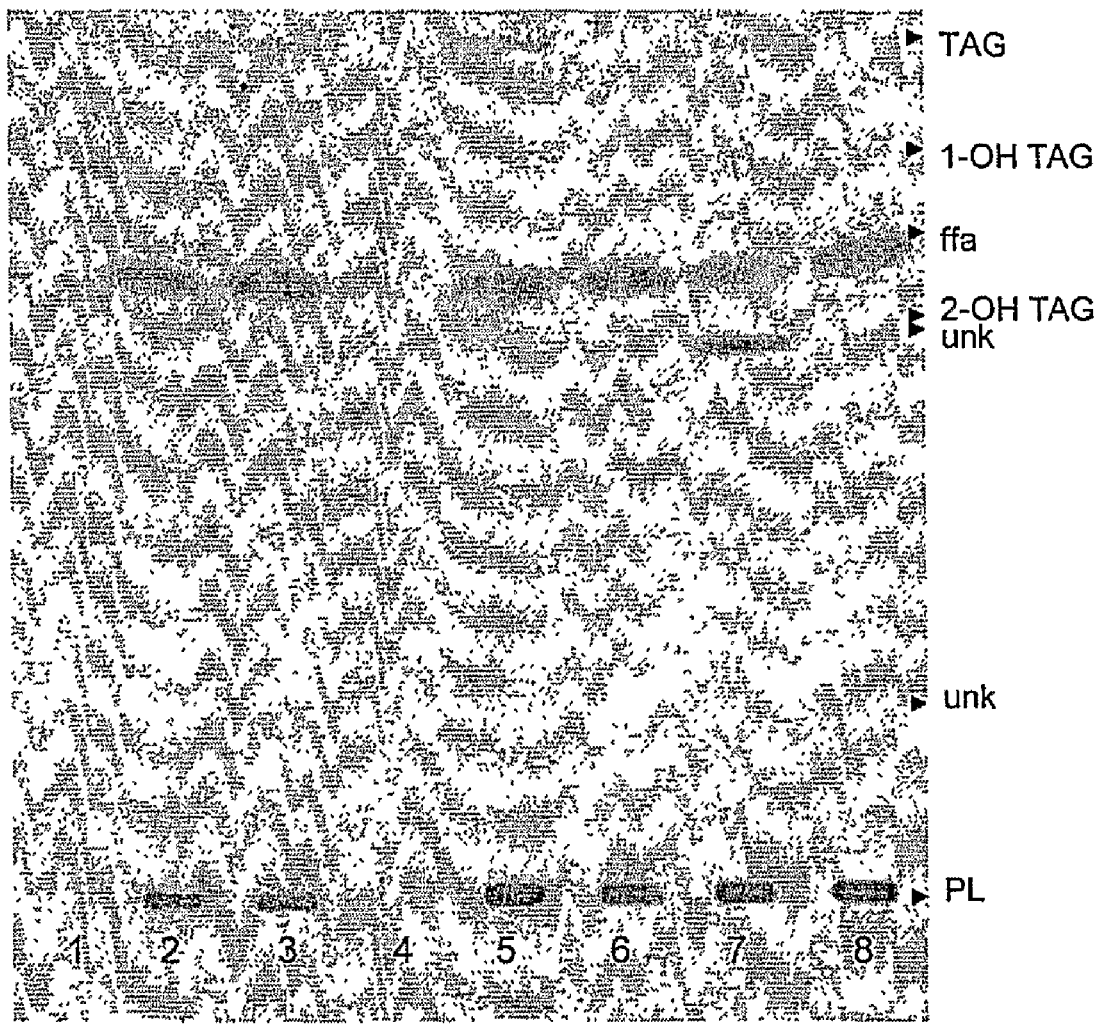
FIG. 8B shows, according to particular aspects of the present invention, an autoradiograph illustrating distribution of radioactivity after enzyme assay.
Figure 8C:
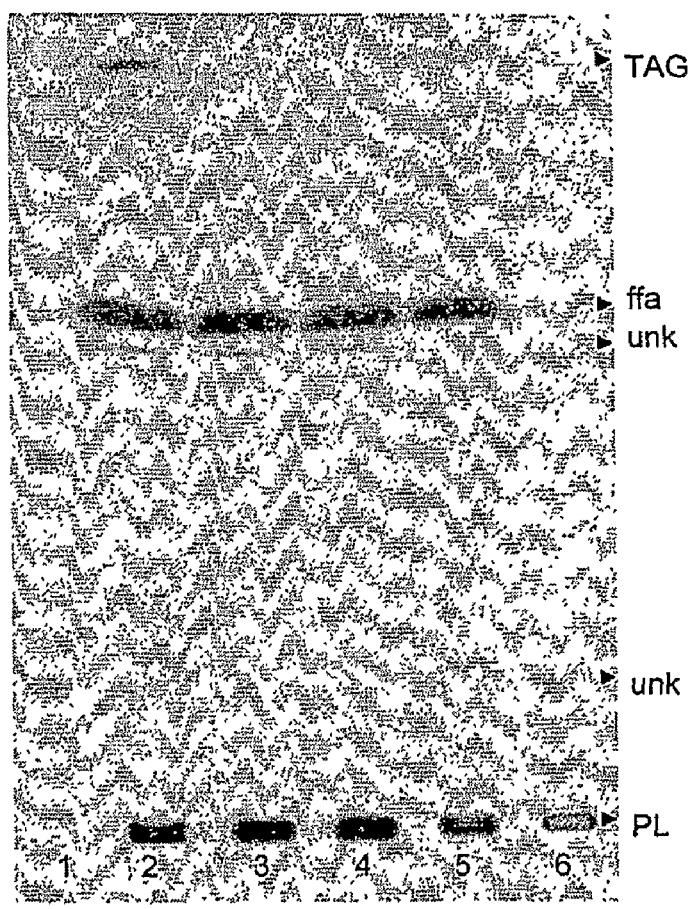
FIG. 8C shows, according to particular aspects of the present invention, and autoradiograph of enzyme assays using dilinolein.

FIG. 8 shows the results of these TLC images, where FIG. 8A shows a picture of a TLC plate that was used to identify the fractions seen in the autoradiographs (FIGS. 8B and 8C). This TLC shows that the oleoyl-CoA in the dilinolein reactions (lanes 4 and 5, FIG. 8A) was hydrolyzed to oleic acid (free fatty acid-ffa).

Specifically, FIG. 8A shows enzyme assays conducted on yeast microsomal protein using 120 μM of DAG substrate and 18 μM [$^{14}$C] oleoyl-CoA with 5 mM ATP, 5 m CoASH, and 1 mM $MgSO_4$ for 15 minutes. Lipid fractions were separated by TLC and imaged by autoradiography. (A) Migration of lipid fractions on TLC plate viewed by baking plate at 180 C after spraying with charring solution. This TLC plate was used to determine the location of the lipid fractions. Lane 1 was loaded with monoolein ("A"), diolein ("B" and "C"), and triolein ("D") standards. Letter "B" represents sn-1,3 diolein (minor fraction) while letter "C" represents the sn-1,2 diolein isomer (major fraction). Lane 2 was loaded with castor oil. The fractions are described to the left of the Figure. Lane 3 shows the migration of 18:1 free fatty acid represented by letter "E." Lane 4 shows the migration pattern of the enzyme assay using dilinolein and yeast microsomes expressing RcDGAT2. Lane 5 shows the pattern for the assay using dilinolein and AtDGAT2-expression yeast microsomes. For lanes 4 and 5, the fractions are described to the right of the Figure. PL=phospholipid fraction; unk=unknown fraction.

Radioactivity was also incorporated into two unknown fractions, which were not present in the negative control (lane 6, FIG. 8C). These unknown fractions were most likely lipid products made in the yeast microsomes by enzymes able to use the radioactive oleoyl-CoA substrate. It is also interesting that the topmost unknown fraction was not as apparent in the wild-type yeast strain assays (lane 3 and lane 5, FIGS. 8B and 8C, respectively). For the purposes of this study, these unknown fractions were disregarded.

For the enzyme assays using either diolein or dilinolein as DAG substrates, enzyme activity was displayed by TAG incorporation. This TAG fraction was easy to view since it separated nicely from the rest of the lipid fractions. For these assays, it can be seen that the yeast microsomes expressing the RcDGAT2 cDNA made the largest amount of TAG (lane 5 and lane 2 in FIGS. 8B and 8C, respectively). The yeast microsomes expressing the AtDGAT2 cDNA (lane 6 and lane 3, FIGS. 8B and 8C, respectively) made very little TAG, similar to the levels seen in the pYES2 control (lane 2 and lane 4, FIGS. 8B and 8C, respectively). The wild-type strain G175 showed TAG synthesis levels (lane 3 and lane 5, FIGS. 8B and 8C, respectively) in between that seen for RcDGAT2 and AtDGAT2.

Specifically, FIG. 8B shows an autoradiograph illustrating distribution of radioactivity after enzyme assay. Lane 1 is unlabeled standard the same as lane 1 in FIG. 8A. Lane 2 shows the migration pattern of the enzyme assay performed with diolein and yeast microsomes expressing pYES2 control vector. Lane 3 is the migration pattern of the enzyme assay performed with diolein and untransformed wild-type yeast strain G175. Lane 4 is the unlabeled castor oil standard the same as used in lane 2 in FIG. 8A. Lanes 5 and 6 show the results from enzyme assays performed with diolein. Lane 5 was loaded with the lipid from the RcDGAT2 enzyme assay and lane 6 was loaded with lipid from the AtDGAT2 enzyme assay. Lanes 7 and 8 were loaded with lipid from the assays performed with diricinolein. Lane 7 represents the RcDGAT2 assay while lane 8 represents the AtDGAT2 assay. Labels on the right of the Figure show radioactivity distribution within each assay. ffa=free fatty acid, 18:1; PL=phospholipid fraction; unk=unknown fraction.

Specifically, FIG. 8C shows an autoradiograph of enzyme assays using dilinolein. Lane 1 is the same unlabeled standard used in lane 1 of FIGS. 8A and 8B. Lane 2 shows the lipid fraction from the assay using RcDGAT2-expressing yeast microsomes. Lane 3 shows the results from the assay performed with AtDGAT2-expressing yeast microsomes. Lane 4 is the lipid fraction from the assay using the mutant strain H1228 expressing the pYES2 control vector. Lane 5 was loaded with the lipid extracted from the enzyme assay using the wild-type yeast strain G175. Lane 6 is lipid from the negative control enzyme assay, which did not have any added microsomal protein. Labels to the right of the Figure show the radioactivity distribution for the enzyme assay. PL=phospholipid fraction; ffa=free fatty acid, 18:1; unk=unknown fraction.

Determining the hydroxy-fatty-acid-containing TAG fractions proved to be more difficult. For the enzyme assays that used diricinolein as a DAG substrate, the activity of the DGAT2 enzymes was determined by detecting the level of TAG containing either one or two hydroxy groups (1-OH TAG and 2-OH TAG, respectively). From FIG. 8A, it was determined that the 2-OH TAG fraction as seen in lane 2 migrated very closely to an unknown fraction and the 1,3 diolein fractions. In the reactions using diricinolein as a DAG substrate (RcDGAT2 and AtDGAT2 reactions only), the autoradiograph image showed only the unknown fraction closely migrating with the 2-OH TAG fraction since the 1,3 diricinolein traveled differently from the 1,3 diolein and did not contain any radioactivity. The 2-OH TAG fraction migrated slightly further than the unknown fraction and can be seen as a very dark band in the RcDGAT2 diricinolein lane (lane 7, FIG. 8B). Also in this lane, a band corresponding with 1-OH TAG can be seen as migrating in between the TAG fraction and the free fatty acid fraction. This is in contrast to the lane containing the lipid from the enzyme assay using AtDGAT2-expressing yeast microsomes. For this assay, there was not a detectable band seen for either 2-OH TAG or 1-OH TAG (lane 8, FIG. 8B). In total, these autoradiographs show that the yeast microsomes expressing the RcDGAT2 cDNA produced the most amount of TAG, whether it was 1-OH or 2-OH TAG for the diricinolein assay or unhydroxylated TAG for the diolein assay.

The activity of the AtDGAT2 and RcDGAT2 enzymes was measured quantitatively by measuring the incorporation of [$^{14}$C] oleoyl-CoA into TAG by scraping the different fractions from the TLC plates. RcDGAT2 was found to form TAG at a rate of 18 μmol/min/mg protein when using diolein and 14 μmol/min/mg when using dilinolein (FIG. 9).

Figure 9:
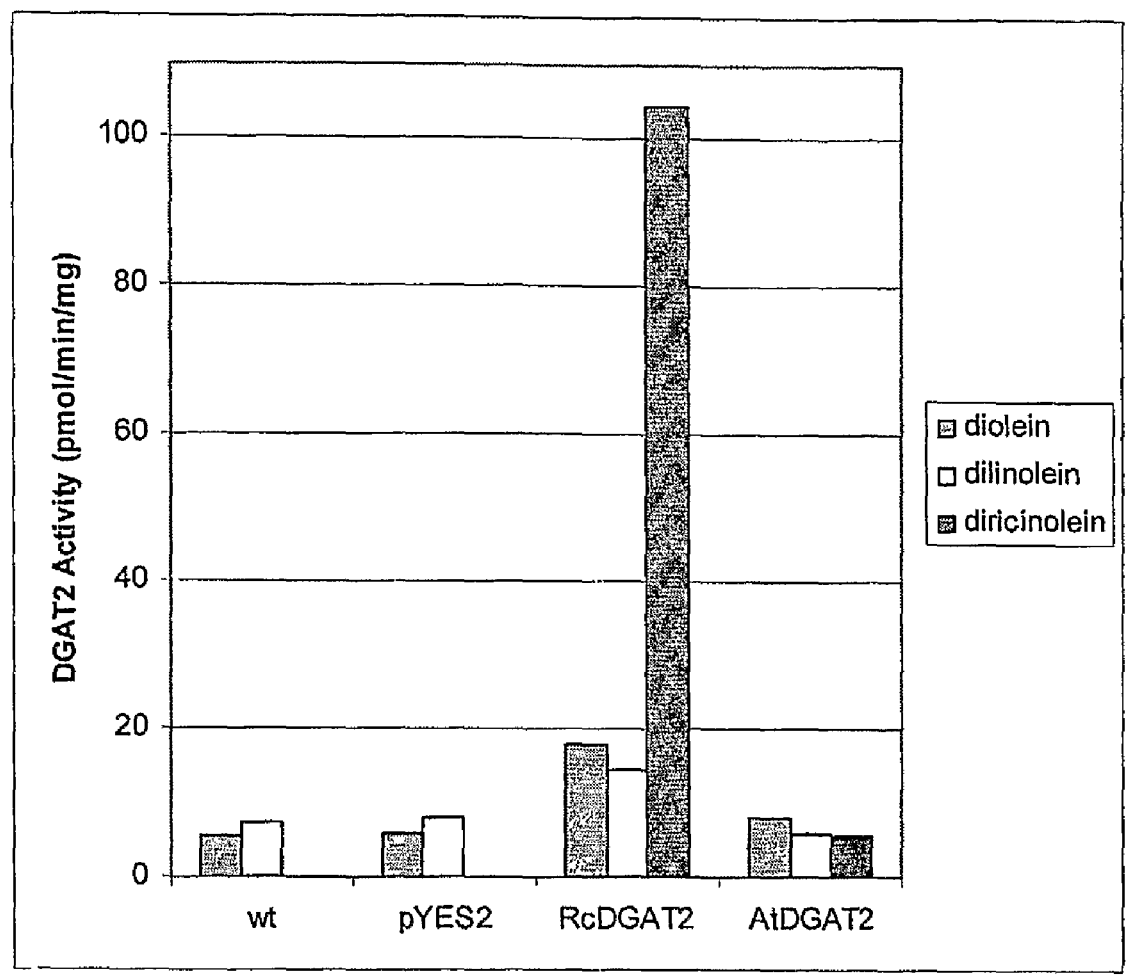
FIG. 9 shows, according to particular aspects of the present invention, rate of TAG synthesis in yeast microsomal preparations from wild-type yeast strain G175, mutant strain H1228 with the pYES2 control vector, and RcDGAT2 or AtDGAT2 in strain H1228.

Specifically, FIG. 9 shows the rate of TAG synthesis in yeast microsomal preparations from wild-type yeast strain G175, mutant strain H1228 with the pYES2 control vector, and RcDGAT2 or AtDGAT2 in strain H1228. Each enzyme assay was conducted using diolein or dilinolein as the DAG substrate along with [$^{14}$C] oleoyl-CoA. For RcDGAT2 and AtDGAT2, diricinolein was also assayed. DGAT activity was measured as the formation of picomoles TAG per minute of enzyme assay per milligram yeast microsomal protein. These data were not standardized to represent gene expression levels.

When using diricinolein, the rate of TAG synthesis was found to increase by 5.75 times, and RcDGAT2 made TAG at a rate above 104 pmol/min/mg protein. The AtDGAT2 enzyme showed levels of TAG formation similar to those seen in the pYES2 control of about 8 pmol/min/mg protein with diolein and 6 pmol/min/mg protein with dilinolein. When using diricinolein as a DAG substrate, its activity remained around that seen for dilinolein of about 6 pmol/min/mg protein. Overall, this assay shows that RcDGAT2 cDNA expression in yeast cells allows for efficient TAG biosynthesis from diricinolein, which is much more efficient than using diolein as a substrate. Also, AtDGAT2 expression in this yeast strain results in activity that is comparable to the pYES2 control.

SUMMARY OF ASPECTS OF WORKING EXAMPLES 1-9

Applicants have applied the concepts of functional genomics to obtain several novel cDNA constructs from castor bean developing seeds, and have expressed these cDNAs in hydroxylase-expressing *Arabidopsis* lines containing hydroxy fatty acid. T2 seed from lines expressing RcDGAT1, RcPDAT1B, RcLACS4, or RcLPAAT1 cDNA was analyzed for fatty acid content. None of these lines displayed an increase in hydroxy fatty acid accumulation. On the other hand, expression of RcDGAT2 or RcPDAT1A was found to increase hydroxy fatty acid accumulation in the T2 seed to a level of ~25% (TABLE 4). RcDGAT2 lines were analyzed in detail in subsequent generations.

Lines homozygous for the RcDGAT2 cDNA were allowed to grow to T4 seed, where the increase in hydroxy fatty acid was found to reach 30% accumulation (TABLE 7); that is, expression of RcDGAT2 increased HFA accumulation by 50-70% compared to parental lines expressing the castor fatty acid hydroxylase alone. This increase in hydroxy fatty acid was also found to be a repeatable occurrence when RcDGAT2 was retransformed into line CL7 and transformed into line CL37. Overall, these data demonstrate that RcDGAT2 expression drives more hydroxy fatty into TAG than the endogenous AtDGAT2 enzyme. These results also show that the *Arabidopsis* seed lipid biosynthesis pathway (FIG. 1) can be manipulated to produce more hydroxy fatty acid than was found in previous attempts (e.g., Broun et al., 1997; Smith et al., 2003). By the addition of RcDGAT2, the *Arabidopsis* lipid biosynthesis pathway becomes substantially more efficient at hydroxy fatty acid production and more comparable to castor bean lipid synthesis.

According to additional aspects of the present invention, DGAT2, PDAT1 and other co-evolved enzymes of species with high levels of novel fatty acids, such as castor, *Crepis* sp., and *Euphorbia lagascae*, which produce hydroxy-, acetylenic-, and epoxy-fatty acids, respectively, may be used to drive overexpression of the respective novel fatty acids, in plants and oilseeds that do not produce the novel fatty acids (such as soybean which contains only the typical fatty acids 16:0, 18:0, 18:1, 18:2, and 18:3).

The overexpression of RcDGAT2 was also found to be better at driving hydroxy fatty acid into TAG than overexpression of the AtDGAT2 cDNA. RcDGAT2 expression was driven by the phaseolin promoter, allowing for expression during lipid synthesis at a level much higher than that of the endogenous AtDGAT2. By the overexpression of AtDGAT2 using the same promoter and *Arabidopsis* lines, it was shown that an increase in hydroxy fatty acid could only by achieved with RcDGAT2. Seed that overexpressed the AtDGAT2 cDNA showed the same fatty acid profile as the parental seed line. These data confirmed this aspect of applicants' conception, by showing that RcDGAT2 was better adapted than AtDGAT2 at driving the production of TAG from a substrate containing ricinoleic acid. The strong preference of yeast-expressed RcDGAT2 for diricinolein DAG verifies the in vivo data from plants, and substantially supports broad application of RcDGAT2 and other DGAT2 enzymes in metabolic engineering projects in a broad class of plants (e.g., oil producing plants, and seed oil plants, etc.), and further in organisms such as yeast.

When the RcDGAT2 and AtDGAT2 cDNAs were expressed in yeast microsomes, RcDGAT2 was found to exhibit high TAG formation when using diolein as the DAG substrate. The formation of TAG was found to increase by almost six fold (FIG. 9) when diricinolein was used as the DAG substrate. Again, even in the context of a diverse organism such as yeast, this data provides substantial further evidence that RcDGAT2 has evolved to be very efficient at driving hydroxy fatty acid into the seed TAG pool, and supports a broad applicability of aspects of the invention in broad variety of organisms (e.g., yeast) and plants, for example in a broad variety of oil plants and seed oil plants.

Significantly, the TAG formation for the AtDGAT2 enzyme was close to the levels found in the control. This could be due to a lack of cDNA expression in the yeast cells, but a more suitable explanation is that the enzyme is inefficient in TAG production. Lardizabal et al. (2001) found similar results when they expressed the AtDGAT2 cDNA in insect cells along with other DGAT2 cDNAs. Although they did not check for the presence of a gene product, they found that the AtDGAT2 enzyme activity was only slightly higher than their control and that it was the lowest TAG producer out of the seven DGAT2 genes assayed. If AtDGAT2 is a poor TAG producer, this would explain why an increase in seed hydroxy fatty acid was not seen when the AtDGAT2 cDNA was overexpressed in the *Arabidopsis* lines.

Figure 10:
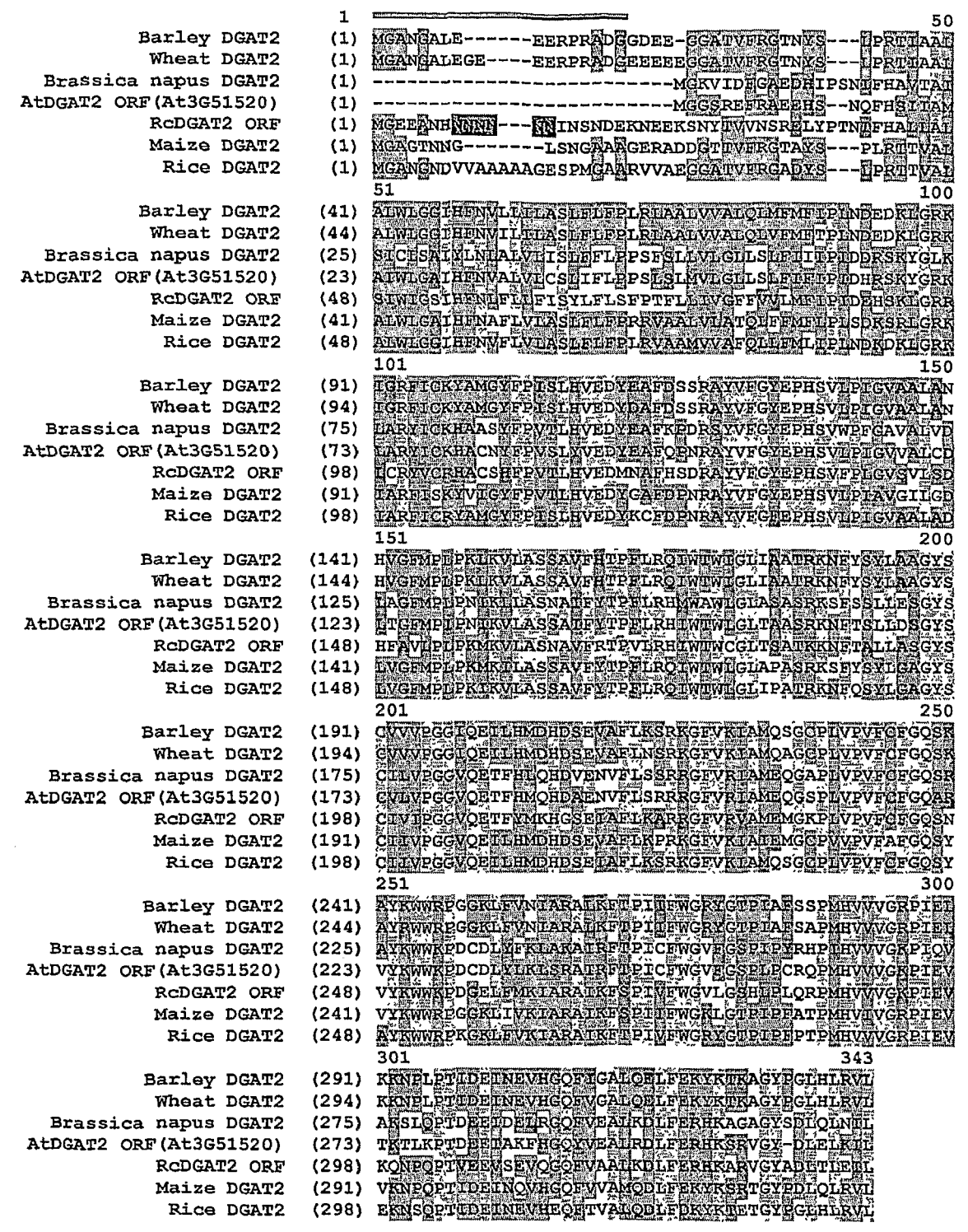

To address the ability of RcDGAT2 to produce TAG from diricinolein at such a high rate, The RcDGAT2 protein sequence was studied. FIG. 10 shows the amino acid alignment of RcDGAT2 with AtDGAT2 along with some other common plant species' DGAT2 sequences. Applicants noted from this alignment that both the *Arabidopsis* and *Brassica napus* have protein sequences that lack upstream sequences that are present in other plant proteins. Without being bound by mechanism, the missing N terminus sequence may necessary for function, and the truncated N terminus may contribute to the low AtDGAT2 activity seen in vitro.

A further point of interest is the string of asparagine residues seen on the N terminus in the RcDGAT2 protein sequence. This string of 6 asparagines may be important for its ability to use diricinolein as a substrate and the reason for it not appearing in any of the other plant protein sequences. This sequence was confirmed by amplifying, cloning, and sequencing the corresponding region of the castor genome

```
(AGTTTTGAGC ACTGAGCACT GAATAGCAAG AAGAAGAAGA

AGAAGAAATG GGGGAAGAAG CGAATCATAA TAATAATAAT

AATAATATCA ATAGTAATGA TGAGAAGAAT GAAGAGAAAT

CAAATTATAC AGTTGTAAAT TCGAGAGAAC TATACCCAAC

GAACATATTT CACGCACTGT TAGCGTTGAG CATATGGATT

GGTTCAATCC ATTTCAATCT CTTCTTACTC TTCATCTCTT

ATCTCTTCCT TTCTTTTCCC ACATTCCTCC TGTTAGTTAC

TCCTCCTCCT TCTCCTTCAT TTTTCTACTA TTTTTGTTTA

TTTATTTTTT AAGACATGAT TAACTATCAA TTTGTTTCTT

TCTGTTTTTT GAAGGATTGT TGGATTTTTT GTGGTGTTAA

TGTTCATTCC CGA; SEQ ID NO: 68)
```

RcPDAT1A also increased hydroxy fatty acid accumulation in transgenic *Arabidopsis* seeds (TABLE 4). Perhaps RcPDAT1A has evolved to drive hydroxy fatty acid into TAG as efficiently as RcDGAT2. Dahlqvist et al. (2000) found high PDAT activity in castor bean developing seed microsomes. Thus, the contribution of PDAT in making ricinoleic acid-containing TAG may be quite high. In the data from this study, RcPDAT1B cDNA expression did not increase hydroxy fatty acid levels in *Arabidopsis* lines, while expression of the RcPDAT1A cDNA did (TABLE 4). Due to this, it is most likely that RcPDAT1A would be the PDAT responsible for this TAG synthesis seen in castor bean microsomes (Dahlqvist et al., 2000). However, when RcPDAT1A was expressed in the hydroxylase *Arabidopsis* lines, T2 seed hydroxy fatty acid levels did not surpass that of the lines expressing RcDGAT2 (TABLE 4). Perhaps if further generations were studied as they were for the RcDGAT2, higher hydroxy fatty acid accumulation would be seen.

According to further aspects of the present invention, multiple coordinate (e.g., castor derived) enzymes may be used (in addition to hydroxylase, RcPDAT1A and RcDGAT2) to boost hydroxy fatty acid content even further.

REFERENCES

Abbott T P, Dierig D A, Foster M, Nelson J M, Coates W, Frykman H B, Carlson K D, Arquette J D (1997) "Status of *Lesquerella* as an Industrial Crop" Inform 8: 1169-1175.

Bafor M, Smith M A, Jonsson L, Stobart K, Stymne S (1991) "Ricinoleic Acid Biosynthesis and Triacylglycerol Assembly in Microsomal Preparations From Developing Castor-Bean (*Ricinus communis*) Endosperm" Journal of Biochemistry 280: 507-514.

Broadwater J A, Whittle E, Shanklin J (2002) "Desaturation and Hydroxylation: Residues 148 and 324 of *Arabidopsis* FAD2, In Addition to Substrate Chain Length, Exert a Major Influence in Partitioning of Catalytic Specificity" Journal of Biological Chemistry 277: 15613-15620.

Broun P, Bodupalli S, Somerville C (1998) "A Bifunctional Oleate 12-Hydroxylase: Desaturase From *Lesquerella fendleri*" The Plant Journal 13: 201-210.

Broun P, Somerville C (1997) "Accumulation of Ricinoleic, Lesquerolic, and Densipolic Acids in Seeds of Transgenic *Arabidopsis* Plants That Express a Fatty Acyl Hydroxylase cDNA from Castor Bean." Plant Physiology 113: 933-942.

Broun P, Shanklin J, Whittle E, Somerville C (1998) "Catalytic Plasticity of Fatty Acid Modification Enzymes Underlying Chemical Diversity of Plant Lipids" Science 282: 1315-1317.

Campbell and Company (2002) "Castor Oil & Castor Oil Derivatives" Franklin Web Publishing, 20 Apr. 2005 10:53 am<http://www.campbell-uv.com/castor.html>.

Carninci P, Hayashizaki Y (1999) "High-Efficiency Full-Length cDNA Cloning" Methods in Enzymology 303: 19-44.

Clough S J, Bent A F (1998) "Floral Dip: A Simplified Method for *Agrobacterium*-mediated transformation of *Arabidopsis thaliana*" Plant Journal 16: 735-743.

Dahlqvist A, Stahl U, Lenman M, Banas A, Lee M, Sandager L, Ronne H, Stymne S (2000) "Phospholipid:Diacylglycerol Acyltransferase: An Enzyme that Catalyzes the Acyl-CoA-Independent Formation of Triacylglycerol in Yeast and Plants" Proc. Natl. Acad. Sci. 97: 6487-6492.

Galliard T, Stumpf P K (1966) "Fat Metabolism in Higher Plants XXX. Enzymatic Synthesis of Ricinoleic Acid By a Microsomal Preparation From Developing *Ricinus communis* Seeds" Journal of Biological Chemistry 241: 5806-5812.

Hajra A K (1974) "On the Extraction of Acyl and Alkyl Dihydroxyacetone Phosphate from Incubation Mixtures" Lipids 9: 502-505.

Hayes D G, Kleiman R, Phillips B S (1995) "The Triglyceride Composition, Structure, and Presence of Estolides in the Oils of *Lesquerella* and Related Species" Journal of American Oil Chemists Society 72: 559-569.

Jako C, Kumar A, Wei Y, Zou J, Barton D L, Giblin M, Covello P S, Taylor D C (2001) "Seed-Specific Over-Expression of an *Arabidopsis* cDNA Encoding a Diacylglycerol Acyltransferase Enhances Seed Oil Content and Seed Weight" Plant Physiology 126: 861-874.

Kunst L, Taylor D C, Underhill E W (1992) "Fatty Acid Elongation in Developing Seed of *Arabidopsis thaliana*" Plant Physiology and Biochemistry 30: 425-434.

Lardizabal K D, Mai J T, Wagner N R, Wyrick A, Voelker T, Hawkins D J (2001) "DGAT2 is a New Diacylglycerol Acyltransferase Gene Family" Journal of Biological Chemistry 276: 38862-38869.

Lin J T, Woodruff C L, Lagouche O J, McKeon T A, Stafford A E, Goodrich-Tanrikulu M, Singleton J A, Haney C A (1998) "Biosynthesis of Triacylglycerols Containing Ricinoleate in Castor Microsomes Using 1-Acyl-2-oleoyl-sn-glycero-3-phosphocholine as the Substrate of Oleoyl-12-hydroxylase." Lipids 33: 59-69.

Lukowitz W. Gillmor C S, Scheible, W-R (2000) "Positional Cloning in *Arabidopsis*. Why It Feels Good to Have a Genome Initiative Working for You" Plant Physiology 123: 795-806.

Miquel M, Browse J (1992). "*Arabidopsis* Mutants Deficient in Polyunsaturated Fatty Acid Synthesis" Journal of Biological Chemistry 267: 1502-1509.

Moreau R A, Stumpf P K (1981) "Recent Studies of the Enzymatic Synthesis of Ricinoleic Acid by Developing Castor Beans" Plant Physiology 67: 672-676.

Osava, M (2001) "Energy in a Castor Bean" Tierramerica, 20 Apr. 2005 11:03 am<http://www.tierramerica.net/2003/0526/ianalisis.shtml>.

Sandager L, Gustavsson N H, Stahl U, Dahlqvist A, Wiberg E, Banas A, Lenman M, Ronne H, Stymne S (2002) "Storage Lipid Synthesis Is Non-essential in Yeast" Journal of Biological Chemistry 277: 6478-6482.

Slightom J L, Sun S M, Hall T C (1983) "Complete Nucleotide Sequence of a French Bean Storage Protein Gene: Phaseolin" Proc. Natl. Acad. Sci. 80: 1897-1901.

Smith M A, Moon H, Chowrira G, Kunst L (2003) "Heterologous Expression of a Fatty Acid Hydroxylase Gene in Developing Seeds of *Arabidopsis thaliana*" Planta 217: 506-517.

Smith M A, Jonsson L, Stymne S, Stobart K (1992) "Evidence for Cytochrome b5 as an Electron Donor in Ricinoleic Biosynthesis in Microsomal Preparations from Developing Castor Bean (*Ricinus communis* L)." Biochem J 287: 141-144.

Sperling P, Linscheid M, Stocker S, Muhlbach H-P, Heinz E (1993) "In Vivo Desaturation of cis-□9-Monounsaturated to cis-□9,12-Diunsaturated Alkenylether Glycerolipids" Journal of Biological Chemistry 268: 26935-26940.

Turner C, He X, Nguyen T, Lin J T, Wong R Y, Lundin R E, Harden L, McKeon T (2003) "Lipase-Catalyzed Methanolysis of Triricinolein in Organic Solvent to Produce 1,2 (2,3)-Diricinolein" Lipids 38: 1197-1206.

Van de Loo F J, Broun P, Turner S, Somerville C (1995) "An Oleate 12-Hydroxylase from *Ricinus communis* L. is a Fatty Acyl Desaturase Homolog." Proc. Natl. Acad. Sci. 92: 6743-6745.

ADDITIONAL REFERENCES

1. Caupin, H-J. Products from Castor Oil: Past, Present, and Future. in *Lipid Technologies and Applications* (eds. Gunstone, F. D. & Padley, F. B.) Marcel Dekker, New York, N.Y., USA 787-795 (1997)

2. Atsmon, D. Castor. in *Oilcrops of the World, Their Breeding and Utilization*. (eds. Robbelen, G., Downey, R. K. & Ashri, A.) McGraw-Hill, New York, N.Y., USA 438-447 (1989).

3. Bafor, M., Smith, M. A., Jonsson, L., Stobart K., & Stymne S Ricinoleic acid biosynthesis and triacylglycerol assembly in microsomal preparations from developing castor-bean (*Ricinus communis*) endosperm. *J Biochem.* 280, 507-514 (1991).

4. Galliard, T. & Stumpf, P. K. Fat metabolism in higher plants X. Enzymatic synthesis of ricinoleic acid by a microsomal preparation from developing *Ricinus communis* seeds. *J. Biol. Chem.* 241, 5806-5812 (1966).

5. Moreau, R. A. & Stumpf, P. K. Recent studies of the enzymatic synthesis of ricinoleic acid by developing castor beans. *Plant Physiol.* 67, 672-676 (1981).

6. Smith, M. A., Jonsson, L., Stymne, S., & Stobart, K. Evidence for cytochrome $b_5$ as an electron donor in ricinoleic biosynthesis in microsomal preparations from developing castor bean (*Ricinus communis* L). *Biochem. J.* 287:141-144 (1992).

7. van de Loo, F. J., Broun, P., Turner, S., & Somerville, C. An Oleate 12-hydroxylase from *Ricinus communis* L. is a fatty acyl desaturase homolog. *Proc. Natl. Acad. Sci. USA* 92, 6743-6745 (1995).

8. Broun, P. & Somerville, C. Accumulation of ricinoleic, lesquerolic, and densipolic acids in seeds of transgenic *Arabidopsis* plants that express a fatty acyl hydroxylase cDNA from castor bean. *Plant Physiol.* 113, 933-942 (1997).

9. Smith, M. A., Moon, H., Chowrira, G., & Kunst, L. Heterologous expression of a fatty acid hydroxylase gene in developing seeds of *Arabidopsis thaliana*. *Planta* 217, 506-517 (2003).

10. Kennedy, E. P. Biosynthesis of complex lipids. *Fed. Proc.* 20, 934-940 (1961).

11. Zheng Z. et al. AtGPAT1, a member of the membrane-bound glycerol-3-phosphate acyltransferase gene family, is essential for tapetum differentiation and male fertility. *Plant Cell* 15, 1872-1887 (2003).

12. Kim, H. U., Li, Y., & Huang, A. H. Ubiquitous and endoplasmic reticulum-located lysophosphatidyl acyltransferase, LPAT2, is essential for female but not male gametophyte development in *Arabidopsis*. *Plant Cell*, 17, 1073-1089 (2005).

13. Brown, A. P., Slabas, A. R., & Denton, H. Substrate selectivity of plant and microbial lysophosphatidic acid acyltransferases. *Phytochem.* 61, 493-501 (2002).

14. Lin J. T. et al. Biosynthesis of triacylglycerols containing ricinoleate in castor microsomes using 1-acyl-2-oleoyl-sn-glycero-3-phosphocholine as the substrate of oleoyl-12-hydroxylase. *Lipids* 33, 59-69 (1998).

15. Dahlqvist, A. et al. "Phospholipid:diacylglycerol acyltransferase: an enzyme that catalyzes the acyl-CoA-independent formation of triacylglycerol in yeast and plants" *Proc. Natl. Acad. Sci. USA* 97, 6487-6492 (2000).

16. Hobbs, D. H., Lu, C., & Hills, M. J. Cloning of a cDNA encoding diacylglycerol acyltransferase from *Arabidopsis thaliana* and its functional expression. *FEBS Lett.* 452, 145-149 (1999).

17. Zou, J. et al. The *Arabidopsis thaliana* TAG1 mutant has a mutation in a diacylglycerol acyltransferase gene. *Plant J* 19, 645-653 (1999).

18. Lardizabal, K. D. et al. DGAT2 is a new diacylglycerol acyltransferase gene family. *J. Biol. Chem.* 276, 38862-38869 (2001).

19. Shockey, J. M., Fulda, M. S., & Browse, J. A. *Arabidopsis* contains nine long-chain acyl coenzyme A synthetase genes that participate in fatty acid and glycerolipid metabolism. *Plant Physiol* 129, 1710-1722 (2002).
20. Kunst L., Taylor D. C., & Underhill E. W. Fatty acid elongation in developing seed of *Arabidopsis thaliana. Plant Physiol. Biochem.* 30, 425-434 (1992).
21. Slightom, J. L., Sun, S. M., & Hall, T. C. Complete nucleotide sequence of a french bean storage protein gene: phaseolin. *Proc. Natl. Acad. Sci. USA* 80, 1897-1901 (1983).
22. Sandager L. et al. Storage lipid synthesis is non-essential in yeast. *J. Biol. Chem.* 277, 6478-6482 (2002).
23. Beisson, F. et al. *Arabidopsis* genes involved in acyl lipid metabolism. A 2003 census of the candidates, a study of the distribution of expressed sequence tags in organs, and a web-based database. *Plant Physiol.* 132, 681-697 (2003).
24. Ichihara, K., Takahashi, T., & Fujii, S. Diacylglycerol acyltransferase in maturing safflower seeds: its influences on the fatty acid composition of triacylglycerol and on the rate of triacylglycerol synthesis. *Biochem. Biophys. Acta* 958, 125-129 (1988).
25. Vogel, G. & Browse, J. Cholinephosphotransferase and diacylglycerol acyltransferase (substrate specificities at a key branch point in seed lipid metabolism). *Plant Physiol.* 110, 923-931 (1996).
26. Wiberg, E., Tillberg, E., & Stymne, S. Substrates of diacylglycerol acyltransferase in microsomes from developing oil seeds. *Phytochem.* 36, 573-577 (1994).
27. He, X., Turner, C., Chen, G. Q., Lin, J. T., & McKeon, T. A. Cloning and characterization of a cDNA encoding diacylglycerol acyltransferase from castor bean. *Lipids* 39, 311-318 (2004).
28. Brown, A. P., Brough, C. L., Kroon, J. T., & Slabas, A. R. Identification of a cDNA that encodes a 1-acyl-sn-glycerol-3-phosphate acyltransferase from *Limnanthes douglasii. Plant Mol. Biol.* 29, 267-278 (1995).
29. Hanke, C., Wolter, F. P., Coleman, J., Peterek, G., & Frentzen, M. A plant acyltransferase involved in triacylglycerol biosynthesis complements an *Escherichia coli* sn-1-acylglycerol-3-phosphate acyltransferase mutant. *Eur. J. Biochem.* 232, 806-810 (1995).
30. Knutzon, D. S. et al. Cloning of a coconut endosperm cDNA encoding a 1-acyl-sn-glycerol-3-phosphate acyltransferase that accepts medium-chain-length substrates. *Plant Physiol.* 109, 999-1006 (1995).
31. Knutzon, D. S. et al. Lysophosphatidic acid acyltransferase from coconut endosperm mediates the insertion of laurate at the sn-2 position of triacylglycerols in lauric rapeseed oil and can increase total laurate levels. *Plant Physiol.* 120, 739-746 (1999).
32. Lassner, M. W., Levering, C. K., Davies, H. M., & Knutzon, D. S. Lysophosphatidic acid acyltransferase from meadowfoam mediates insertion of erucic acid at the sn-2 position of triacylglycerol in transgenic rapeseed oil. *Plant Physiol.* 109, 1389-1394 (1995).
33. Clough, S. J. & Bent, A. F. Floral dip: a simplified method for *Agrobacterium*-mediated transformation of *Arabidopsis thaliana. Plant J* 16, 735-743 (1998).
34. Lukowitz, W., Gillmor, C. S., & Scheible, W. R. Positional cloning in *Arabidopsis*. Why it feels good to have a genome initiative working for you. *Plant Physiol.* 123, 795-806 (2000).
35. Miquel, M. & Browse, J. *Arabidopsis* mutants deficient in polyunsaturated fatty acid synthesis. *J. Biol. Chem.* 267, 1502-1509 (1992).
36. Turner, C. et al. Lipase-catalyzed methanolysis of triricinolein in organic solvent to produce 1,2(2,3)-diricinolein. *Lipids* 38, 1197-1206 (2003).
37. Hajra, A. K. On the extraction of acyl and alkyl dihydroxyacetone phosphate from incubation mixtures. *Lipids* 9, 502-505 (1974).

Table of Exemplary Coding Sequences

| SEQ ID NO | Clone Name | Length | Type |
|---|---|---|---|
| 47 | RcDGAT2 orf | 1023 | DNA |
| 48 | RcDGAT1 orf | 1566 | DNA |
| 49 | RcPDAT1A orf | 1992 | DNA |
| 50 | RcPDAT1B orf | 2058 | DNA |
| 51 | RcLPAAT1 orf | 1128 | DNA |
| 52 | RcLACS4 orf | 2001 | DNA |
| 53 | AtDGAT2 orf | 945 | DNA |
| 54 | RcDGAT2 prt | 340 | Protein |
| 55 | RcDGAT1 prt | 521 | Protein |
| 56 | RcPDAT1A prt | 663 | Protein |
| 57 | RcPDAT1B prt | 685 | Protein |
| 58 | RcLPAAT1 prt | 375 | Protein |
| 59 | RcLACS4 prt | 666 | Protein |
| 60 | AtDGAT2 prt | 314 | Protein |
| 61 | FAH12 cDNA | 1440 | DNA |
| 62 | FAH12 prt | 387 | Protein |
| 63 | BarleyDGAT2 prt | 333 | Protein |
| 64 | WheatDGAT2 prt | 336 | Protein |
| 65 | BnDGAT2 prt | 317 | Protein |
| 66. | Maize DGAT2 prt | 333 | Protein |
| 67. | Rice DGAT2 prt | 340 | Protein |

The invention claimed is:

1. An isolated DNA sequence encoding a protein or polypeptide comprising or consisting of an amino acid sequence selected from the group consisting of SEQ ID NO:54 and SEQ ID NO:56, respective biologically active variants and biologically active portions thereof, with respective sequences having at least 85% identity thereto, and wherein the variants have diacylglycerol acyltransferase (DGAT) and phospholipid diacylglycerol acyltransferase (PDAT) activity, respectively.

2. The isolated DNA sequence of claim 1, encoding a protein or polypeptide comprising or consisting of an amino acid sequence selected from the group consisting of SEQ ID NO:54 and SEQ ID NO:56, and biologically active portions thereof.

3. The isolated DNA sequence of claim 1, wherein the isolated DNA comprises or consists of a sequence selected from the group consisting of SEQ ID NO:47 and SEQ ID NO:49, and sequences having at least 85% identity thereto.

4. The isolated DNA sequence of claim 3, wherein the isolated DNA comprises or consists of a sequence selected from the group consisting of SEQ ID NO:47 and SEQ ID NO:49.

5. A recombinant expression vector, comprising at least one DNA sequence encoding a protein or polypeptide comprising or consisting of an amino acid sequence selected from the group consisting of SEQ ID NO:54 and SEQ ID NO:56, respective biologically active variants, and biologically active portions thereof, with respective sequences having at least 85% identity thereto, and fusions thereof, the at least one DNA sequence in operative association with transcriptional and translational regulatory regions or sequences suitable to provide for expression of the at least one DNA sequence and the respective encoded protein or polypeptide in a host cell, and wherein the variants have diacylglycerol acyltransferase (DGAT) and phospholipid diacylglycerol acyltransferase (PDAT) activity, respectively.

6. The recombinant expression vector of claim 5, wherein at least one DNA sequence encoding a protein or polypeptide comprises or consists of an amino acid sequence selected from the group consisting of SEQ ID NO:54 and SEQ ID NO:56, and biologically active portions thereof.

7. The recombinant expression vector of claim 5, wherein the host cell is a plant cell.

8. The recombinant expression vector of claim 5, wherein the host cell is a yeast cell.

9. The recombinant expression vector of claim 5, wherein the transcriptional initiation region or sequence provides for preferential expression in plant seed tissue.

10. The recombinant expression vector of claim 9, wherein the transcriptional initiation region or sequence comprises the phaseolin promoter.

11. The recombinant expression vector of claim 5, further comprising a T-DNA border element.

12. A host cell, transformed with the recombinant expression vector of any one of claims 5-6.

13. The host cell of claim 12, wherein the host cell is a plant cell.

14. The host cell of 12, wherein the host cell is a yeast cell.

15. The host cell of 12, comprising at least one expression vector having a DNA sequence that encodes upon expression a protein or polypeptide comprising or consisting of an amino acid sequence selected from the group consisting of SEQ ID NO:54 and SEQ ID NO:56, respective biologically active variants, biologically active portions thereof, with respective sequences having at least 85% identity thereto, and respective fusion proteins thereof operatively associated with a heterologous polypeptide.

16. The host cell of claim 12, wherein the DNA sequence comprises a sequence selected from the group consisting of SEQ ID NO:47 and SEQ ID NO:49, and sequences having at least 85% identity thereto.

17. The host cell of claim 16, wherein the DNA sequence comprises a DNA sequence selected from the group consisting of SEQ ID NO:47 and SEQ ID NO:49.

18. A host cell, comprising a first DNA construct and a second DNA construct, wherein
the first DNA construct comprises a first DNA sequence encoding a protein or polypeptide comprising or consisting of an amino acid sequence selected from the group consisting of SEQ ID NO:54 and SEQ ID NO:56, respective biologically active variants, and biologically active portions thereof, with respective sequences having at least 85% identity thereto, and fusions thereof, the DNA sequence in operative association with transcriptional and translational regulatory regions or sequences suitable to provide for expression of the first DNA sequence and the respective encoded protein or polypeptide in a host cell, wherein the variants have diacylglycerol acyltransferase (DGAT) and phospholipid diacylglycerol acyltransferase (PDAT) activity, respectively, wherein
the second DNA construct comprises a second DNA sequence encoding a protein or polypeptide comprising or consisting of an amino acid sequence selected from the group consisting of SEQ ID NOS:55 and SEQ ID NOS:57-59, respective biologically active variants, and biologically active portions thereof, with respective sequences having at least 85% identity thereto, and fusions thereof, the DNA sequence in operative association with transcriptional and translational regulatory regions or sequences suitable to provide for expression of the second DNA sequence and the respective encoded protein or polypeptide in the host cell, and wherein the variants have diacylglycerol acyltransferase (DGAT), phospholipid diacylglycerol acyltransferase (PDAT), lysophosphatidic acid acyltransferase (LPAAT), and long chain acyl-CoA synthetase (LACS) activity, respectively.

19. The host cell of claim 18, wherein the first DNA construct comprises a DNA sequence encoding a protein or polypeptide comprising or consisting of an amino acid sequence selected from the group consisting of SEQ ID NO:54, respective biologically active variants, and biologically active portions thereof, the DNA sequence in operative association with transcriptional and translational regulatory regions or sequences suitable to provide for expression of the second DNA sequence and the respective encoded protein or polypeptide in the host cell.

20. The host cell of any one of claims 18 and 19, wherein the host cell is a plant cell.

21. The host cell of any one of claims 18 and 19, wherein the host cell is a yeast cell.

22. A method to enhance hydroxy fatty acid accumulation in plants, comprising introducing, into at least one plant cell or tissue, the recombinant expression vector of any one of claims 5-6, provided that at least one of SEQ ID NO:54 and SEQ ID NO:56, respective biologically active variants, and biologically active portions thereof, with respective sequences having at least 85% identity thereto, and fusions thereof, is expressed, wherein enhanced hydroxy fatty acid accumulation in the plant cell or tissue is afforded, and wherein the variants have diacylglycerol acyltransferase (DGAT) and phospholipid diacylglycerol acyltransferase (PDAT) activity, respectively.

23. The method of claim 22, wherein at least one of SEQ ID NO:54, respective biologically active variants, and biologically active portions thereof, is expressed, and wherein at least one of SEQ ID NO:56, respective biologically active variants, and biologically active portions thereof, is also expressed.

24. The method of claim 22, further comprising recombinant expression of an oleoyl-12-hydroxylase.

25. The method of claim 24, wherein the oleoyl-12-hydroxylase is a *Ricinus communis* oleoyl-12-hydroxylase.

26. The method of claim 22, wherein the host cell is deficient for at least one of a fatty acyl elongase and a fatty acyl desaturase.

27. The method of claim 22, wherein the at least one DNA sequence comprises or consists of a sequence selected from the group consisting of SEQ ID NO:47 and SEQ ID NO:49, and sequences having at least 85% identity thereto.

28. The method of claim 27, wherein the at least one DNA sequence comprises or consists of SEQ ID NO:47.

29. The method of claim 22, wherein the enhanced hydroxy fatty acid accumulation is in at least one form selected from the group consisting of fatty acids (FA), fatty acid esters, diacylglycerol (DAG), triaclyglcerol (TAG), and combinations thereof.

30. The method of claim 22, wherein enhanced hydroxy fatty acid accumulation is that of ricinoleic acid.

31. The method of claim 30, wherein the enhanced ricinoleic acid accumulation is in at least one form selected from the group consisting of fatty acids (FA), fatty acid esters, diacylglycerol (DAG), triaclyglcerol (TAG), and combinations thereof.

32. The method of claim 22, wherein the plant cell is that of a oilseed plant.

33. The method of claim 32, wherein the plant cell is selected from the group consisting of canola, rapeseed (Canola and High Erucic Acid varieties), sunflower, safflower, cotton, Cuphea, soybean, peanut and corn.

34. A method to increase at least one of total lipid content, percent seed germination, and seed weight in transgenic plants, comprising introducing, into at least one plant cell or tissue, the recombinant expression vector of any one of claims 5-6, provided that at least one of SEQ ID NO:54 and SEQ ID NO:56, respective biologically active variants, and biologically active portions thereof, with respective sequences having at least 85% identity thereto, and fusions thereof, is expressed, wherein an increase in at least one of total lipid content, percent seed germination, and seed weight is afforded, and wherein the variants have diacylglycerol acyltransferase (DGAT) and phospholipid diacylglycerol acyltransferase (PDAT) activity, respectively.

35. The method of claim 34, wherein at least one of SEQ ID NO:54, respective biologically active variants, and biologically active portions thereof is expressed, and wherein at least one of SEQ ID NO:56, respective biologically active variants, and biologically active portions thereof, is also expressed.

36. The method of claim 34, wherein the host cell is deficient for at least one of a fatty acyl elongase and a fatty acyl desaturase.

37. The method of claim 34, further comprising recombinant expression of a oleoyl-12-hydroxylase.

38. The method of claim 37, wherein the oleoyl-12-hydroxylase is a *Ricinus communis* oleoyl-12-hydroxylase.

39. The method of claim 34, wherein the plant cell is selected from the group consisting of canola, rapeseed (Canola and High Erucic Acid varieties), sunflower, safflower, cotton, Cuphea, soybean, peanut and corn.

40. A plant seed from a plant having at least one cell transformed with the recombinant expression vector of any one of claims 5-6.

* * * * *

SEQUENCE LISTING

```
<160> NUMBER OF SEQ ID NOS: 68

<210> SEQ ID NO 1
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 3, 6, 9, 12, 18
<220> FEATURE:
<223> OTHER INFORMATION: N is inosine

<400> SEQUENCE: 1
```
cgnasnasng gnvhwcynaa rgg                                    23

<210> SEQ ID NO 2
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: 4, 7, 13, 19
<220> FEATURE:
<223> OTHER INFORMATION: N is A, C, G, or T

<400> SEQUENCE: 2
rtcnccngtr trnarccanc                                        20

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gtggatgtat gcctagaatc tgttc                                  25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
caccaatatc acctgtgtgg aacca                                  25

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
actacactgc agaaatggca caacagaggc agag                        34

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
gatcaactcg agtcaagcac tgggtttgct tgc                         33

<210> SEQ ID NO 7
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 3, 6, 9, 12, 15, 21
<220> FEATURE:
<223> OTHER INFORMATION: N  is Inosine
<220> FEATURE:

```
<221> NAME/KEY: variation
<222> LOCATION: 24
<220> FEATURE:
<223> OTHER INFORMATION: N is A, C, G, or T

<400> SEQUENCE: 7
ggnyknccna cnaynacrtk natngg                                        26

<210> SEQ ID NO 8
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 6, 9, 12, 15
<220> FEATURE:
<223> OTHER INFORMATION: N is Inosine

<400> SEQUENCE: 8
carwsngcng gnctnttyaa yct                                           23

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
gtaacgctgt gtttcgcaca ccagt                                         25

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
accgagaact ccccaaaaga caattg                                        26

<210> SEQ ID NO 11
<211> LENGTH: 37
<212> TYPE: DNA
<213> ORGANISM: Artificial Sequence
<220> FEATURE:
<223> OTHER INFORMATION: Primer

<400> SEQUENCE: 11
actacactgc agaaatgggg gaagaagcga atcataa                            37

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
gatcaactcg agtcaaagaa tttcaag                                       27

<210> SEQ ID NO 13
<211> LENGTH: 37
<212> TYPE: DNA
<213> ORGANISM: Artificial Sequence
<220> FEATURE:
```

<223> OTHER INFORMATION: Primer

<400> SEQUENCE: 13
tcagatggta ccaaatgggg gaagaagcga atcataa      37

<210> SEQ ID NO 14
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 6, 9, 12, 15
<220> FEATURE:
<223> OTHER INFORMATION: N is Inosine

<400> SEQUENCE: 14
carwsngcng gnctnttyaa yct      23

<210> SEQ ID NO 15
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 9, 12, 15, 24
<220> FEATURE:
<223> OTHER INFORMATION: N is Inosine

<400> SEQUENCE: 15
tgrtartana gnagnacrca catngg      26

<210> SEQ ID NO 16
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 3, 6, 9, 21
<220> FEATURE:
<223> OTHER INFORMATION: N is Inosine
<220> FEATURE:
<221> NAME/KEY: variation
<222> LOCATION: 24
<220> FEATURE:
<223> OTHER INFORMATION: N is A, C, G, or T

<400> SEQUENCE: 16
tcnctngynt ayttyatgvt ngcn      24

<210> SEQ ID NO 17
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: 3
<220> FEATURE:
<223> OTHER INFORMATION: N is A, C, G, or T
<220> FEATURE:
<221> NAME/KEY: modified_base
<222> LOCATION: 15, 18
<220> FEATURE:
<223> OTHER INFORMATION: N is Inosine

<400> SEQUENCE: 17
acnggcatrt tccanaknck ccar                                          24

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
tgtgctgtct ttctctccca gta                                           23

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
taaattcgga actgagagct tcaga                                         25

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
cttttaaagg gtgttgagaa ttc                                           23

<210> SEQ ID NO 21
<211> LENGTH: 38
<212> TYPE: DNA
<213> ORGANISM: Artificial Sequence
<220> FEATURE:
<223> OTHER INFORMATION: Primer

<400> SEQUENCE: 21
cgttgactgc agaaatgacg attctcgaaa cgccagaa                           38

<210> SEQ ID NO 22
<211> LENGTH: 38
<212> TYPE: DNA
<213> ORGANISM: Artificial Sequence
<220> FEATURE:
<223> OTHER INFORMATION: Primer

<400> SEQUENCE: 22
tcatcactcg agtcagttcc catcgcgatt cattaggt                           38

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
agcactgcgg gtaaactaaa ctc                                           23

<210> SEQ ID NO 24
<211> LENGTH: 38
<212> TYPE: DNA

<213> ORGANISM: Artificial Sequence
<220> FEATURE:
<223> OTHER INFORMATION: Primer

<400> SEQUENCE: 24
cgttgactgc agaaatgagc actgcgggta aactaaac                38

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
ctacgactcg agttacttct cctccaggcg ccgta                   35

<210> SEQ ID NO 26
<211> LENGTH: 35
<212> TYPE: DNA
<213> ORGANISM: Artificial Sequence
<220> FEATURE:
<223> OTHER INFORMATION: Primer

<400> SEQUENCE: 26
actacactgc agaaatgggt ggttccagag agttc                   35

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
tacgatctcg agtcaaagaa ttttcagctc aagatc                  36

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
ttcatatgca acatgatgct gag                                23

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
actacactgc agaaatgggt ggttccagag agttc                   35

<210> SEQ ID NO 30
<211> LENGTH: 35
<212> TYPE: DNA
<213> ORGANISM: Artificial Sequence
<220> FEATURE:
<223> OTHER INFORMATION: Primer

<400> SEQUENCE: 30
tcagatggta ccaaatgggt ggttccagag agttc                   35

```
<210> SEQ ID NO 31
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 9, 18
<220> FEATURE:
<223> OTHER INFORMATION: N is Inosine

<400> SEQUENCE: 31
tayttyytnc ayttymtnaa rtgggt                                        26

<210> SEQ ID NO 32
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: 3, 12, 18
<220> FEATURE:
<223> OTHER INFORMATION: N is A, C, G, or T

<400> SEQUENCE: 32
gcncayttyt cnyayggnat hgchga                                        26

<210> SEQ ID NO 33
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 12
<220> FEATURE:
<223> OTHER INFORMATION: N is Inosine
<220> FEATURE:
<221> NAME/KEY: variation
<222> LOCATION: 21
<220> FEATURE:
<223> OTHER INFORMATION: N is A, C, G, or T

<400> SEQUENCE: 33
aartaytggt cnaaycchyt ngarachaa                                     29

<210> SEQ ID NO 34
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 6, 9, 12
<220> FEATURE:
<223> OTHER INFORMATION: N is Inosine
<220> FEATURE:
<221> NAME/KEY: variation
<222> LOCATION: 21
<220> FEATURE:
<223> OTHER INFORMATION: N is A, C, G, or T

<400> SEQUENCE: 34
tayggngtng gnathcchac nga                                           23

<210> SEQ ID NO 35
```

```
<211> LENGTH: 26
<212> TYPE: DNA
<213> ORGANISM: Artificial Sequence
<220> FEATURE:
<223> OTHER INFORMATION: Primer

<400> SEQUENCE: 35
atgtcgattt tgagacggag attaag                                          26

<210> SEQ ID NO 36
<211> LENGTH: 40
<212> TYPE: DNA
<213> ORGANISM: Artificial Sequence
<220> FEATURE:
<223> OTHER INFORMATION: Primer

<400> SEQUENCE: 36
tacacaggcg cgccaaatgt cgattttgag acggagatta                           40

<210> SEQ ID NO 37
<211> LENGTH: 35
<212> TYPE: DNA
<213> ORGANISM: Artificial Sequence
<220> FEATURE:
<223> OTHER INFORMATION: Primer

<400> SEQUENCE: 37
gatcaactcg agctatgaat ctatagcggc caagt                                35

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
atgcctgtaa ttcggaggaa aaaac                                           25

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
aatgatcgta ctctctaatg tatgttc                                         27

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
cagccatctt catcgccatc attag                                           25

<210> SEQ ID NO 41
<211> LENGTH: 39
<212> TYPE: DNA
<213> ORGANISM: Artificial Sequence
<220> FEATURE:
<223> OTHER INFORMATION: Primer

<400> SEQUENCE: 41
```

```
actagactgc agaaatgcct gtaattcgga ggaaaaaac                               39
```

<210> SEQ ID NO 42
<211> LENGTH: 37
<212> TYPE: DNA
<213> ORGANISM: Artificial Sequence
<220> FEATURE:
<223> OTHER INFORMATION: Primer

<400> SEQUENCE: 42

```
gtcgatctcg agttacagtg gtaatttgat cttctga                                37
```

<210> SEQ ID NO 43
<211> LENGTH: 17
<212> TYPE: DNA
<213> ORGANISM: Artificial Sequence
<220> FEATURE:
<223> OTHER INFORMATION: Primer

<400> SEQUENCE: 43

```
gtaaaacgac ggccagt                                                      17
```

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44

```
ggaaacagct atgaccatg                                                    19
```

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45

```
gtaatacgac tcactatagg gc                                                22
```

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46

```
aattaaccct cactaaaggg                                                   20
```

<210> SEQ ID NO 47
<211> LENGTH: 1023
<212> TYPE: DNA
<213> ORGANISM: Ricinus commuinis

<400> SEQUENCE: 47

```
atgggggaag aagcgaatca taataataat aataataata tcaatagtaa tgatgagaag        60
aatgaagaga atcaaattta cagttgta aattcgagag aactataccc aacgaacata        120
tttcacgcac tgttagcgtt gagcatatgg attggttcaa tccatttcaa tctcttctta       180
ctcttcatct ttatctcttt cctttctttt cccacattcc tcctgattgt tggattttt        240
gtggtgttaa tgttcattcc gatcgacgaa cacagtaagt tgggccgtcg tttgtgcagg       300
```

-continued

```
tatgtatgca gacatgcgtg cagtcatttt ccggtaactc tccatgttga agacatgaat    360
gcttttcatt ctgatcgtgc ttacgttttt ggttatgagc acattcagt  atttcccctt    420
ggtgtttctg tactatcaga tcactttgct gtcctgcccc ttcctaaaat gaaggtcctt    480
gcaagtaacg ctgtgtttcg cacaccagtt ttaaggcata tatggacatg gtgtggtctt    540
acatcagcaa caagaaaaa  tttcactgcc ctcctagcat ctggttatag ttgcattgtg    600
attcccggtg gagttcaaga gacattttat atgaagcatg gctctgagat tgctttcctt    660
aaggcgagaa gagggtttgt ccgagtagct atggagatgg gtaaaccctt ggttccagtt    720
ttctgctttg gtcaatcgaa cgtgtacaag tggtggaaac ctgatggcga gttatttatg    780
aaaattgcta gagctattaa gttcagccca attgtctttt ggggagttct cggttctcat    840
ttaccgctac aacgtccaat gcatgttgtc gtcggtaaac cgattgaggt gaagcaaaat    900
ccacagccta cagtggaaga ggtctcagaa gtacagggtc agtttgttgc ggcacttaaa    960
gatcttttg  aaaggcataa agcacgggtt ggctatgcag accttacact tgaaattctt   1020
tga                                                                 1023

<210> SEQ ID NO 48
<211> LENGTH: 1566
<212> TYPE: DNA
<213> ORGANISM: Ricinus commuinis

<400> SEQUENCE: 48
atgacgattc tcgaaacgcc agaaactctt ggcgtcatct cctcctccgc cacttccgat     60
ctcaacctct ctctccgacg tagacggacc tcaaatgact ccgatggtgc acttgctgat    120
ttggcttcga agtttgatga tgatgacgac gtaagatcgg aagattctgc tgaaaatatt    180
atcgaagatc ctgtagcagc ggttactgaa ttggcgacag caaagagtaa cggaaaagac    240
tgtgttgcca atagtaataa ggataaaatt gatagccatg gaggatcatc ggattttaaa    300
cttgcatata ggccttcggt tccagctcac cggtcactta aggagagtcc gcttagctct    360
gatttaatat ttaaacaaag tcatgcaggt ctgtttaacc tttgtatagt agtgctcgta    420
gctgttaaca gcaggctcat cattgagaat ttaatgaagt atggctggtt aattaagacg    480
ggcttttggt ttagttcaag atcattgaga gattggccgc ttttatgtg  ctgtcttct    540
ctcccagtat tcccccttgc tgcctatcta gttgagaagg ccgcatatcg aaatatata     600
tctccgccta tgttattttt ccttcatgtg atcatcacct cagcagctgt tttgtaccca    660
gcttctgtaa ttctcagttg tgaatctgct tttttatctg gtgtcacatt gatggaactt    720
gcttgtatgg tatggttgaa attggtatcc tatgcacata caaactatga tatgagagcg    780
atcgctgaca ccattcataa ggaagatgca tccaattctt ctagtacaga gtattgtcat    840
gatgtgagct ttaagacttt ggcgtacttc atggtcgcac ccacattatg ttaccagcca    900
agttatcctc gcacagcatt tattagaaag ggctgggtgt tccgtcaatt tgtcaaacta    960
ataattttta caggattcat gggatttatc atagaacaat acatcaatcc tatcgtccag   1020
aattctcaac accctttaaa agggqatctc ttatatgcca ttgagagggt tctgaagctc   1080
tcagttccga atttatatgt gtggctctgc ttgttctact gcttttttca cctgtggttg   1140
aatatagttg ctgagctcct tcgcttcggt gaccgggagt tctacaaaga ttggtggaat   1200
gcaaaaactg ttgaggagta ctggaggatg tggaatatgc ctgttcacaa gtggatggtt   1260
cgccatatct acttcccatg cctacgtcgt aaaataccaa ggggggtagc aatagttatt   1320
gctttcttcg tttcagctgt atttcatgag ttgtgcattg ctgttccttg ccacatgttc   1380
```

-continued

```
aaactttggg ctttttttgg aataatgttt cagattcctt tagttgtgat cactaattat   1440
tttcaaagga agttcagaag ctcaatggtg ggaaatatga tcttctggtt ctttttctgc   1500
attctcggcc aacctatgtg tgtactgttg tattaccatg acctaatgaa tcgcgatggg   1560
aactga                                                              1566
```

<210> SEQ ID NO 49
<211> LENGTH: 1992
<212> TYPE: DNA
<213> ORGANISM: Ricinus commuinis

<400> SEQUENCE: 49

```
atgtcgattt tgagacggag attaagagtg caaaattctt cccaaattga ggccgacaac     60
gatgagaaag agaaggagaa gcgaaagaga aagaaagaga tcaagaaatg gaggtgcgtg    120
gacaattgct gttggtttat aggttttata tgttcgatgt ggtggttttt actattttta    180
tacaatgcaa tgcctgcttc ttttcctcaa tatgtgacgg aggcgataac gggaccgatg    240
ccggacccac ctggcgttaa attaaggaag gaagggttga ctgtcaaaca tccggtggtt    300
tttgtgcctg gcattgttac aggtggactt gagttatggg aaggacatca gtgtgctgat    360
ggtttgttta gaaaacgact ttggggtggt acatttggtg atctctacaa aagaccacta    420
tgctgggttg agcatatgtc tctggacaat gaaacaggac tagaccctcc tggcattagg    480
gtcagggctg tatctggact tgtggcagct gattattttg cagcaggtta ttttgtctgg    540
gcagttttaa ttgctaattt ggctcgcctt gggtatgagg agaaaaacat gtatatggct    600
gcatatgact ggagactatc atttcagaac actgagatta gggaccaaag tttgagcagg    660
ataaaaagta atatagaact catggtggct accaatggcg ggaataaggt ggttgttctt    720
ccacattcaa tgggtgttcc atactttctg catttcatga aatgggtaga ggcaccagct    780
ccaatgggtg gtgggggtgg acctgattgg tgtgccaagc acataaaagc ggtgatcaat    840
attggtggac catttctggg tgtgccaaaa gcaatctcat cacttttctc aaatgaagga    900
agggatattg ctgcagccag ggctttcgcg ccaggatttt tggataagga tgtttttggt    960
cttcaaactt ttcagcatgc aatgcgattg actcggacat gggattcaac catgtccatg   1020
ataccaaaag gtggggaaac tatctggggt ggccttgatt ggtcgcctga aggagtctac   1080
aactgtggtt caaacacacc aaagaacaat aatacccaga ctgcaggtca aactgggaaa   1140
ggaacttcaa gtttcacaga aggtgtgaac tatgggagaa ttatatcgtt tgggaaagat   1200
gtggctgagc ttcattcttc caaaattgat aggatagatt tcagggatgc tgttaagggt   1260
aatagagttg caaacaattg tgacatctgg acggagtacc aagaaatggg tattggaggt   1320
atcaaagctg ttgctgatta taaagtatac acagctggat cagttataga tctgctgcat   1380
tttgtagctc ctaagcttat ggcacgtgga gatgctcatt tttcacatgg gattgcggac   1440
aatttggacg atccaaaata tgagcactac aaatattggt caaacccttt ggaaacaaga   1500
ttaccagatg ctcctgagat ggagttatat tctatgtatg gaattggaat accgactgaa   1560
agagcatata tttacaagct aactctaacc agtgaatgcg ctattccctt tcagatagat   1620
acctcagtga caggtggaag cgagaactct tgtctaaaag atggaactct taatgttaat   1680
ggagacgaga cagttcctgt attaagtgct ggttttatgt ttgcaaaggg ttggcgaggg   1740
aaaactagat tcaacccttc aggcattcat acttatataa gggaatataa tcacgctcca   1800
cctgctaatc ttctggaggg tcgaggcacc cagagtggtg ctcatgttga tatcttgggg   1860
aattttgcat taatagagga cgttttaagg atagcagctg gagctagagg agaggatttg   1920
```

| | |
|---|---|
| ggaggagacc gagtttattc tgatatttc aaatggtctg agaagatcaa cttggccgct | 1980 |
| atagattcat ag | 1992 |

<210> SEQ ID NO 50
<211> LENGTH: 2058
<212> TYPE: DNA
<213> ORGANISM: Ricinus commuinis

<400> SEQUENCE: 50

| | |
|---|---|
| atgcctgtaa ttcggaggaa aaacccact tctgaaccca acaaaaattc agcatcagac | 60 |
| tcaaaaacgc caagcgagga agaggaacat gaacaagaac aggaacaaga agaagataaa | 120 |
| aataacaaaa agaaatacc aagaagaag agcagtgaaa tcaatgcaaa aaatggtca | 180 |
| tgcatagaca gctgttgttg gtttgttggt tgcatctgcg tgacgtggtg ggttttacta | 240 |
| tttctttaca atgcagtgcc tgcgtctttg cctcaatacg taactgaggc aatcacgggt | 300 |
| cctttacccg atccacctgg tgttaagctg aaaaagagg gattaacagc aaagcatcca | 360 |
| gtggttttg tacctgggat tgttaccgcg gggcttgaat tgtgggaagg ccatcagtgt | 420 |
| gctgatgggc tgtttaggaa acggctctgg ggtggaactt ttggagaagt ttataagagg | 480 |
| cctctctgct gggtagagca tatgtctcta gacaatgaaa ctggattgga tcctcctggt | 540 |
| ataagggtca ggccagtctc tggacttgtg gctgctgatt actttgctcc aggctatttt | 600 |
| gtgtgggctg ttctgattgc taatttggca cgcattggat atgaggagaa acaatgttc | 660 |
| atggcctcat acgattggag actttcattt cagaacactg aggtccgtga ccaaacatta | 720 |
| agccggatga agagtaatat agaacttatg gtttctatca atggtggaaa taaggcagtt | 780 |
| attgttccac attccatggg tgttttgtac tttctgcatt ttatgaagtg ggttgaggca | 840 |
| ccagctccaa tgggaggagg tggtggacca gattggtgtg ctaagcatat caaggcagtc | 900 |
| atgaacattg tggtccatt tttaggtgtt cccaaagctg ttgctgggct tttctcggct | 960 |
| gaagcaagag atattgcagt tgccagggcc atagcaccag gtttcttaga taatgatatg | 1020 |
| ttccgcctac aaacattgca acacatgatg aggatgtctc gcacatggga ttcgaccatg | 1080 |
| tcaatgatac caagaggtgg ggacactatc tggggcgatc ttgattggtc acctgaagaa | 1140 |
| ggttacattc ctagaaagaa aaggcagaga ataatgcaa ctgataatgt aaacgaaggt | 1200 |
| ggggccgaaa gtgagatttc tcaaagaaag attgttagat atggaagaat gatatcattt | 1260 |
| gggaaaaata tagcagaggc accttcatat gatattgaaa ggattgactt tagggatgct | 1320 |
| gttaaaggtc gtagtgtggc aaataatacc tgccttgatg tgtggactga ataccatgaa | 1380 |
| atgggattcg gaggtattaa agccgttgca gagtataagg tctacactgc tggatctact | 1440 |
| atagagctgc ttcagtttgt cgccccaaaa atgatggagc gtggtagtgc tcatttttct | 1500 |
| tatggaattg ctgacaattt ggaggaccca aaatatgagc actacaaata ctggtcaaat | 1560 |
| cccctggaga caaagttacc taatgctcca gaaatggaaa tattttccat gtatggagtt | 1620 |
| ggcataccaa cagaaagagc ttatgtttat gagttttctc ctgctgctga gtgctacatt | 1680 |
| ccatttcaga ttgatacatc agctaatgat ggcgatgaag atggctgtct gaaagatgga | 1740 |
| gtctatactg ttgatgggga tgagactgtt cctgttttaa gtgcaggctt catgtgtgct | 1800 |
| aaagcttggc gtgggaaaac cagatttaat ccttcaggaa gtcgaacata cattagagag | 1860 |
| tacgatcatt ctcctccagc taatttgcta gagggccgag gcacccaaag tggtgcccat | 1920 |
| gttgatataa tgggtaattt tgcttttaatc gaggatatta tgagggtggc agccggggct | 1980 |
| acaggagaag atttgggagg cgatcaagtg tattcagata tctttaagtg gtctcagaag | 2040 | atcaaattac cactgtaa 2058

<210> SEQ ID NO 51
<211> LENGTH: 1128
<212> TYPE: DNA
<213> ORGANISM: Ricinus communis

<400> SEQUENCE: 51
atgagcactg cgggtaaact aaactcatcg agctcagaat tggacttgga tcgacctaat 60
atcgaagatt atcttccttc tggatcctct attcatgaac ctcacggcaa gctccgcctg 120
cgtgatttgc tggatatttc gccagcccta acagaagcag ctggtgcaat tgttgatgac 180
tcgtttacac gatgtttcaa gtcgaatcct cctgaaccat ggaattggaa tatatatcta 240
tttcccctat ggtgttgtgg tgttgtgatt cgatatggga ttttgttccc tgtcagggtt 300
ctggtgctga cgatagggtg gataatattt ctttcagcgt acattcctgt gcatttgcta 360
ctgaaaggac atgagaagtt gaggaaaaag ttagagaggt gtttggtgga gttaatttgc 420
agcttctttg tggcatcatg gactggagtt gtcaagtacc atgggccacg gcctagcatt 480
cgacctaaac aggtttttgt ggctaatcat acctccatga ttgattttat cgtcttagag 540
cagatgactg catttgctgt tattatgcaa aaacatcctg gttgggttgg acttttacaa 600
agcactatac tagagagtgt tggttgtatc tggttcaacc gttcagaggc aaaagatcgc 660
gaaattgtag caaaaaagtt aagggaccat gttcagggtg ctgacaataa ccccccttctc 720
atatttcctg aagggacttg tgtaaataac cactatactg tgatgttcaa gaagggtgca 780
tttgaactgg ggtgtaccgt ttgcccaatt gcaatcaaat acaataaaat ttttgttgat 840
gcattttgga acagcaggaa gcagtccttt acaacgcatc tgctgcaact tatgacatca 900
tgggctgttg tttgtgatgt ctggtacttg gagccacaaa atctgagacc tggagaaaca 960
cccattgagt ttgcagagag ggtcagggac ataatatctg tacgagcagg tcttaaaaag 1020
gttccttggg atggatatct gaagtattct cgccctagcc caaaacatag agagagaaag 1080
caacaaagct ttgctgagtc agtgctacgg cgcctggagg agaagtaa 1128

<210> SEQ ID NO 52
<211> LENGTH: 2001
<212> TYPE: DNA
<213> ORGANISM: Ricinus communis

<400> SEQUENCE: 52
atggcacaac agaggcagag aaagtatttg atagaagtag agaaggccaa agaagctaaa 60
gatggaaagc catcagttgg tcctgtttat cgcagtctct ttgctaaaga tggttttcct 120
cctcccattc ccggcttgga ttcttgctgg gatgtttttc gcatgagcgt ggagaaatat 180
cctaataatc ccatgcttgg tcaccgagag tttgtgaatg gcaaggctgg taaatacgtg 240
tggcaaactt acaaacaagt atatgatttg gtcatcaaag ttggtaatgc tatacggagc 300
tgtggtgttg aaccgggaga aaaatgtggt atttatggtg ccaacagcgc tgagtggata 360
atgagcatgg aggcctgcaa tgctcacggg ctttattgtg ttcccttata tgacacttta 420
ggtgctggtg ctgtggagta tatcatatgc catgccgagg tctcaattgc ttttgtagaa 480
gaaaagaaaa ttcccgagct gttaaaaaca tttccaagtg ctgcacaata cataaaaaca 540
attgtgagct ttggcaacat tgcacgggaa caaagagaag agatggagaa gtttggttta 600
gtagcatatt cttgggaaga ctttttttaaa aactgggggg agaataaaca atatgatctc 660
ccagagaaaa agaaaagtga tatctgcact ataatgtata ccagcggaac aactggcgat 720

```
ccgaagggag taatgatttc aaatgatagc attgtgacca ttatagctgg ggtgagaagg    780
ctacttgaga gtgtgaatga acagttgact tcagaagatg tataccttc atacccttcca    840
ctcgctcata tctttgatcg agtgattgag gagctattta tttcgcacgg tgcttctata    900
gggttctggc gaggggacgt caaattatta attgaagaca ttggggagct aaaccaact    960
attttctgtg ctgttccccg tgtattagat agaatacatt caggtttgac acagaagatt   1020
tcttcaggag gcttcttaaa aaacaaatta ttcaatttag catactcata caaactaagt   1080
tgcatgaaga aggggctagc acatgatgag gcatcgccac tttctgacaa acttgtcttt   1140
gataaggtaa aacaagggtt gggaggaaaa gtacggctta ttttatcagg agctgcacct   1200
cttgctatcc atgtagaagc tttcttgcgg gtggtctcat gtgctcatgt tttgcaagga   1260
tatggtctga cagaaacctg tgctggcact tttgtctcac taccaaatga aatggcaatg   1320
cttggcacag tgggccctcc tgtgccaaat gtggatgtat gcctagaatc tgttcctgaa   1380
atgaattatg atgctctttc aagcacaccc cgtggagaaa tttgtgtgag ggggagtact   1440
gtctttgctg gttactacaa acgagaagac ctcaccaagg aggtcctgat tgatggctgg   1500
ttccacacag gtgatattgg tgaatggcaa gcagatggga gcttgaaaat tattgaccgg   1560
aagaagaaca tatttaaact tcctcaagga gaatatgttg cagttgagaa cttggagaat   1620
atttatggtc ttgcttctga tgttgattcg atatgggttt atgggaacag cttcgagtca   1680
ttccttgttg ctgttgttaa ccccaataag caagctcttg aacattgggc acaagagaat   1740
agtgtggatg gggacttcaa atcccttcgc gaaaatccaa gggcaaaaca atatatattt   1800
ggagagctca caaagattgg caaagaaaaa aagctgaaag gtttcgaatc tattaaagct   1860
gttcatcttg atcctgagcc atttgacata gaacgtgatc tcctcactcc tacatataag   1920
aaaaagaggc cccagttgct caaatactac cagaaagtta ttgacgacat gtataaaaac   1980
gcaagcaaac ccagtgcttg a                                             2001
```

<210> SEQ ID NO 53
<211> LENGTH: 945
<212> TYPE: DNA
<213> ORGANISM: Arabidopsis thaliana

<400> SEQUENCE: 53

```
atgggtggtt ccagagagtt ccgagctgag gaacattcaa atcaattcca ctctatcatc     60
gccatggcca tctggcttgg cgccattcac ttcaacgtcg ctcttgttct ctgttctctc    120
attttccttc ctccttctct atctctcatg gtcttgggct tgctctctct gtttatcttt    180
atcccaatcg atcatcgtag caaatatggt cgtaagctcg ctaggtacat atgcaagcac    240
gcgtgtaatt atttccccgt ctctctgtac gtcgaggatt acgaagcttt ccagcctaat    300
cgtgcctatg tctttggtta tgaaccacat tcggtgctac cgattggagt tgttgctctt    360
tgtgatctca cagggtttat gcctattcct aacattaaag ttcttgcaag tagtgctata    420
ttctacactc cctttctaag gcatatatgg acatggttag ggctcaccgc tgcttctagg    480
aagaatttca cttcccttt ggattctggc tacagttgtg tcttgtacc tggtggtgtg    540
caggagactt tcatatgca acatgatgct gagaatgtct tccctttcaag gagaagagga    600
tttgtgcgca tagccatgga acaggggagc cctctggttc cagtattctg ctttggtcag    660
gcacgcgtgt acaaatggtg gaagccggat tgtgatctct atcttaaact atctagagca    720
atcagattca ccccgatctg cttctgggga gttttttggat caccattacc gtgtcgacag    780
cctatgcatg tggtcgttgg taaaccaata gaagtcacaa aaactctgaa gccaactgac    840
```

```
gaagagattg ctaagtttca tggccagtat gtggaagcgc ttagggatct gtttgagagg    900
cacaagtccc gagtcggcta tgatcttgag ctgaaaattc tttga                    945

<210> SEQ ID NO 54
<211> LENGTH: 340
<212> TYPE: PRT
<213> ORGANISM: Ricinus commuinis

<400> SEQUENCE: 54

Met Gly Glu Glu Ala Asn His Asn Asn Asn Asn Asn Ile Asn Ser
  1               5                  10                  15

Asn Asp Glu Lys Asn Glu Lys Ser Asn Tyr Thr Val Val Asn Ser
                 20                  25                  30

Arg Glu Leu Tyr Pro Thr Asn Ile Phe His Ala Leu Leu Ala Leu Ser
             35                  40                  45

Ile Trp Ile Gly Ser Ile His Phe Asn Leu Phe Leu Leu Phe Ile Ser
         50                  55                  60

Tyr Leu Phe Leu Ser Phe Pro Thr Phe Leu Leu Ile Val Gly Phe
 65                  70                  75                  80

Val Val Leu Met Phe Ile Pro Ile Asp Glu His Ser Lys Leu Gly Arg
                 85                  90                  95

Arg Leu Cys Arg Tyr Val Cys Arg His Ala Cys Ser His Phe Pro Val
                100                 105                 110

Thr Leu His Val Glu Asp Met Asn Ala Phe His Ser Asp Arg Ala Tyr
                115                 120                 125

Val Phe Gly Tyr Glu Pro His Ser Val Phe Pro Leu Gly Val Ser Val
                130                 135                 140

Leu Ser Asp His Phe Ala Val Leu Pro Leu Pro Lys Met Lys Val Leu
145                 150                 155                 160

Ala Ser Asn Ala Val Phe Arg Thr Pro Val Leu Arg His Ile Trp Thr
                165                 170                 175

Trp Cys Gly Leu Thr Ser Ala Thr Lys Lys Asn Phe Thr Ala Leu Leu
                180                 185                 190

Ala Ser Gly Tyr Ser Cys Ile Val Ile Pro Gly Gly Val Gln Glu Thr
                195                 200                 205

Phe Tyr Met Lys His Gly Ser Glu Ile Ala Phe Leu Lys Ala Arg Arg
                210                 215                 220

Gly Phe Val Arg Val Ala Met Glu Met Gly Lys Pro Leu Val Pro Val
225                 230                 235                 240

Phe Cys Phe Gly Gln Ser Asn Val Tyr Lys Trp Trp Lys Pro Asp Gly
                245                 250                 255

Glu Leu Phe Met Lys Ile Ala Arg Ala Ile Lys Phe Ser Pro Ile Val
                260                 265                 270

Phe Trp Gly Val Leu Gly Ser His Leu Pro Leu Gln Arg Pro Met His
                275                 280                 285

Val Val Val Gly Lys Pro Ile Glu Val Lys Gln Asn Pro Gln Pro Thr
                290                 295                 300

Val Glu Glu Val Ser Glu Val Gln Gly Gln Phe Val Ala Ala Leu Lys
305                 310                 315                 320

Asp Leu Phe Glu Arg His Lys Ala Arg Val Gly Tyr Ala Asp Leu Thr
                325                 330                 335

Leu Glu Ile Leu
            340

<210> SEQ ID NO 55
```

```
<211> LENGTH: 521
<212> TYPE: PRT
<213> ORGANISM: Ricinus commuinis

<400> SEQUENCE: 55
```

| | | | | | | | | | | | | | | | |
|---|---|---|---|---|---|---|---|---|---|---|---|---|---|---|---|
|Met|Thr|Ile|Leu|Glu|Thr|Pro|Glu|Thr|Leu|Gly|Val|Ile|Ser|Ser|Ser|
|1| | | |5| | | |10| | | | |15| | |
|Ala|Thr|Ser|Asp|Leu|Asn|Leu|Ser|Leu|Arg|Arg|Arg|Arg|Thr|Ser|Asn|
| | | |20| | | | |25| | | | |30| | |
|Asp|Ser|Asp|Gly|Ala|Leu|Ala|Asp|Leu|Ala|Ser|Lys|Phe|Asp|Asp|Asp|
| | | | |35| | | | |40| | | | |45| |
|Asp|Asp|Val|Arg|Ser|Glu|Asp|Ser|Ala|Glu|Asn|Ile|Ile|Glu|Asp|Pro|
| |50| | | | |55| | | | |60| | | | |
|Val|Ala|Ala|Val|Thr|Glu|Leu|Ala|Thr|Ala|Lys|Ser|Asn|Gly|Lys|Asp|
|65| | | | |70| | | | |75| | | | |80|
|Cys|Val|Ala|Asn|Ser|Asn|Lys|Asp|Lys|Ile|Asp|Ser|His|Gly|Gly|Ser|
| | | | |85| | | | |90| | | | |95| |
|Ser|Asp|Phe|Lys|Leu|Ala|Tyr|Arg|Pro|Ser|Val|Pro|Ala|His|Arg|Ser|
| | | |100| | | | |105| | | | |110| | |
|Leu|Lys|Glu|Ser|Pro|Leu|Ser|Ser|Asp|Leu|Ile|Phe|Lys|Gln|Ser|His|
| | | |115| | | | |120| | | | |125| | |
|Ala|Gly|Leu|Phe|Asn|Leu|Cys|Ile|Val|Val|Leu|Val|Ala|Val|Asn|Ser|
| | |130| | | | |135| | | | |140| | | |
|Arg|Leu|Ile|Ile|Glu|Asn|Leu|Met|Lys|Tyr|Gly|Trp|Leu|Ile|Lys|Thr|
|145| | | | |150| | | | |155| | | | |160|
|Gly|Phe|Trp|Phe|Ser|Ser|Arg|Ser|Leu|Arg|Asp|Trp|Pro|Leu|Phe|Met|
| | | | |165| | | | |170| | | | |175| |
|Cys|Cys|Leu|Ser|Leu|Pro|Val|Phe|Pro|Leu|Ala|Ala|Tyr|Leu|Val|Glu|
| | | |180| | | | |185| | | | |190| | | |
|Lys|Ala|Ala|Tyr|Arg|Lys|Tyr|Ile|Ser|Pro|Pro|Ile|Val|Ile|Phe|Leu|
| | | |195| | | | |200| | | | |205| | | |
|His|Val|Ile|Ile|Thr|Ser|Ala|Ala|Val|Leu|Tyr|Pro|Ala|Ser|Val|Ile|
| | |210| | | | |215| | | | |220| | | |
|Leu|Ser|Cys|Glu|Ser|Ala|Phe|Leu|Ser|Gly|Val|Thr|Leu|Met|Glu|Leu|
|225| | | | |230| | | | |235| | | | |240|
|Ala|Cys|Met|Val|Trp|Leu|Lys|Leu|Val|Ser|Tyr|Ala|His|Thr|Asn|Tyr|
| | | | |245| | | | |250| | | | |255| |
|Asp|Met|Arg|Ala|Ile|Ala|Asp|Thr|Ile|His|Lys|Glu|Asp|Ala|Ser|Asn|
| | | |260| | | | |265| | | | |270| | |
|Ser|Ser|Ser|Thr|Glu|Tyr|Cys|His|Asp|Val|Ser|Phe|Lys|Thr|Leu|Ala|
| | | |275| | | | |280| | | | |285| | |
|Tyr|Phe|Met|Val|Ala|Pro|Thr|Leu|Cys|Tyr|Gln|Pro|Ser|Tyr|Pro|Arg|
| |290| | | | |295| | | | |300| | | | |
|Thr|Ala|Phe|Ile|Arg|Lys|Gly|Trp|Val|Phe|Arg|Gln|Phe|Val|Lys|Leu|
|305| | | | |310| | | | |315| | | | |320|
|Ile|Ile|Phe|Thr|Gly|Phe|Met|Gly|Phe|Ile|Ile|Glu|Gln|Tyr|Ile|Asn|
| | | | |325| | | | |330| | | | |335| |
|Pro|Ile|Val|Gln|Asn|Ser|Gln|His|Pro|Leu|Lys|Gly|Asp|Leu|Leu|Tyr|
| | | |340| | | | |345| | | | |350| | |
|Ala|Ile|Glu|Arg|Val|Leu|Lys|Leu|Ser|Val|Pro|Asn|Leu|Tyr|Val|Trp|
| | | |355| | | | |360| | | | |365| | |
|Leu|Cys|Leu|Phe|Tyr|Cys|Phe|Phe|His|Leu|Trp|Leu|Asn|Ile|Val|Ala|
| | |370| | | | |375| | | | |380| | | |
|Glu|Leu|Leu|Arg|Phe|Gly|Asp|Arg|Glu|Phe|Tyr|Lys|Asp|Trp|Trp|Asn|
|385| | | | |390| | | | |395| | | | |400|

```
Ala Lys Thr Val Glu Glu Tyr Trp Arg Met Trp Asn Met Pro Val His
                405                 410                 415
Lys Trp Met Val Arg His Ile Tyr Phe Pro Cys Leu Arg Arg Lys Ile
            420                 425                 430
Pro Arg Gly Val Ala Ile Val Ala Phe Phe Val Ser Ala Val Phe
        435                 440                 445
His Glu Leu Cys Ile Ala Val Pro Cys His Met Phe Lys Leu Trp Ala
    450                 455                 460
Phe Phe Gly Ile Met Phe Gln Ile Pro Leu Val Val Ile Thr Asn Tyr
465                 470                 475                 480
Phe Gln Arg Lys Phe Arg Ser Ser Met Val Gly Asn Met Ile Phe Trp
                485                 490                 495
Phe Phe Cys Ile Leu Gly Pro Met Cys Val Leu Tyr Tyr
            500                 505                 510
His Asp Leu Met Asn Arg Asp Gly Asn
        515                 520

<210> SEQ ID NO 56
<211> LENGTH: 663
<212> TYPE: PRT
<213> ORGANISM: Ricinus commuinis

<400> SEQUENCE: 56

Met Ser Ile Leu Arg Arg Leu Arg Val Gln Asn Ser Ser Gln Ile
1               5                   10                  15
Glu Ala Asp Asn Asp Glu Lys Glu Lys Glu Arg Lys Arg Lys Lys
                20                  25                  30
Glu Ile Lys Lys Trp Arg Cys Val Asp Asn Cys Cys Trp Phe Ile Gly
            35                  40                  45
Phe Ile Cys Ser Met Trp Trp Phe Leu Leu Phe Leu Tyr Asn Ala Met
    50                  55                  60
Pro Ala Ser Phe Pro Gln Tyr Val Thr Glu Ala Ile Thr Gly Pro Met
65                  70                  75                  80
Pro Asp Pro Pro Gly Val Lys Leu Arg Lys Glu Gly Leu Thr Val Lys
                85                  90                  95
His Pro Val Val Phe Val Pro Gly Ile Val Thr Gly Gly Leu Glu Leu
                100                 105                 110
Trp Glu Gly His Gln Cys Ala Asp Gly Leu Phe Arg Lys Arg Leu Trp
            115                 120                 125
Gly Gly Thr Phe Gly Asp Leu Tyr Lys Arg Pro Leu Cys Trp Val Glu
    130                 135                 140
His Met Ser Leu Asp Asn Glu Thr Gly Leu Asp Pro Pro Gly Ile Arg
145                 150                 155                 160
Val Arg Ala Val Ser Gly Leu Val Ala Ala Asp Tyr Phe Ala Ala Gly
                165                 170                 175
Tyr Phe Val Trp Ala Val Leu Ile Ala Asn Leu Ala Arg Leu Gly Tyr
                180                 185                 190
Glu Glu Lys Asn Met Tyr Met Ala Ala Tyr Asp Trp Arg Leu Ser Phe
            195                 200                 205
Gln Asn Thr Glu Ile Arg Asp Gln Ser Leu Ser Arg Ile Lys Ser Asn
    210                 215                 220
Ile Glu Leu Met Val Ala Thr Asn Gly Gly Asn Lys Val Val Val Leu
225                 230                 235                 240
Pro His Ser Met Gly Val Pro Tyr Phe Leu His Phe Met Lys Trp Val
                245                 250                 255
```

```
Glu Ala Pro Ala Pro Met Gly Gly Gly Gly Pro Asp Trp Cys Ala
            260                 265                 270

Lys His Ile Lys Ala Val Ile Asn Ile Gly Gly Pro Phe Leu Gly Val
        275                 280                 285

Pro Lys Ala Ile Ser Ser Leu Phe Ser Asn Glu Gly Arg Asp Ile Ala
    290                 295                 300

Ala Ala Arg Ala Phe Ala Pro Gly Phe Leu Asp Lys Asp Val Phe Gly
305                 310                 315                 320

Leu Gln Thr Phe Gln His Ala Met Arg Leu Thr Arg Thr Trp Asp Ser
            325                 330                 335

Thr Met Ser Met Ile Pro Lys Gly Gly Glu Thr Ile Trp Gly Gly Leu
            340                 345                 350

Asp Trp Ser Pro Glu Gly Val Tyr Asn Cys Gly Ser Asn Thr Pro Lys
            355                 360                 365

Asn Asn Asn Thr Gln Thr Ala Gly Gln Thr Lys Gly Thr Ser Ser
        370                 375                 380

Phe Thr Glu Gly Val Asn Tyr Gly Arg Ile Ile Ser Phe Gly Lys Asp
385                 390                 395                 400

Val Ala Glu Leu His Ser Ser Lys Ile Asp Arg Ile Asp Phe Arg Asp
            405                 410                 415

Ala Val Lys Gly Asn Arg Val Ala Asn Asn Cys Asp Ile Trp Thr Glu
            420                 425                 430

Tyr Gln Glu Met Gly Ile Gly Gly Ile Lys Ala Val Ala Asp Tyr Lys
            435                 440                 445

Val Tyr Thr Ala Gly Ser Val Ile Asp Leu Leu His Phe Val Ala Pro
    450                 455                 460

Lys Leu Met Ala Arg Gly Asp Ala His Phe Ser His Gly Ile Ala Asp
465                 470                 475                 480

Asn Leu Asp Asp Pro Lys Tyr Glu His Tyr Lys Tyr Trp Ser Asn Pro
            485                 490                 495

Leu Glu Thr Arg Leu Pro Asp Ala Pro Glu Met Glu Leu Tyr Ser Met
            500                 505                 510

Tyr Gly Ile Gly Ile Pro Thr Glu Arg Ala Tyr Ile Tyr Lys Leu Thr
            515                 520                 525

Leu Thr Ser Glu Cys Ala Ile Pro Phe Gln Ile Asp Thr Ser Val Thr
    530                 535                 540

Gly Gly Ser Glu Asn Ser Cys Leu Lys Asp Gly Thr Leu Asn Val Asn
545                 550                 555                 560

Gly Asp Glu Thr Val Pro Val Leu Ser Ala Gly Phe Met Phe Ala Lys
            565                 570                 575

Gly Trp Arg Gly Lys Thr Arg Phe Asn Pro Ser Gly Ile His Thr Tyr
            580                 585                 590

Ile Arg Glu Tyr Asn His Ala Pro Pro Ala Asn Leu Leu Glu Gly Arg
            595                 600                 605

Gly Thr Gln Ser Gly Ala His Val Asp Ile Leu Gly Asn Phe Ala Leu
            610                 615                 620

Ile Glu Asp Val Leu Arg Ile Ala Ala Gly Ala Arg Gly Glu Asp Leu
625                 630                 635                 640

Gly Gly Asp Arg Val Tyr Ser Asp Ile Phe Lys Trp Ser Glu Lys Ile
            645                 650                 655

Asn Leu Ala Ala Ile Asp Ser
            660
```

<210> SEQ ID NO 57
<211> LENGTH: 685
<212> TYPE: PRT
<213> ORGANISM: Ricinus communis

<400> SEQUENCE: 57

```
Met Pro Val Ile Arg Arg Lys Lys Pro Thr Ser Glu Pro Asn Lys Asn
 1               5                  10                  15

Ser Ala Ser Asp Ser Lys Thr Pro Ser Glu Glu Glu Glu His Glu Gln
            20                  25                  30

Glu Gln Glu Gln Glu Glu Asp Lys Asn Asn Lys Lys Lys Tyr Pro Lys
        35                  40                  45

Lys Lys Ser Ser Glu Ile Asn Ala Lys Lys Trp Ser Cys Ile Asp Ser
    50                  55                  60

Cys Cys Trp Phe Val Gly Cys Ile Cys Val Thr Trp Trp Val Leu Leu
65                  70                  75                  80

Phe Leu Tyr Asn Ala Val Pro Ala Ser Leu Pro Gln Tyr Val Thr Glu
                85                  90                  95

Ala Ile Thr Gly Pro Leu Pro Asp Pro Pro Gly Val Lys Leu Lys Lys
            100                 105                 110

Glu Gly Leu Thr Ala Lys His Pro Val Val Phe Val Pro Gly Ile Val
        115                 120                 125

Thr Ala Gly Leu Glu Leu Trp Glu Gly His Gln Cys Ala Asp Gly Leu
    130                 135                 140

Phe Arg Lys Arg Leu Trp Gly Gly Thr Phe Gly Glu Val Tyr Lys Arg
145                 150                 155                 160

Pro Leu Cys Trp Val Glu His Met Ser Leu Asp Asn Glu Thr Gly Leu
                165                 170                 175

Asp Pro Pro Gly Ile Arg Val Arg Pro Val Ser Gly Leu Val Ala Ala
            180                 185                 190

Asp Tyr Phe Ala Pro Gly Tyr Phe Val Trp Ala Val Leu Ile Ala Asn
        195                 200                 205

Leu Ala Arg Ile Gly Tyr Glu Glu Lys Thr Met Phe Met Ala Ser Tyr
    210                 215                 220

Asp Trp Arg Leu Ser Phe Gln Asn Thr Glu Val Arg Asp Gln Thr Leu
225                 230                 235                 240

Ser Arg Met Lys Ser Asn Ile Glu Leu Met Val Ser Ile Asn Gly Gly
                245                 250                 255

Asn Lys Ala Val Ile Val Pro His Ser Met Gly Val Leu Tyr Phe Leu
            260                 265                 270

His Phe Met Lys Trp Val Glu Ala Pro Ala Pro Met Gly Gly Gly Gly
        275                 280                 285

Gly Pro Asp Trp Cys Ala Lys His Ile Lys Ala Val Met Asn Ile Gly
    290                 295                 300

Gly Pro Phe Leu Gly Val Pro Lys Ala Val Ala Gly Leu Phe Ser Ala
305                 310                 315                 320

Glu Ala Arg Asp Ile Ala Val Ala Arg Ala Ile Ala Pro Gly Phe Leu
                325                 330                 335

Asp Asn Asp Met Phe Arg Leu Gln Thr Leu Gln His Met Met Arg Met
            340                 345                 350

Ser Arg Thr Trp Asp Ser Thr Met Ser Met Ile Pro Arg Gly Gly Asp
        355                 360                 365

Thr Ile Trp Gly Asp Leu Asp Trp Ser Pro Glu Glu Gly Tyr Ile Pro
    370                 375                 380

Arg Lys Lys Arg Gln Arg Asn Asn Ala Thr Asp Asn Val Asn Glu Gly
```

```
            385                 390                 395                 400
Gly Ala Glu Ser Glu Ile Ser Gln Arg Lys Ile Val Arg Tyr Gly Arg
                405                 410                 415

Met Ile Ser Phe Gly Lys Asn Ile Ala Glu Ala Pro Ser Tyr Asp Ile
                420                 425                 430

Glu Arg Ile Asp Phe Arg Asp Ala Val Lys Gly Arg Ser Val Ala Asn
                435                 440                 445

Asn Thr Cys Leu Asp Val Trp Thr Glu Tyr His Glu Met Gly Phe Gly
                450                 455                 460

Gly Ile Lys Ala Val Ala Glu Tyr Lys Val Tyr Thr Ala Gly Ser Thr
465                 470                 475                 480

Ile Glu Leu Leu Gln Phe Val Ala Pro Lys Met Met Glu Arg Gly Ser
                485                 490                 495

Ala His Phe Ser Tyr Gly Ile Ala Asp Asn Leu Glu Asp Pro Lys Tyr
                500                 505                 510

Glu His Tyr Lys Tyr Trp Ser Asn Pro Leu Glu Thr Lys Leu Pro Asn
                515                 520                 525

Ala Pro Glu Met Glu Ile Phe Ser Met Tyr Gly Val Gly Ile Pro Thr
                530                 535                 540

Glu Arg Ala Tyr Val Tyr Glu Phe Ser Pro Ala Ala Glu Cys Tyr Ile
545                 550                 555                 560

Pro Phe Gln Ile Asp Thr Ser Ala Asn Asp Gly Asp Glu Asp Gly Cys
                565                 570                 575

Leu Lys Asp Gly Val Tyr Thr Val Asp Gly Asp Glu Thr Val Pro Val
                580                 585                 590

Leu Ser Ala Gly Phe Met Cys Ala Lys Ala Trp Arg Gly Lys Thr Arg
                595                 600                 605

Phe Asn Pro Ser Gly Ser Arg Thr Tyr Ile Arg Glu Tyr Asp His Ser
                610                 615                 620

Pro Pro Ala Asn Leu Leu Glu Gly Arg Gly Thr Gln Ser Gly Ala His
625                 630                 635                 640

Val Asp Ile Met Gly Asn Phe Ala Leu Ile Glu Asp Ile Met Arg Val
                645                 650                 655

Ala Ala Gly Ala Thr Gly Glu Asp Leu Gly Gly Asp Gln Val Tyr Ser
                660                 665                 670

Asp Ile Phe Lys Trp Ser Gln Lys Ile Lys Leu Pro Leu
                675                 680                 685

<210> SEQ ID NO 58
<211> LENGTH: 375
<212> TYPE: PRT
<213> ORGANISM: Ricinus commuinis

<400> SEQUENCE: 58

Met Ser Thr Ala Gly Lys Leu Asn Ser Ser Ser Glu Leu Asp Leu
1               5                   10                  15

Asp Arg Pro Asn Ile Glu Asp Tyr Leu Pro Ser Gly Ser Ser Ile His
                20                  25                  30

Glu Pro His Gly Lys Leu Arg Leu Arg Asp Leu Leu Asp Ile Ser Pro
                35                  40                  45

Ala Leu Thr Glu Ala Ala Gly Ala Ile Val Asp Asp Ser Phe Thr Arg
                50                  55                  60

Cys Phe Lys Ser Asn Pro Pro Glu Pro Trp Asn Trp Asn Ile Tyr Leu
65                  70                  75                  80

Phe Pro Leu Trp Cys Cys Gly Val Val Ile Arg Tyr Gly Ile Leu Phe
```

```
                        85                  90                  95
Pro Val Arg Val Leu Val Leu Thr Ile Gly Trp Ile Ile Phe Leu Ser
            100                 105                 110
Ala Tyr Ile Pro Val His Leu Leu Lys Gly His Glu Lys Leu Arg
            115                 120                 125
Lys Lys Leu Glu Arg Cys Leu Val Glu Leu Ile Cys Ser Phe Phe Val
130                 135                 140
Ala Ser Trp Thr Gly Val Val Lys Tyr His Gly Pro Arg Pro Ser Ile
145                 150                 155                 160
Arg Pro Lys Gln Val Phe Val Ala Asn His Thr Ser Met Ile Asp Phe
            165                 170                 175
Ile Val Leu Glu Gln Met Thr Ala Phe Ala Val Ile Met Gln Lys His
            180                 185                 190
Pro Gly Trp Val Gly Leu Leu Gln Ser Thr Ile Leu Glu Ser Val Gly
            195                 200                 205
Cys Ile Trp Phe Asn Arg Ser Glu Ala Lys Asp Arg Glu Ile Val Ala
            210                 215                 220
Lys Lys Leu Arg Asp His Val Gln Gly Ala Asp Asn Asn Pro Leu Leu
225                 230                 235                 240
Ile Phe Pro Glu Gly Thr Cys Val Asn Asn His Tyr Thr Val Met Phe
            245                 250                 255
Lys Lys Gly Ala Phe Glu Leu Gly Cys Thr Val Cys Pro Ile Ala Ile
            260                 265                 270
Lys Tyr Asn Lys Ile Phe Val Asp Ala Phe Trp Asn Ser Arg Lys Gln
            275                 280                 285
Ser Phe Thr Thr His Leu Leu Gln Leu Met Thr Ser Trp Ala Val Val
            290                 295                 300
Cys Asp Val Trp Tyr Leu Glu Pro Gln Asn Leu Arg Pro Gly Glu Thr
305                 310                 315                 320
Pro Ile Glu Phe Ala Glu Arg Val Arg Asp Ile Ile Ser Val Arg Ala
            325                 330                 335
Gly Leu Lys Lys Val Pro Trp Asp Gly Tyr Leu Lys Tyr Ser Arg Pro
            340                 345                 350
Ser Pro Lys His Arg Glu Arg Lys Gln Gln Ser Phe Ala Glu Ser Val
            355                 360                 365
Leu Arg Arg Leu Glu Glu Lys
            370                 375

<210> SEQ ID NO 59
<211> LENGTH: 666
<212> TYPE: PRT
<213> ORGANISM: Ricinus commuinis

<400> SEQUENCE: 59

Met Ala Gln Gln Arg Gln Arg Lys Tyr Leu Ile Glu Val Glu Lys Ala
1               5                   10                  15
Lys Glu Ala Lys Asp Gly Lys Pro Ser Val Gly Pro Val Tyr Arg Ser
            20                  25                  30
Leu Phe Ala Lys Asp Gly Phe Pro Pro Ile Pro Gly Leu Asp Ser
            35                  40                  45
Cys Trp Asp Val Phe Arg Met Ser Val Glu Lys Tyr Pro Asn Asn Pro
            50                  55                  60
Met Leu Gly His Arg Glu Phe Val Asn Gly Lys Ala Gly Lys Tyr Val
65                  70                  75                  80
Trp Gln Thr Tyr Lys Gln Val Tyr Asp Leu Val Ile Lys Val Gly Asn
```

-continued

```
                85                  90                  95
Ala Ile Arg Ser Cys Gly Val Glu Pro Gly Glu Lys Cys Gly Ile Tyr
            100                 105                 110
Gly Ala Asn Ser Ala Glu Trp Ile Met Ser Met Glu Ala Cys Asn Ala
            115                 120                 125
His Gly Leu Tyr Cys Val Pro Leu Tyr Asp Thr Leu Gly Ala Gly Ala
            130                 135                 140
Val Glu Tyr Ile Ile Cys His Ala Glu Val Ser Ile Ala Phe Val Glu
145                 150                 155                 160
Glu Lys Lys Ile Pro Glu Leu Leu Lys Thr Phe Pro Ser Ala Ala Gln
            165                 170                 175
Tyr Ile Lys Thr Ile Val Ser Phe Gly Asn Ile Ala Arg Glu Gln Arg
            180                 185                 190
Glu Glu Met Glu Lys Phe Gly Leu Val Ala Tyr Ser Trp Glu Asp Phe
            195                 200                 205
Phe Lys Asn Trp Gly Glu Asn Lys Gln Tyr Asp Leu Pro Glu Lys Lys
            210                 215                 220
Lys Ser Asp Ile Cys Thr Ile Met Tyr Thr Ser Gly Thr Thr Gly Asp
225                 230                 235                 240
Pro Lys Gly Val Met Ile Ser Asn Asp Ser Ile Val Thr Ile Ile Ala
            245                 250                 255
Gly Val Arg Arg Leu Leu Glu Ser Val Asn Glu Gln Leu Thr Ser Glu
            260                 265                 270
Asp Val Tyr Leu Ser Tyr Leu Pro Leu Ala His Ile Phe Asp Arg Val
            275                 280                 285
Ile Glu Glu Leu Phe Ile Ser His Gly Ala Ser Ile Gly Phe Trp Arg
            290                 295                 300
Gly Asp Val Lys Leu Leu Ile Glu Asp Ile Gly Glu Leu Lys Pro Thr
305                 310                 315                 320
Ile Phe Cys Ala Val Pro Arg Val Leu Asp Arg Ile His Ser Gly Leu
            325                 330                 335
Thr Gln Lys Ile Ser Ser Gly Gly Phe Leu Lys Asn Lys Leu Phe Asn
            340                 345                 350
Leu Ala Tyr Ser Tyr Lys Leu Ser Cys Met Lys Lys Gly Leu Ala His
            355                 360                 365
Asp Glu Ala Ser Pro Leu Ser Asp Lys Leu Val Phe Asp Lys Val Lys
            370                 375                 380
Gln Gly Leu Gly Gly Lys Val Arg Leu Ile Leu Ser Gly Ala Ala Pro
385                 390                 395                 400
Leu Ala Ile His Val Glu Ala Phe Leu Arg Val Val Ser Cys Ala His
            405                 410                 415
Val Leu Gln Gly Tyr Gly Leu Thr Glu Thr Cys Ala Gly Thr Phe Val
            420                 425                 430
Ser Leu Pro Asn Glu Met Ala Met Leu Gly Thr Val Gly Pro Pro Val
            435                 440                 445
Pro Asn Val Asp Val Cys Leu Glu Ser Val Pro Glu Met Asn Tyr Asp
450                 455                 460
Ala Leu Ser Ser Thr Pro Arg Gly Glu Ile Cys Val Arg Gly Ser Thr
465                 470                 475                 480
Val Phe Ala Gly Tyr Tyr Lys Arg Glu Asp Leu Thr Lys Glu Val Leu
            485                 490                 495
Ile Asp Gly Trp Phe His Thr Gly Asp Ile Gly Glu Trp Gln Ala Asp
            500                 505                 510
```

```
Gly Ser Leu Lys Ile Ile Asp Arg Lys Lys Asn Ile Phe Lys Leu Pro
            515                 520                 525

Gln Gly Glu Tyr Val Ala Val Glu Asn Leu Glu Asn Ile Tyr Gly Leu
        530                 535                 540

Ala Ser Asp Val Asp Ser Ile Trp Val Tyr Gly Asn Ser Phe Glu Ser
545                 550                 555                 560

Phe Leu Val Ala Val Asn Pro Asn Lys Gln Ala Leu Glu His Trp
            565                 570                 575

Ala Gln Glu Asn Ser Val Asp Gly Asp Phe Lys Ser Leu Arg Glu Asn
        580                 585                 590

Pro Arg Ala Lys Gln Tyr Ile Ile Gly Glu Leu Thr Lys Ile Gly Lys
            595                 600                 605

Glu Lys Lys Leu Lys Gly Phe Glu Ser Ile Lys Ala Val His Leu Asp
610                 615                 620

Pro Glu Pro Phe Asp Ile Glu Arg Asp Leu Leu Thr Pro Thr Tyr Lys
625                 630                 635                 640

Lys Lys Arg Pro Gln Leu Leu Lys Tyr Tyr Gln Lys Val Ile Asp Asp
            645                 650                 655

Met Tyr Lys Asn Ala Ser Lys Pro Ser Ala
            660                 665

<210> SEQ ID NO 60
<211> LENGTH: 314
<212> TYPE: PRT
<213> ORGANISM: Arabidopsis thaliana

<400> SEQUENCE: 60

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65                  70                  75                  80

Ala Cys Asn Tyr Phe Pro Val Ser Leu Tyr Val Glu Asp Tyr Glu Ala
                85                  90                  95

Phe Gln Pro Asn Arg Ala Tyr Val Phe Gly Tyr Glu Pro His Ser Val
            100                 105                 110

Leu Pro Ile Gly Val Val Ala Leu Cys Asp Leu Thr Gly Phe Met Pro
        115                 120                 125

Ile Pro Asn Ile Lys Val Leu Ala Ser Ser Ala Ile Phe Tyr Thr Pro
    130                 135                 140

Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Arg Gly Phe Val Arg Ile Ala Met Glu Gln
        195                 200                 205

Gly Ser Pro Leu Val Pro Val Phe Cys Phe Gly Gln Ala Arg Val Tyr
    210                 215                 220
```

```
Lys Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
        245                 250                 255

Pro Cys Arg Gln Pro Met His Val Val Val Gly Lys Pro Ile Glu Val
            260                 265                 270

Thr Lys Thr Leu Lys Pro Thr Asp Glu Glu Ile Ala Lys Phe His Gly
        275                 280                 285

Gln Tyr Val Glu Ala Leu Arg Asp Leu Phe Glu Arg His Lys Ser Arg
        290                 295                 300

Val Gly Tyr Asp Leu Glu Leu Lys Ile Leu
305                 310

<210> SEQ ID NO 61
<211> LENGTH: 1440
<212> TYPE: DNA
<213> ORGANISM: Ricinus communis

<400> SEQUENCE: 61
gccaccttaa gcgagcgccg cacacgaagc ctcctttcac acttggtgac ctcaaatcaa      60
acaccacacc ttataactta gtcttaagag agagagagag agagaggaga catttctctt     120
ctctgagata agcacttctc ttccagacat cgaagcctca ggaaagtgct taaaagagc      180 ttaagaatgg gaggtggtgg tcgcatgtct actgtcataa ccagcaacaa cagtgagaag     240
aaaggaggaa gcagccacct taagcgagcg ccgcacacga agcctccttt cacacttggt     300
gacctcaaga gagccatccc accccattgc tttgaacgct cttttgtgcg ctcattctcc     360
tatgttgcct atgatgtctg cttaagtttt cttttctact cgatcgccac caacttcttc     420
ccttacatct cttctccgct ctcgtatgtc gcttggctgg tttactggct cttccaaggc     480
tgcattctca ctggtctttg ggtcatcggc catgaatgtg ccatcatgc ttttagtgag      540 tatcagctgg ctgatgacat tgttggccta attgtccatt ctgcacttct ggttccatat     600
ttttcatgga aatatagcca tcgccgccac cattctaaca taggatctct cgagcgagac     660
gaagtgttcg tcccgaaatc aaagtcgaaa atttcatggt attctaagta ctcaaacaac     720
ccgccaggtc gagttttgac acttgctgcc acgctcctcc ttggctggcc tttatactta     780
gctttcaatg tctctggtag accttacgat cgctttgctt gccattatga tccctatggc     840
ccaatatttt ccgaaagaga aaggcttcag atttacattg ctgacctcgg aatctttgcc     900
acaacgtttg tgctttatca ggctacaatg gcaaaaaggt tggcttgggt aatgcgtatc     960
tatggggtgc cattgcttat tgttaactgt tccttgtta tgatcacata cttgcagcac    1020
actcacccag ctattccacg ctatggctca tcggaatggg attggctccg gggagcaatg    1080
gtgactgtcg atagagatta tggggtgttg aataaagtat tccataacat tgcagacact    1140
catgtagctc atcatctctt tgctacagtg ccacattacc atgcaatgga ggccactaaa    1200
gcaatcaagc ctataatggg tgagtattac cggtatgatg taccccatt ttacaaggca     1260 ttgtggaggg aggcaaagga gtgcttgttc gtcgagccag atgaaggagc tcctacacaa    1320
ggcgttttct ggtaccggaa caagtattaa aaaagtgtca tgtagcctgt ttctttaaga    1380
gaagtaatta aacaagaag gaatgtgtgt gtagtgtaat gtgttctaat aaagaaggca    1440

<210> SEQ ID NO 62
<211> LENGTH: 387
<212> TYPE: PRT
<213> ORGANISM: Ricinus communis
```

-continued

```
<400> SEQUENCE: 62

Met Gly Gly Gly Arg Met Ser Thr Val Ile Thr Ser Asn Asn Ser
 1               5                  10                  15

Glu Lys Lys Gly Gly Ser Ser His Leu Lys Arg Ala Pro His Thr Lys
             20                  25                  30

Pro Pro Phe Thr Leu Gly Asp Leu Lys Arg Ala Ile Pro Pro His Cys
         35                  40                  45

Phe Glu Arg Ser Phe Val Arg Ser Phe Ser Tyr Val Ala Tyr Asp Val
     50                  55                  60

Cys Leu Ser Phe Leu Phe Tyr Ser Ile Ala Thr Asn Phe Phe Pro Tyr
 65                  70                  75                  80

Ile Ser Ser Pro Leu Ser Tyr Val Ala Trp Leu Val Tyr Trp Leu Phe
                 85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 63
<211> LENGTH: 333
```

```
<212> TYPE: PRT
<213> ORGANISM: Barley

<400> SEQUENCE: 63

Met Gly Ala Asn Gly Ala Leu Glu Glu Glu Arg Pro Arg Ala Asp Gly
  1               5                  10                  15

Gly Asp Glu Glu Gly Gly Ala Thr Val Phe Arg Gly Thr Asn Tyr Ser
             20                  25                  30

Leu Pro Arg Thr Ile Ala Ala Leu Ala Leu Trp Leu Gly Gly Ile His
         35                  40                  45

Phe Asn Val Leu Leu Ile Leu Ala Ser Leu Phe Leu Phe Pro Leu Arg
     50                  55                  60

Leu Ala Ala Leu Val Val Ala Leu Gln Leu Met Phe Met Phe Ile Pro
 65                  70                  75                  80

Leu Asn Asp Glu Asp Lys Leu Gly Arg Lys Ile Gly Arg Phe Ile Cys
                 85                  90                  95

Lys Tyr Ala Met Gly Tyr Phe Pro Ile Ser Leu His Val Glu Asp Tyr
            100                 105                 110

Glu Ala Phe Asp Ser Ser Arg Ala Tyr Val Phe Gly Tyr Glu Pro His
            115                 120                 125

Ser Val Leu Pro Ile Gly Val Ala Leu Ala Asn His Val Gly Phe
        130                 135                 140

Met Pro Leu Pro Lys Leu Lys Val Leu Ala Ser Ser Ala Val Phe His
145                 150                 155                 160

Thr Pro Phe Leu Arg Gln Ile Trp Thr Trp Ile Gly Leu Ile Ala Ala
                165                 170                 175

Thr Arg Lys Asn Phe Tyr Ser Tyr Leu Ala Ala Gly Tyr Ser Cys Val
            180                 185                 190

Val Val Pro Gly Gly Ile Gln Glu Ile Leu His Met Asp His Asp Ser
        195                 200                 205

Glu Val Ala Phe Leu Lys Ser Arg Lys Gly Phe Val Lys Ile Ala Met
    210                 215                 220

Gln Ser Gly Cys Pro Leu Val Pro Val Phe Cys Phe Gly Gln Ser Lys
225                 230                 235                 240

Ala Tyr Lys Trp Trp Arg Pro Gly Gly Lys Leu Phe Val Asn Ile Ala
                245                 250                 255

Arg Ala Leu Lys Phe Thr Pro Ile Ile Phe Trp Gly Arg Tyr Gly Thr
            260                 265                 270

Pro Ile Ala Phe Ser Ser Pro Met His Val Val Gly Arg Pro Ile
        275                 280                 285

Glu Leu Lys Lys Asn Pro Leu Pro Thr Ile Asp Glu Ile Asn Glu Val
    290                 295                 300

His Gly Gln Phe Ile Gly Ala Leu Gln Glu Leu Phe Glu Lys Tyr Lys
305                 310                 315                 320

Thr Lys Ala Gly Tyr Pro Gly Leu His Leu Arg Val Leu
                325                 330

<210> SEQ ID NO 64
<211> LENGTH: 336
<212> TYPE: PRT
<213> ORGANISM: Wheat

<400> SEQUENCE: 64

Met Gly Ala Asn Gly Ala Leu Glu Gly Glu Glu Arg Pro Arg Ala
  1               5                  10                  15

Asp Gly Glu Glu Glu Glu Glu Gly Gly Ala Thr Val Phe Arg Gly Thr
```

```
                    20                  25                  30
Asn Tyr Ser Leu Pro Arg Thr Ile Ala Ala Leu Ala Leu Trp Leu Gly
             35                  40                  45

Gly Ile His Phe Asn Val Ile Leu Ile Leu Ala Ser Leu Phe Leu Phe
 50                  55                  60

Pro Leu Arg Leu Ala Ala Leu Val Val Ala Leu Gln Leu Val Phe Met
 65                  70                  75                  80

Phe Thr Pro Leu Asn Asp Glu Asp Lys Leu Gly Arg Lys Ile Gly Arg
             85                  90                  95

Phe Ile Cys Lys Tyr Ala Met Gly Tyr Phe Pro Ile Ser Leu His Val
            100                 105                 110

Glu Asp Tyr Asp Ala Phe Asp Ser Ser Arg Ala Tyr Val Phe Gly Tyr
            115                 120                 125

Glu Pro His Ser Val Leu Pro Ile Gly Val Ala Ala Leu Ala Asn His
            130                 135                 140

Val Gly Phe Met Pro Leu Pro Lys Leu Lys Val Leu Ala Ser Ser Ala
145                 150                 155                 160

Val Phe His Thr Pro Phe Leu Arg Gln Ile Trp Thr Trp Ile Gly Leu
                165                 170                 175

Ile Ala Ala Thr Arg Lys Asn Phe Tyr Ser Tyr Leu Ala Ala Gly Tyr
                180                 185                 190

Ser Cys Val Val Val Pro Gly Gly Ile Gln Glu Ile Leu His Met Asp
            195                 200                 205

His Asp Ser Glu Val Ala Phe Leu Asn Ser Arg Lys Gly Phe Val Lys
            210                 215                 220

Ile Ala Met Gln Ala Gly Cys Pro Leu Val Pro Val Phe Cys Phe Gly
225                 230                 235                 240

Gln Ser Lys Ala Tyr Arg Trp Trp Arg Pro Gly Gly Lys Leu Phe Val
                245                 250                 255

Asn Ile Ala Arg Ala Leu Lys Phe Thr Pro Ile Ile Phe Trp Gly Arg
            260                 265                 270

Tyr Gly Thr Pro Ile Ala Phe Ser Ala Pro Met His Val Val Val Gly
            275                 280                 285

Arg Pro Ile Glu Leu Lys Lys Asn Pro Leu Pro Thr Ile Asp Glu Ile
290                 295                 300

Asn Glu Val His Gly Gln Phe Val Gly Ala Leu Gln Glu Leu Phe Glu
305                 310                 315                 320

Lys Tyr Lys Thr Lys Ala Gly Tyr Pro Gly Leu His Leu Arg Val Leu
                325                 330                 335

<210> SEQ ID NO 65
<211> LENGTH: 317
<212> TYPE: PRT
<213> ORGANISM: Brassica napus

<400> SEQUENCE: 65

Met Gly Lys Val Ile Asp Phe Gly Ala Glu Asp His Ile Pro Ser Asn
 1               5                  10                  15

Ile Phe His Ala Val Thr Ala Ile Ser Ile Cys Leu Ser Ala Ile Tyr
                20                  25                  30

Leu Asn Leu Ala Leu Val Leu Ile Ser Leu Phe Phe Leu Pro Pro Ser
             35                  40                  45

Phe Ser Leu Leu Val Leu Gly Leu Leu Ser Leu Phe Ile Ile Ile Pro
 50                  55                  60

Ile Asp Asp Arg Ser Lys Tyr Gly Leu Lys Leu Ala Arg Tyr Ile Cys
```

```
                65                  70                  75                  80
Lys His Ala Ala Ser Tyr Phe Pro Val Thr Leu His Val Glu Asp Tyr
                        85                  90                  95
Glu Ala Phe Lys Pro Asp Arg Ser Tyr Val Phe Gly Tyr Glu Pro His
                100                 105                 110
Ser Val Trp Pro Phe Gly Ala Val Leu Val Asp Leu Ala Gly Phe
            115                 120                 125
Met Pro Leu Pro Asn Ile Lys Leu Leu Ala Ser Asn Ala Ile Phe Tyr
        130                 135                 140
Thr Pro Phe Leu Arg His Met Trp Ala Trp Leu Gly Leu Ala Ser Ala
145                 150                 155                 160
Ser Arg Lys Ser Phe Ser Ser Leu Leu Glu Ser Gly Tyr Ser Cys Ile
                        165                 170                 175
Leu Val Pro Gly Gly Val Gln Glu Thr Phe His Leu Gln His Asp Val
                180                 185                 190
Glu Asn Val Phe Leu Ser Ser Arg Arg Gly Phe Val Arg Ile Ala Met
            195                 200                 205
Glu Gln Gly Ala Pro Leu Val Pro Val Phe Cys Phe Gly Gln Ser Arg
        210                 215                 220
Ala Tyr Lys Trp Trp Lys Pro Asp Cys Asp Leu Tyr Phe Lys Leu Ala
225                 230                 235                 240
Lys Ala Ile Arg Phe Thr Pro Ile Cys Phe Trp Gly Val Phe Gly Ser
                        245                 250                 255
Pro Ile Pro Tyr Arg His Pro Ile His Val Val Gly Lys Pro Ile
                260                 265                 270
Gln Val Ala Lys Ser Leu Gln Pro Thr Asp Glu Glu Ile Asp Glu Leu
            275                 280                 285
Arg Gly Gln Phe Val Glu Ala Leu Lys Asp Leu Phe Glu Arg His Lys
        290                 295                 300
Ala Gly Ala Gly Tyr Ser Asp Leu Gln Leu Asn Ile Leu
305                 310                 315

<210> SEQ ID NO 66
<211> LENGTH: 333
<212> TYPE: PRT
<213> ORGANISM: Maize

<400> SEQUENCE: 66

Met Gly Ala Gly Thr Asn Asn Gly Leu Ser Asn Gly Ala Ala Gly
  1               5                  10                  15
Glu Arg Ala Asp Asp Gly Thr Thr Val Phe Arg Gly Thr Ala Tyr Ser
                 20                  25                  30
Pro Leu Arg Thr Thr Val Ala Leu Ala Leu Trp Leu Gly Ala Ile His
             35                  40                  45
Phe Asn Ala Phe Leu Val Leu Ala Ser Leu Phe Leu Phe Pro Arg Arg
         50                  55                  60
Val Ala Ala Leu Val Leu Ala Thr Gln Leu Phe Phe Met Phe Leu Pro
65                  70                  75                  80
Leu Ser Asp Lys Ser Arg Leu Gly Arg Lys Ile Ala Arg Phe Ile Ser
                         85                  90                  95
Lys Tyr Val Ile Gly Tyr Phe Pro Val Thr Leu His Val Glu Asp Tyr
                100                 105                 110
Gly Ala Phe Asp Pro Asn Arg Ala Tyr Val Phe Gly Tyr Glu Pro His
             115                 120                 125
Ser Val Leu Pro Ile Ala Val Gly Ile Leu Gly Asp Leu Val Gly Phe
```

```
            130                 135                 140
Met Pro Leu Pro Lys Met Lys Ile Leu Ala Ser Ser Ala Val Phe Tyr
145                 150                 155                 160

Thr Pro Phe Leu Arg Gln Ile Trp Thr Trp Leu Gly Leu Ala Pro Ala
                165                 170                 175

Ser Arg Lys Ser Phe Tyr Ser Tyr Leu Gly Ala Gly Tyr Ser Cys Ile
            180                 185                 190

Ile Val Pro Gly Gly Val Gln Glu Ile Leu His Met Asp His Asp Ser
        195                 200                 205

Glu Val Ala Phe Leu Lys Pro Arg Lys Gly Phe Val Lys Ile Ala Ile
    210                 215                 220

Glu Met Gly Cys Pro Val Val Pro Val Phe Ala Phe Gly Gln Ser Tyr
225                 230                 235                 240

Val Tyr Lys Trp Trp Arg Pro Gly Gly Lys Leu Ile Val Lys Ile Ala
                245                 250                 255

Arg Ala Ile Lys Phe Ser Pro Ile Ile Phe Trp Gly Lys Leu Gly Thr
            260                 265                 270

Pro Ile Pro Phe Ala Thr Pro Met His Val Ile Val Gly Arg Pro Ile
        275                 280                 285

Glu Val Val Lys Asn Pro Gln Pro Thr Ile Asp Glu Ile Asn Gln Val
    290                 295                 300

His Gly Gln Phe Val Val Ala Met Gln Asp Leu Phe Glu Lys Tyr Lys
305                 310                 315                 320

Ser Arg Thr Gly Tyr Pro Asp Leu Gln Leu Arg Val Leu
                325                 330

<210> SEQ ID NO 67
<211> LENGTH: 340
<212> TYPE: PRT
<213> ORGANISM: Rice

<400> SEQUENCE: 67

Met Gly Ala Asn Gly Asn Asp Val Val Ala Ala Ala Ala Gly Glu
1                   5                   10                  15

Ser Pro Met Gly Ala Ala Arg Val Val Ala Glu Gly Gly Ala Thr Val
                20                  25                  30

Phe Arg Gly Ala Asp Tyr Ser Leu Pro Arg Thr Thr Val Ala Leu Ala
            35                  40                  45

Leu Trp Leu Gly Gly Ile His Phe Asn Val Phe Leu Val Leu Ala Ser
        50                  55                  60

Leu Phe Leu Phe Pro Leu Arg Val Ala Ala Met Val Val Ala Phe Gln
65                  70                  75                  80

Leu Leu Phe Met Leu Ile Pro Leu Asn Asp Lys Asp Lys Leu Gly Arg
                85                  90                  95

Lys Ile Ala Arg Phe Ile Cys Arg Tyr Ala Met Gly Tyr Phe Pro Ile
            100                 105                 110

Ser Leu His Val Glu Asp Tyr Lys Cys Phe Asp Pro Asn Arg Ala Tyr
        115                 120                 125

Val Phe Gly Phe Glu Pro His Ser Val Leu Pro Ile Gly Val Ala Ala
    130                 135                 140

Leu Ala Asp Leu Val Gly Phe Met Pro Leu Pro Lys Ile Lys Val Leu
145                 150                 155                 160

Ala Ser Ser Ala Val Phe Tyr Thr Pro Phe Leu Arg Gln Ile Trp Thr
                165                 170                 175

Trp Leu Gly Leu Ile Pro Ala Thr Arg Lys Asn Phe Gln Ser Tyr Leu
```

```
                    180                 185                 190
Gly Ala Gly Tyr Ser Cys Ile Ile Val Pro Gly Val Gln Glu Ile
        195                 200                 205

Leu His Met Asp His Asp Ser Glu Ile Ala Phe Leu Lys Ser Arg Lys
    210                 215                 220

Gly Phe Val Lys Ile Ala Met Gln Ser Gly Cys Pro Leu Val Pro Val
225                 230                 235                 240

Phe Cys Phe Gly Gln Ser Tyr Ala Tyr Lys Trp Trp Arg Pro Lys Gly
                245                 250                 255

Lys Leu Phe Val Lys Ile Ala Arg Ala Ile Lys Phe Thr Pro Ile Val
                260                 265                 270

Phe Trp Gly Arg Tyr Gly Thr Pro Ile Pro Phe Pro Thr Pro Met His
            275                 280                 285

Val Val Val Gly Arg Pro Ile Glu Val Glu Lys Asn Ser Gln Pro Thr
        290                 295                 300

Ile Asp Glu Ile Asn Glu Val His Glu Gln Phe Thr Val Ala Leu Gln
305                 310                 315                 320

Asp Leu Phe Asp Lys Tyr Lys Thr Glu Thr Gly Tyr Pro Gly Leu His
                325                 330                 335

Leu Arg Val Leu
            340

<210> SEQ ID NO 68
<211> LENGTH: 413
<212> TYPE: DNA
<213> ORGANISM: castor DGAT2 genomic

<400> SEQUENCE: 68
agttttgagc actgagcact gaatagcaag aagaagaaga agaagaaatg ggggaagaag      60
cgaatcataa taataataat aataatatca atagtaatga tgagaagaat gaagagaaat     120
caaattatac agttgtaaat tcgagagaac tatacccaac gaacatattt cacgcactgt     180
tagcgttgag catatggatt ggttcaatcc atttcaatct cttcttactc ttcatctctt     240
atctcttcct ttcttttccc acattcctcc tgttagttac tcctcctcct tctccttcat     300
ttttctacta tttttgttta tttattttt aagacatgat taactatcaa tttgtttctt     360
tctgtttttt gaaggattgt tggattttt gtggtgttaa tgttcattcc cga             413
```